US011712525B2

(12) United States Patent
Diaz et al.

(10) Patent No.: US 11,712,525 B2
(45) Date of Patent: Aug. 1, 2023

(54) INJECTION SYSTEM AND METHOD

(71) Applicant: CREDENCE MEDSYSTEMS, INC., Menlo Park, CA (US)

(72) Inventors: Stephen H. Diaz, Palo Alto, CA (US); Gary Steese-Bradley, San Jose, CA (US); Alan E. Shluzas, San Carlos, CA (US); Conor Edward Shanley, Emerald Hills, CA (US); Mina M. Leung, Mountain View, CA (US); Jeff Tillack, Foster City, CA (US)

(73) Assignee: Credence Medsystems, Inc., Menlo Park, CA (US)

( * ) Notice: Subject to any disclaimer, the term of this patent is extended or adjusted under 35 U.S.C. 154(b) by 457 days.

(21) Appl. No.: 16/908,531

(22) Filed: Jun. 22, 2020

(65) Prior Publication Data

US 2020/0398000 A1     Dec. 24, 2020

Related U.S. Application Data

(60) Provisional application No. 62/864,509, filed on Jun. 21, 2019.

(51) Int. Cl.
   *A61M 5/315*    (2006.01)
   *A61M 5/19*     (2006.01)
   *A61J 1/20*     (2006.01)

(52) U.S. Cl.
   CPC .......... *A61M 5/31596* (2013.01); *A61M 5/19* (2013.01); *A61M 5/31511* (2013.01); *A61J 1/201* (2015.05)

(58) Field of Classification Search
   CPC ...... A61M 2005/3231; A61M 5/31596; A61M 5/19; A61M 5/31511; A61M 5/3286;
   (Continued)

(56) References Cited

U.S. PATENT DOCUMENTS

2018/0117261 A1*   5/2018   Steese-Bradley ... A61M 5/2448

FOREIGN PATENT DOCUMENTS

| EP | 0817654 A2 | 1/1998 |
| FR | 1358143 | 4/1964 |

OTHER PUBLICATIONS

PCT International Search Report and Written Opinion for International Appln. No. PCT/US2020/039013, Applicant Credence Medsystems, Inc., dated Sep. 28, 2020 (17 pages).

(Continued)

*Primary Examiner* — Amber R Stiles
*Assistant Examiner* — Nelson Louis Alvarado, Jr.
(74) *Attorney, Agent, or Firm* — VIP Law Group, LLP

(57) ABSTRACT

An injection system includes a syringe body defining a proximal opening at a proximal end thereof and a distal needle interface at a distal end thereof. The system also includes proximal and distal stopper members disposed in the syringe body, forming respective proximal and distal drug chambers. The system further includes a plunger member configured to be manually manipulated to insert the proximal stopper member relative to the syringe body. Moreover, the system includes a fluid conveying assembly including a penetrating member configured to penetrate the distal stopper member to fluidly couple the proximal and distal drug chambers, a distal exit tube, and a transfer member disposed at least partially around a portion of the penetrating member and defining a fluid passage. A distal end of the penetrating member is disposed in the distal exit tube.

42 Claims, 69 Drawing Sheets

(58) Field of Classification Search
CPC .. A61M 5/3295; A61M 5/329; A61M 5/3294;
A61M 2005/2462; A61M 2005/287;
A61M 2205/19; A61M 2205/276; A61M
5/2066; A61M 5/2448; A61M 5/284;
A61M 5/00; A61M 5/1408; A61M 5/162;
A61M 16/0816; A61M 2039/1066; A61M
39/165; A61M 2039/267; A61M 5/3213;
A61M 5/3243; A61M 2005/325; A61M
25/0026; A61M 2025/0681; A61J 1/201
See application file for complete search history.

(56) References Cited

OTHER PUBLICATIONS

PCT International Preliminary Report on Patentability for International Appln. No. PCT/US2020/039013, Applicant Credence Medsystems, Inc., dated Dec. 21, 2021 (13 pages).

\* cited by examiner

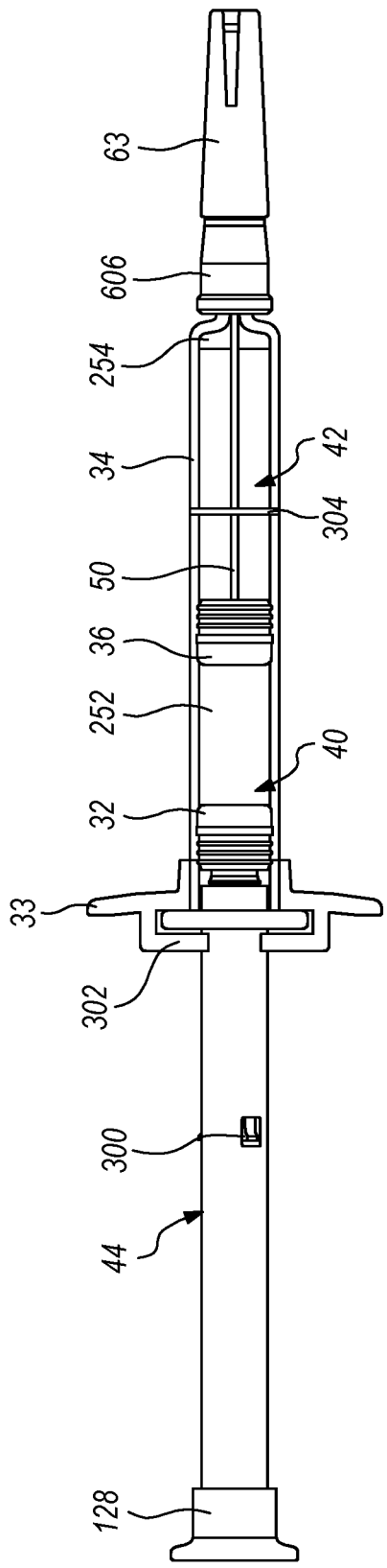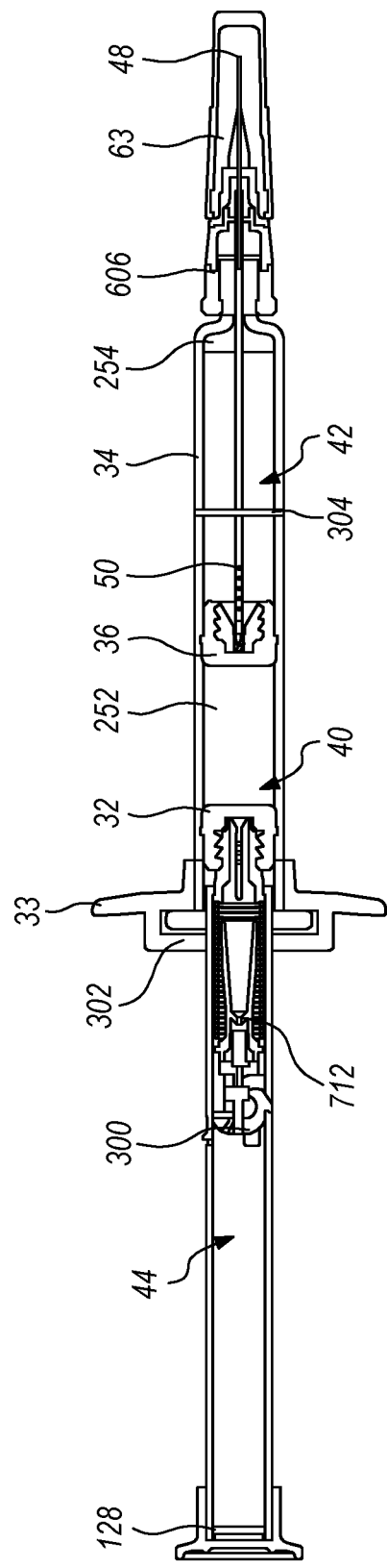
FIG. 7A
FIG. 7B

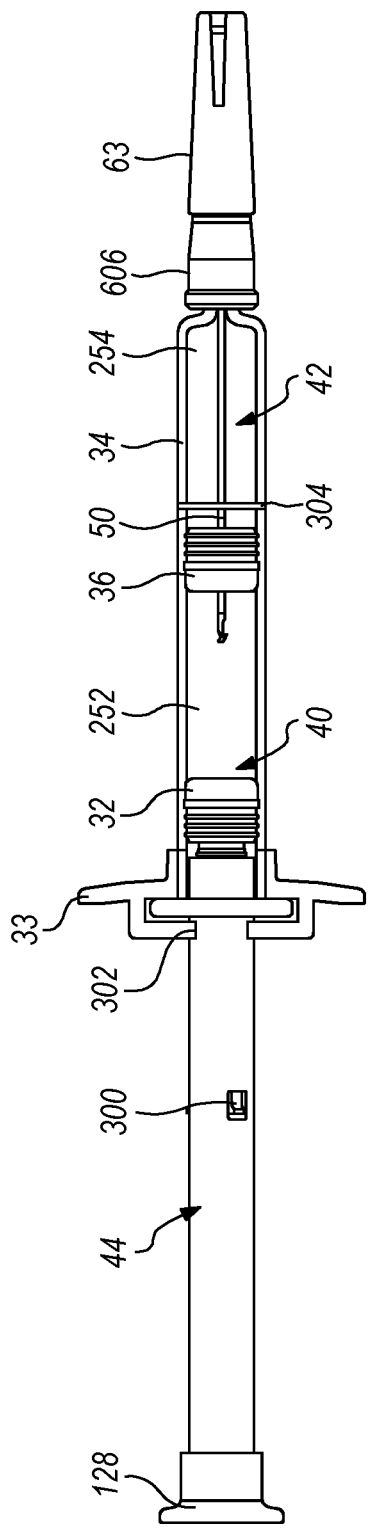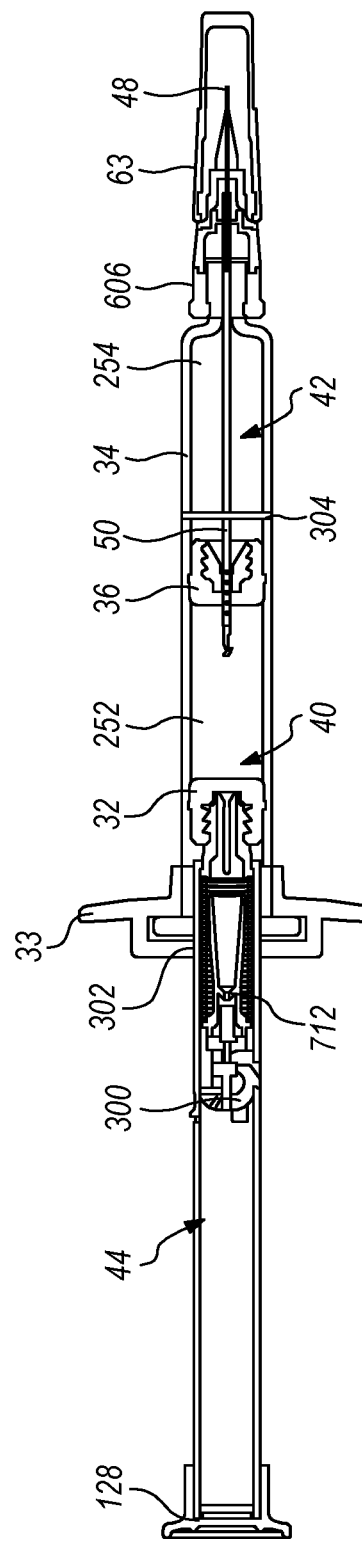

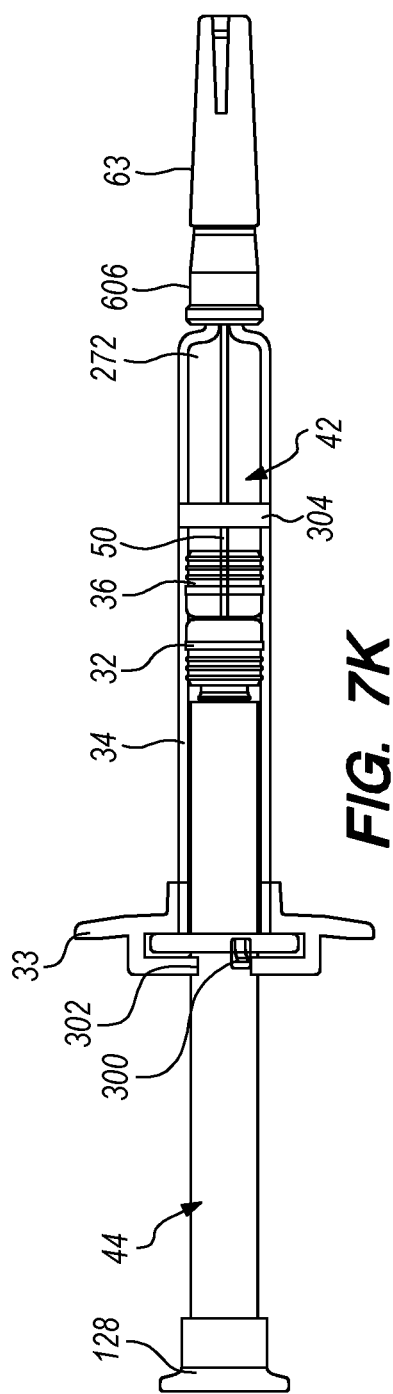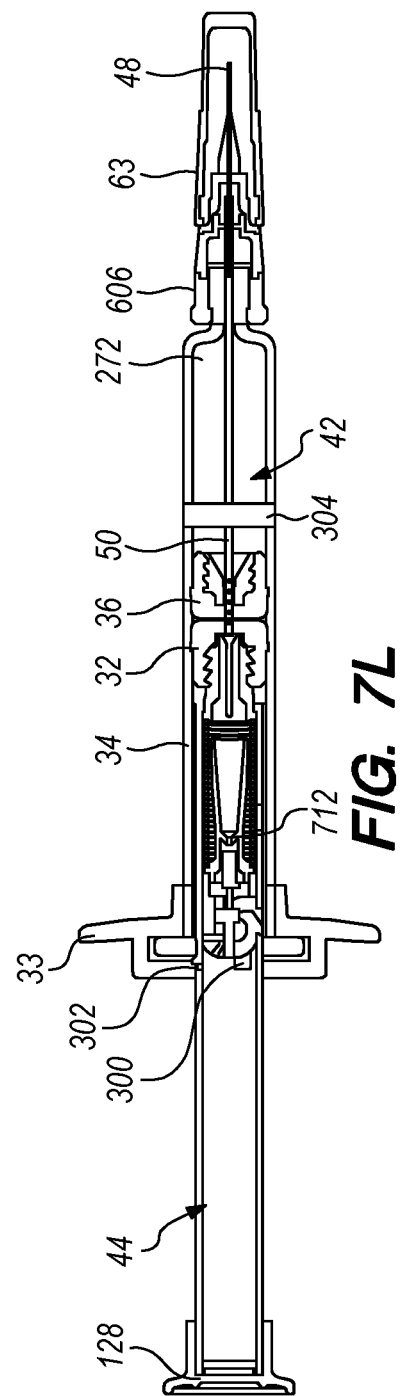

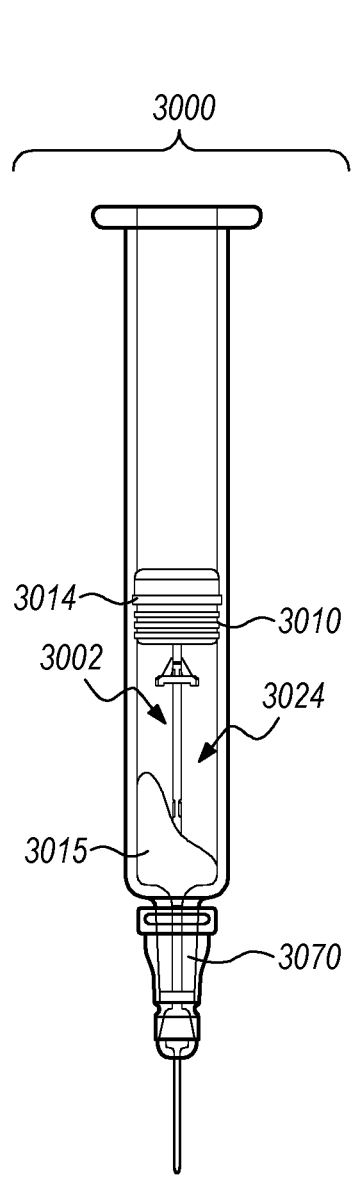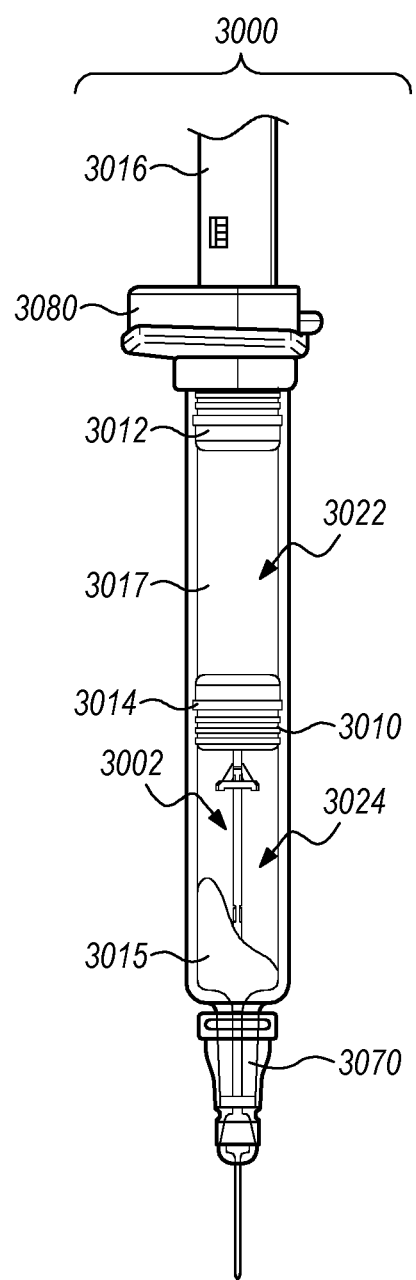
FIG. 33
FIG. 34

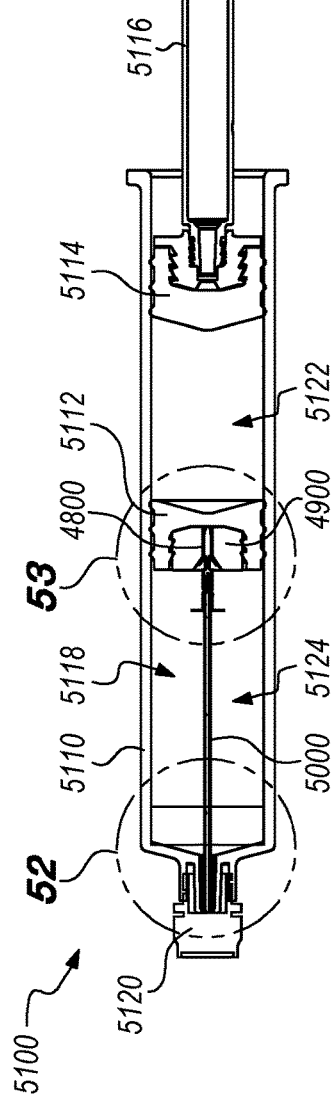
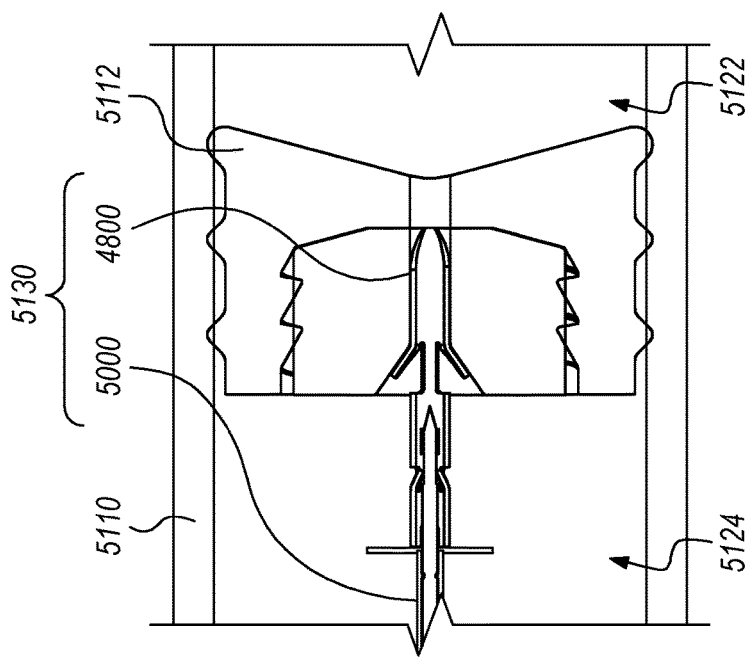
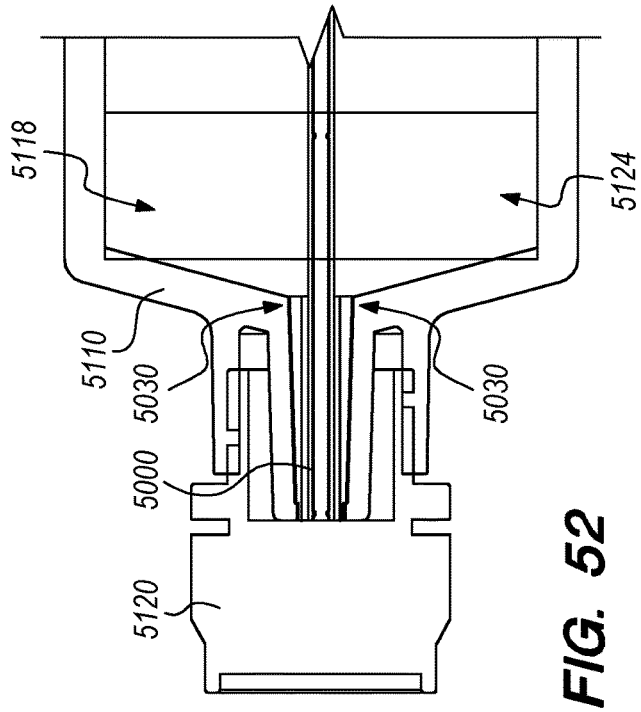
FIG. 51
FIG. 52
FIG. 53

INJECTION SYSTEM AND METHOD

The present application claims priority to (1) U.S. Provisional Patent Application Ser. No. 62/864,509, filed on Jun. 21, 2019, and entitled "SYSTEM AND METHOD FOR SAFETY SYRINGE." This application includes subject matter similar to the subject matter described in the following co-owned U.S. patent applications: (1) U.S. Utility patent application Ser. No. 14/321,706, filed Jul. 1, 2014 and entitled "SAFETY SYRINGE"; (2) U.S. Utility patent application Ser. No. 14/543,787, filed Nov. 17, 2014 and entitled "SYSTEM AND METHOD FOR DRUG DELIVERY WITH A SAFETY SYRINGE"; (3) U.S. Utility patent application Ser. No. 14/696,342, filed Apr. 24, 2015 and entitled "SYSTEM AND METHOD FOR SAFETY SYRINGE"; (4) U.S. Utility patent application Ser. No. 15/801,239, filed on Nov. 1, 2017 and entitled "SYSTEM AND METHOD FOR SAFETY SYRINGE"; (5) U.S. Utility patent application Ser. No. 15/801,259, filed on Nov. 1, 2017 and entitled "SYSTEM AND METHOD FOR SAFETY SYRINGE"; (6) U.S. Utility patent application Ser. No. 15/801,281 filed on Nov. 1, 2017 and entitled "CARTRIDGE SAFETY INJECTION SYSTEM AND METHODS"; (7) U.S. Utility patent application Ser. No. 15/801,304 filed on Nov. 1, 2017 and entitled "SYSTEM AND METHOD FOR SAFETY SYRINGE"; (8) U.S. Provisional Patent Application Ser. No. 62/682,381 filed on Jun. 8, 2018 and entitled "SYSTEM AND METHOD FOR SAFETY SYRINGE"; (9) U.S. Provisional Patent Application Ser. No. 62/729,880 filed on Sep. 11, 2018 and entitled "SYSTEM AND METHOD FOR SAFETY SYRINGE"; (10) U.S. Provisional Patent Application Ser. No. 62/809,369 filed on Feb. 22, 2019 and entitled "SYSTEM AND METHOD FOR SAFETY SYRINGE"; and (10) U.S. Provisional Patent Application Ser. No. 62/827,767 filed on Apr. 1, 2019 and entitled "POLYMERIC INJECTION SYSTEMS." The contents of the above-mentioned applications are fully incorporated herein by reference as though set forth in full.

FIELD OF THE INVENTION

The present invention relates generally to injection systems, devices, and processes for facilitating various levels of control over fluid infusion, and more particularly to systems and methods related to multiple chamber safety syringes in healthcare environments.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs. Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling. The use of needle injection configurations, on the other hand, carries with it the risk of a sharp needle contacting or stabbing a person or structure that is not desired. For this reason, so called "safety syringes" have been developed.

One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for prefilled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface 14). Liquid medicine may reside in the volume, or medicine reservoir, (40) between the distal seal and the distal end (37) of the plunger tip (36). The plunger tip (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross-sectional shape may establish a seal against the syringe body (34)), or be configured to have other cross-sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

In some cases, multi-component injection systems may mix injectable components (e.g., liquids and/or powders) before injection. Some systems utilize a single injection device to draw a component liquid from one container and inject the liquid component into another container to solubilize the dry component therein. The solubilized dry component is then drawn into the injection device for injection into a patient. Such systems require much handling of unsheathed needles, leading to unnecessary exposure of a user to one or more uncapped needles. Further, manually the liquid component from one container to another can result in incomplete transfer of the liquid component and affect the ratio of the components in the final mixed injectable. Moreover, accessing and manipulating multiple containers of components complicates the injection process, thereby increasing the risk of user error. Accordingly, there exists a need for multi-component injection systems that simplify the manual accessing and mixing of multiple components from multiple containers.

These limitations are addressed by multiple chamber injection systems configured to mix and injection multiple components as disclosed in U.S. Utility patent application Ser. Nos. 14/696,342 and 15/801,259, which were previously incorporated by reference herein. However, there remains a need for precise control of multiple chamber injection systems for accurate handling, mixing, and delivery of multi-component injectables.

In addition, an increasing number of injectable liquids (e.g., medicines) have yet another requirement that time of exposure of the injectable liquid to metals (e.g., stainless steel of a needle) be minimized.

It is also desirable to incorporate needle stick prevention technology into the injection system. The ability to retract the sharp end of the needle at least partially inside of the syringe protects the person giving the injection and the patient from inadvertent needle stick injuries.

There is a need for injection systems which address the shortcomings of currently-available configurations. In particular, there is a need for multiple chamber safety injection solutions with precise control, which may utilize the existing and relatively well-controlled supply chain of conventionally delivered prefilled syringe assemblies such as those described in reference to FIGS. 5A and 5B.

SUMMARY

Embodiments are directed to injection systems. In particular, the embodiments are directed to multiple chamber safe injection systems with precise control of handling, mixing, and delivery of multi-component injectables.

In one embodiment, an injection system includes a syringe body defining a proximal opening at a proximal end thereof and a distal needle interface at a distal end thereof. The system also includes proximal and distal stopper members disposed in the syringe body, forming a proximal drug chamber between the proximal and distal stopper members and a distal drug chamber between the distal stopper member and the distal end of the syringe body. The system further includes a plunger member configured to be manually manipulated to insert the proximal stopper member relative to the syringe body. Moreover, the system includes a fluid conveying assembly including a penetrating member configured to penetrate the distal stopper member to fluidly couple the proximal and distal drug chambers. The fluid conveying assembly also includes a distal exit tube, wherein a distal end of the penetrating member is disposed in the distal exit tube. The fluid conveying assembly further includes a transfer member disposed at least partially around a portion of the penetrating member, wherein the distal transfer member defines a fluid passage.

In one or more embodiments, the transfer member includes a sleeve disposed on the portion of the penetrating member. The sleeve may define the fluid passage on the surface of the portion of the penetrating member. The transfer member may include a chamfered corner at a proximal end thereof. A diameter of the distal end of the geometric feature may be substantially the same as or larger than a diameter of the proximal end of the distal exit tube. The penetrating member may be configured to pierce the distal stopper member and the transfer member may be configured to dilate the distal stopper member and maintain an open fluid passage.

In one or more embodiments, the portion of the penetrating member has a reduced diameter relative to a geometric feature at a distal end of the penetrating member and the distal exit tube at a proximal end of the portion of the penetrating member. A distal end of the geometric feature and a proximal end of the distal exit tube may form proximal and distal shoulders at proximal and distal ends of the portion of the penetrating member respectively.

In one or more embodiments, the transfer member has a closed configuration wherein the transfer member is disposed around the portion of the penetrating member between the proximal and distal shoulders, the transfer member having a first diameter, and an open configuration wherein the transfer member has a second diameter larger than the first diameter such that the penetrating member and the distal exit tube are slidable within the transfer member. The transfer member may be converted from the closed configuration to the open configuration by the application of between approximately 6 lbf and approximately 10 lbf on the distal exit tube provided by hydraulic pressure on the distal stopper member from the plunger member.

In one or more embodiments, the transfer member includes a distally directed funnel at a distal end thereof. A proximal end of the distal exit tube may be disposed in the distally directed funnel when the transfer member is in the closed configuration. The proximal end of the distal exit tube may be configured to wedge open the transfer member with distal movement of the distal exit tube relative to the transfer member to transform the transfer member from the closed configuration to the open configuration.

In one or more embodiments, the first diameter is less than or equal to a diameter of the distal end of the geometric feature. The second diameter may be greater than a diameter of the proximal end of the distal exit tube. The transfer member may be configured to transform from the closed configuration to the open configuration with application of a pre-determined amount of force to the distal exit tube. The pre-determined amount of force may be approximately 6 lbf to approximately 10 lbf of distally directed force.

In one or more embodiments, the transfer member includes a living hinge. The transfer member may include an elongate side opening. The distal stopper member may include a funnel configured to guide a proximal end of the penetrating member toward a center of the distal stopper member. The transfer member may include a radially extending member configure to physically interfere with the funnel to halt proximal movement of the transfer member relative to the funnel and the distal stopper member when the radially extending member contacts the funnel. The penetrating member may include a geometric feature at a proximal end thereof. The geometric feature may be configured to penetrate the distal stopper member.

In one or more embodiments, the distal exit tube includes a split open distal end. The distal exit tube may include a proximal side opening and a proximal end opening. The penetrating member may have a length greater than a distance between the proximal side opening and the proximal end opening. The system may also include a ring welded to the distal exit tube. The ring may be configured to prevent a distal end of the distal exit tube from extending more than a predetermined distance toward a distal end of the distal needle interface.

In one or more embodiments, the system has a transport configuration wherein the penetrating member is entirely disposed in the distal drug chamber, a transfer configuration wherein the penetrating member has at least partially pierced the distal stopper member, and wherein the penetrating member and the transfer member are at least each partially disposed in the proximal drug chamber, and a mixed configuration wherein the proximal and distal stopper members are in contact with each other, thereby transferring a first drug component from the proximal drug chamber to the distal drug chamber to mix the first drug component with a second drug component in the distal drug chamber. The fluid passage may form a fluid path between the proximal and distal chambers when the system is in the transfer configuration. The transfer member may not fully penetrate the proximal stopper member in the mixed configuration or during injection. After the system has reached the mixed configuration, the distal exit tube wedges open the transfer member and slides proximally within the transfer member with further distal movement of the distal stopper member.

In one or more embodiments, the system is configured to transform from the transport configuration to the transfer configuration with application of a pre-determined amount of force to the distal stopper member. The pre-determined amount of force is approximately 3-5 lbf of distally directed force. The distal exit tube may include a distal end opening at a distal end thereof, and a proximal side opening disposed in the distal drug chamber. First and second sizes of the respective proximal and distal drug chambers may be modified by movement of the proximal and distal stopper members relative to the syringe body. The proximal and distal drug chambers may respectively contain first and second components of a drug to be mixed together prior to injecting into a patient. The transfer member may be formed from metal or polymer.

In one or more embodiments, the transfer member includes a latch having latched and unlatched states. The latch prevents axial movement of the penetrating member and distal exit tube relative to the transfer member in the latched state, and the latch allows axial movement of the penetrating member and distal exit tube relative to the transfer member in the unlatched state. The latch may include a plastic hinge. The plastic hinge may open to transform the latch from the latched to the unlatch state. The plastic hinge may open in response to application of a predetermined amount of force to the latch. The predetermined amount of force may be approximately 6 lbf to approximately 10 lbf of distally directed force. The latch may include a frangible link to hold the transfer member in the latched state until a predetermined amount of force is applied to the latch. The predetermined amount of force may be approximately 6 lbf to approximately 10 lbf of distally directed force.

In another embodiment, a syringe modifying device includes a fluid conveying assembly. The fluid conveying assembly includes a penetrating member configured to penetrate a distal stopper member of a syringe to fluidly couple proximal and distal drug chambers of the syringe. The fluid conveying assembly also includes a distal exit tube configured to couple to a proximal end of a needle of the syringe, wherein a distal end of the penetrating member is disposed in the distal exit tube. The fluid conveying assembly further includes a transfer member disposed at least partially adjacent a portion of the penetrating member, wherein the distal transfer member defines a fluid passage configured to fluidly couple the distal and proximal drug chambers upon penetration of the distal stopper member by the penetrating member. The distal exit tube may include a slot configured to couple the distal exit tube to the proximal end of the needle.

In still another embodiment, an injection system includes a syringe body defining a proximal opening at a proximal end thereof and a distal needle interface at a distal end thereof. The system also includes proximal and distal stopper members disposed in the syringe body, forming a proximal drug chamber between the proximal and distal stopper members and a distal drug chamber between the distal stopper member and the distal end of the syringe body. The system further includes a plunger member configured to be manually manipulated to insert the proximal stopper member relative to the syringe body. Moreover, the system includes a fluid conveying assembly. In addition, the system includes a finger flange including an anti-retraction mechanism. The anti-retraction mechanism has a brake tab configured to provide an opposing force to the plunger member to prevent proximal movement thereof relative to the brake tab, and a retention feature configured to maintain the anti-retraction mechanism in a recess in the finger flange.

In one or more embodiments, the finger flange also includes another recess configured to mount the finger flange on a flange of the syringe body. The anti-retraction mechanism may also include a plurality of fit tabs configured to reduce a tolerance between the recess and a dimension of the anti-retraction mechanism. The anti-retraction mechanism may be a metal clip.

In one or more embodiments, the brake tab is an elastic and self-energizing pawl. The brake tab may be disposed at an acute angle in a distal direction relative to a plane of the anti-retraction mechanism. The acute angle and an elasticity of the brake tab may increase a frictional force against the plunger member upon retraction in a proximal direction. The acute angle of the brake tab also creates a reaction force parallel to the plunger member, exerted by a sharp curved edge of the brake tab contacting the surface of the plunger member. This force also prevents the plunger member from moving in the proximal direction. The acute angle and an elasticity of the brake tab may cause the brake tab to exert an outward force through the anti-retraction mechanism to an inner wall of the finger flange when the plunger member is retracted in a proximal direction.

In one or more embodiments, the finger flange also includes an opening having an edge configured to interfere with and retain the anti-retraction mechanism in the recess. The anti-retraction mechanism may have a "C" or "0" shape. The anti-retraction mechanism may prevent removal of the plunger member from the syringe body after the plunger member has been inserted into the syringe body. The opposing force may include a frictional force and a reaction force.

In yet another embodiment, an injection system includes a syringe body defining a proximal opening at a proximal end thereof and a distal needle interface at a distal end thereof. The system also includes proximal and distal stopper members disposed in the syringe body, forming a proximal chamber between the proximal and distal stopper members and a distal chamber between the distal stopper member and the distal end of the syringe body. The system further includes a plunger member configured to be manually manipulated to insert the proximal stopper member relative to the syringe body. Moreover, the system includes a fluid conveying assembly. The fluid conveying assembly includes a piercing tube configured to penetrate the distal stopper member. The assembly also includes a solid elongate member, where the piercing tube is disposed at least partially around a portion of the solid elongate member. The assembly further includes a distal tube, where a distal end of the solid elongate member is disposed in a proximal end of the distal tube. The piercing tube includes a pair of vacuum stops configured to increase a force required for a proximal end of the piercing tube to penetrate fully through the distal stopper member. After the proximal end of the piercing tube has penetrated fully through the distal stopper member, the piercing tube defines a fluid passage between the proximal and distal chambers.

In one or more embodiments, each of the vacuum stops include a radially outward and distally extending tab. The may also include a funnel insert disposed in the distal stopper member and configured to interfere with the vacuum stops on the piercing tube to halt proximal movement of the piercing tube relative to the funnel insert and the distal stopper member when the radially extending member contacts the funnel insert. The funnel insert may be configured to guide a proximal end of the piercing tube toward a center of the distal stopper member.

In one or more embodiments, the piercing tube also includes a tubular member, and a disc disposed orthogonal to a longitudinal axis of the tubular member at a distal end thereof. The disc may define a plurality of radially inward telescoping stops connecting the disc to the tubular member. The plurality of radially inward telescoping stops may define an adjustable opening in an approximate center of the disc. The adjustable opening may have a smaller configuration configured to prevent the solid elongate member from passing completely through the disc and the piercing tube, and a larger configuration configured to allow the solid elongate member to pass completely through the disc and the piercing tube.

In one or more embodiments, the distal tube includes a proximally facing shoulder at a proximal end thereof configured to interfere with the plurality of radially inward telescoping stops when the adjustable opening is in the smaller configuration to prevent proximal movement of the distal tube relative to the piercing tube. A diameter of the adjustable opening in the smaller configuration may be smaller than an outer diameter of the shoulder. A diameter of the adjustable opening in the larger configuration may be larger than the outer diameter of the shoulder. Moving the tubular member proximally away from the disc may transform the adjustable opening from the smaller configuration to the larger configuration. Moving the disc distally away from the tubular member may transform the adjustable opening from the smaller configuration to the larger configuration.

In one or more embodiments, the adjustable opening is converted from the smaller configuration to the larger configuration by the application of a predetermined amount of proximally directed force on the piercing tube provided by hydraulic pressure on the distal stopper member from the plunger member. The predetermined amount of proximally directed force may be between approximately 7.5 lbf and approximately 10 lbf. The tubular member penetrating the distal stopper member may exert a radially inward force on the plurality of radially inward telescoping stops to hold the adjustable opening in the smaller configuration.

In one or more embodiments, the piercing tube further including a pair of radially inward and proximally extending tabs configured to limit distal movement of the solid elongate member relative to the piercing tube. The solid elongate member may include a distally facing shoulder configured to interfere with the radially inward and proximally extending tabs to limit distal movement of the solid elongate member relative to the piercing tube.

In one or more embodiments, the piercing tube defines a proximal end opening, a middle opening, and a distal opening. After the proximal end of the piercing tube has penetrated fully through the distal stopper member, the fluid passage between the proximal and distal chambers includes the proximal end opening, the middle opening, and the distal opening. The system may also include a vacuum in the distal chamber. The piercing tube may include a chamfered corner at a proximal end thereof.

In one or more embodiments, the system has a transport configuration where the piercing tube is entirely disposed in the distal chamber and the distal stopper member, a transfer configuration where the piercing tube has partially pierced the distal stopper member, and where an open proximal end of the piercing tube is disposed in the proximal chamber, and a mixed configuration where the proximal and distal stopper members are in contact with each other, thereby transferring a first drug component from the proximal chamber to the distal chamber to mix the first drug component with a second drug component in the distal chamber. The piercing tube may form a fluid path between the proximal and distal chambers when the system is in the transfer configuration. The piercing tube may not fully penetrate the distal stopper member. After the system has reached the mixed configuration, the solid elongate member may be released from the piercing tube with further distal movement of the distal stopper member. The system may be configured to transform from the transport configuration to the transfer configuration with application of a pre-determined amount of force to the distal stopper member. The pre-determined amount of force may be between approximately 7.5 lbf and approximately 10 lbf of distally directed force. The proximal and distal chambers may respectively contain first and second components of a drug to be mixed together prior to injecting into a patient.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIGS. 15 to 21A depict a fluid conveying assembly in a dual chamber injection system according to some embodiments.

FIGS. 31 to 34 depict a dual chamber injection system conversion kit and its use in converting a single chamber injection system to a dual chamber injection system according to some embodiments.

FIGS. 48 to 63 depict a dual chamber injection system including a fluid transfer assembly and components of same according to some embodiments.

Figure 1A:
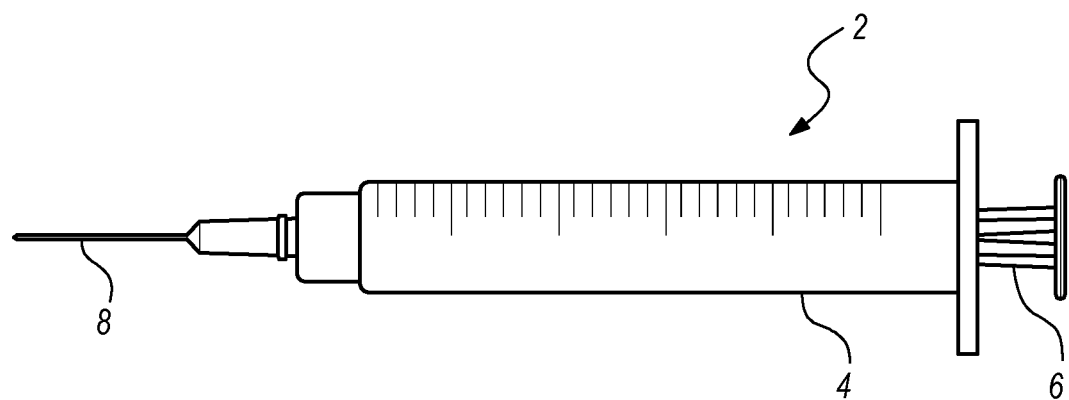
FIGS. 1A to 5C illustrate various aspects of conventional injection syringe configurations.
Figure 1B:
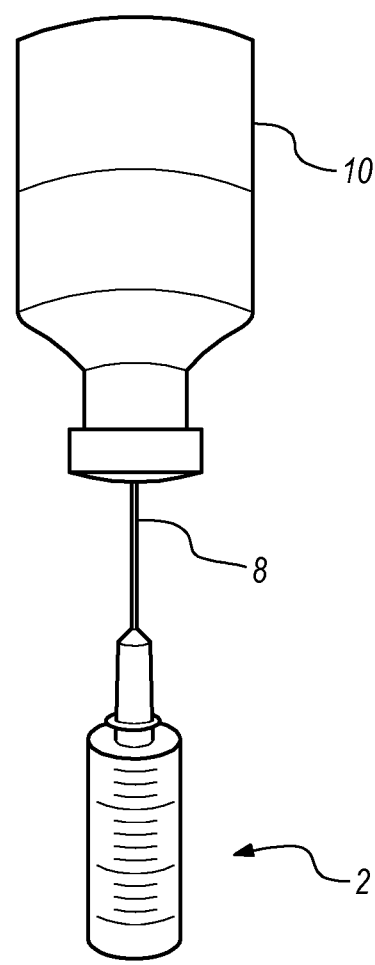
Figure 2A:
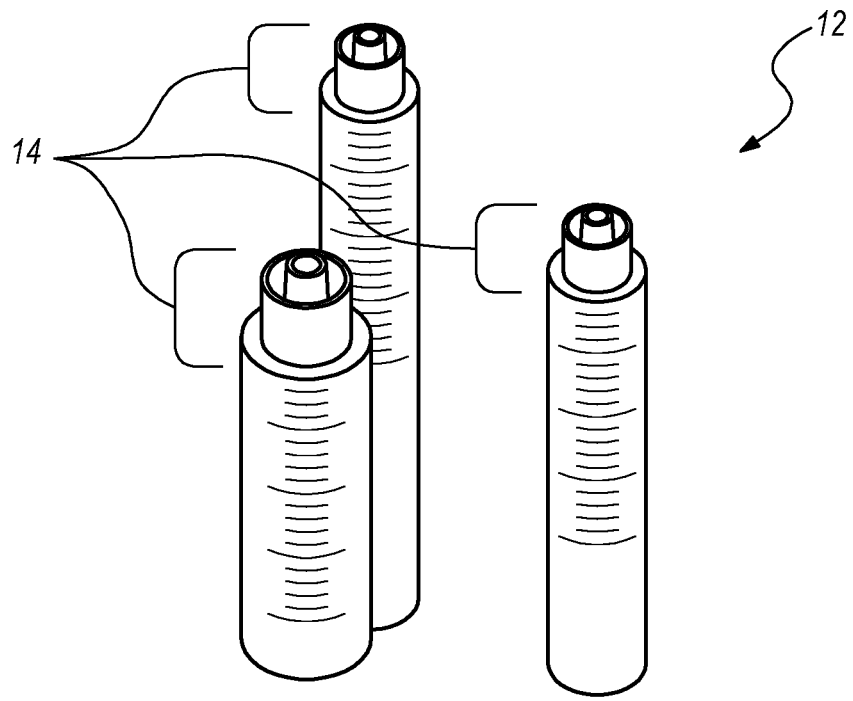
Figure 2B:
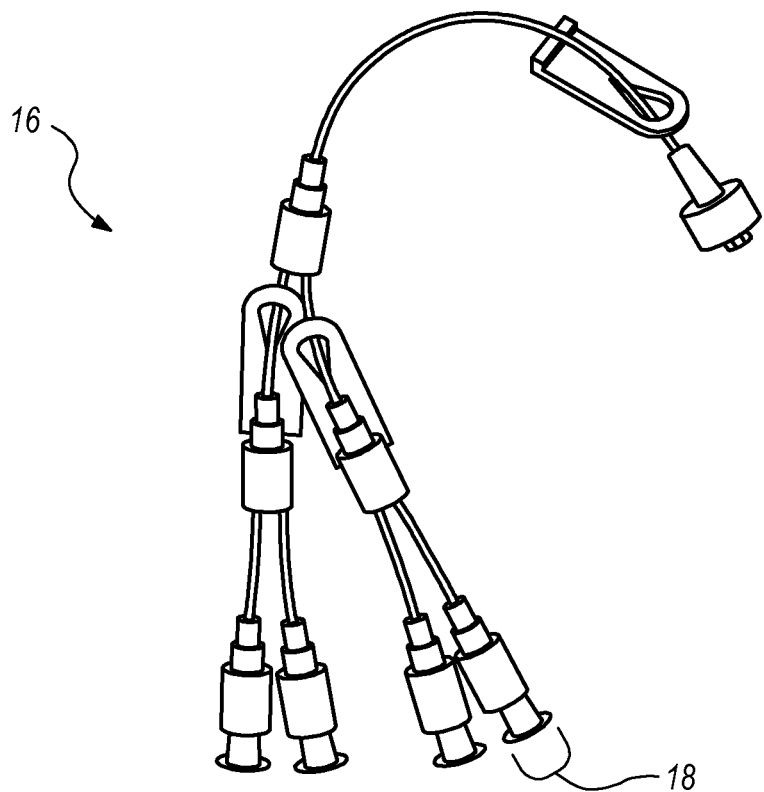
Figure 3:
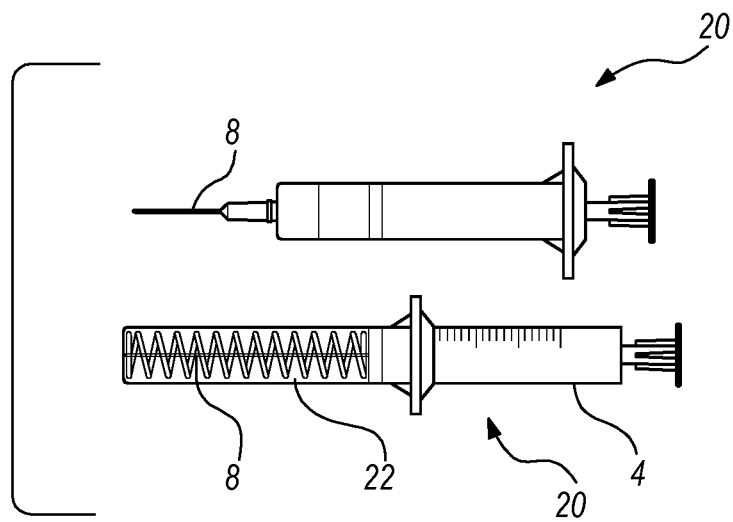
Figure 4A:
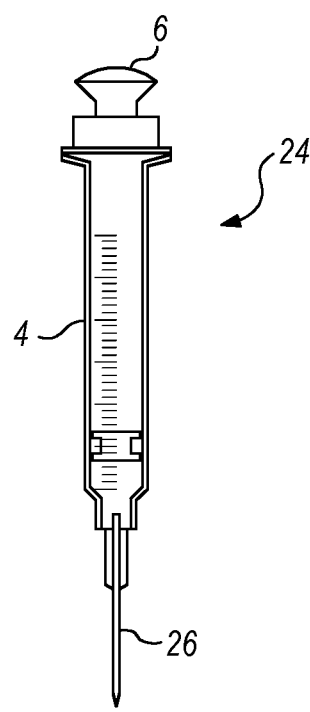
Figure 4B:
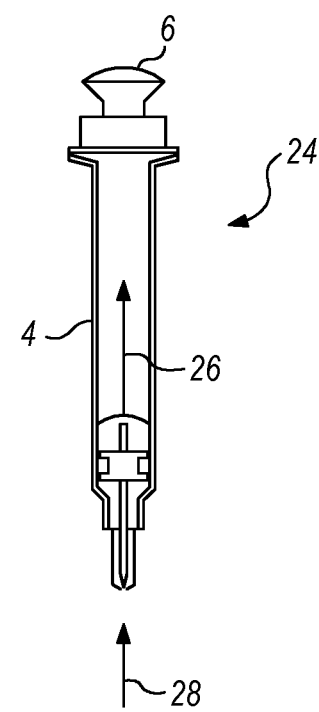
Figure 5A:
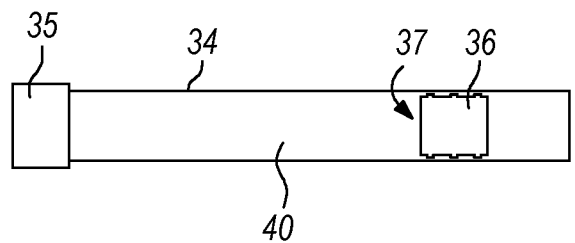
Figure 5B:
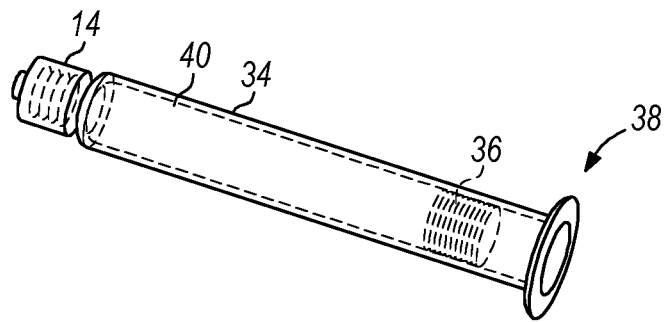
Figure 5C:
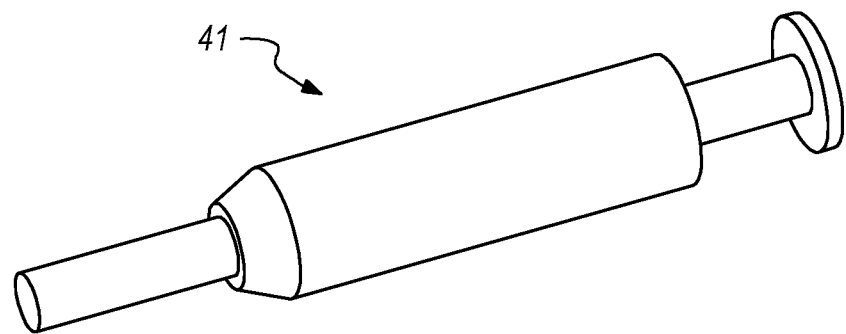

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Prefilled Dual Chamber Safe Injection Systems

Figure 6A:
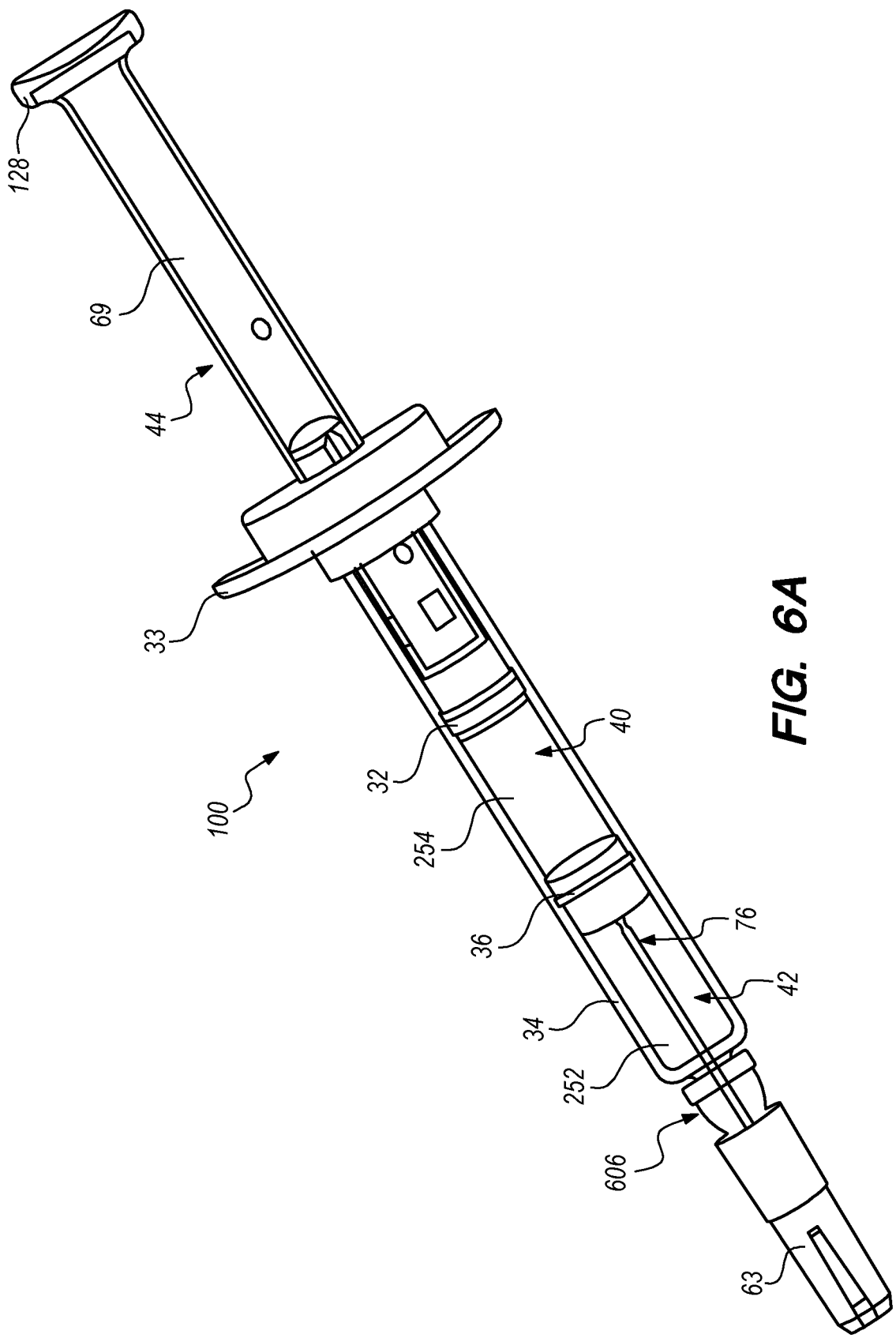
FIGS. 6A and 6B illustrate various aspects of syringe based dual chamber safe injection systems wherein a distal needle end/tip may be withdrawn into a protected configuration after use according to some embodiments.
Figure 6B:
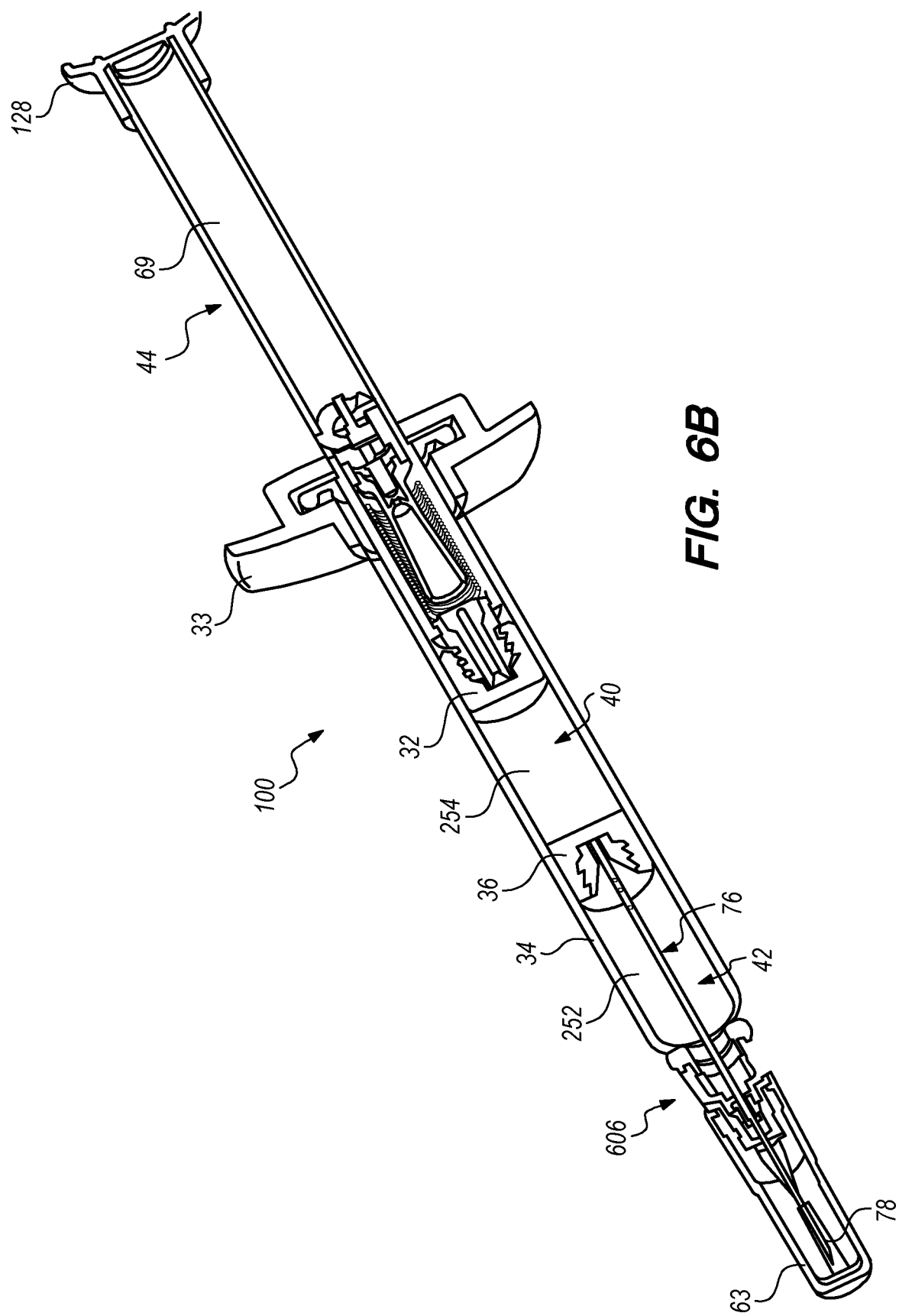

Referring to FIGS. 6A and 6B, a perspective and a longitudinal cross-section view of a prefilled dual chamber safe injection system (100) are shown, with a conventional off-the-shelf prefilled syringe body (34) with conventional proximal and distal stopper members (32, 36) disposed therein. The proximal and distal stopper members (32, 36) together with the syringe body (34) define proximal and distal chambers (40, 42). The proximal and distal stopper members (36, 37) occlude the proximal and distal ends of the proximal chamber (40). The distal stopper member (36) occludes a proximal end of the distal chamber (42). In some embodiments, the distal end of the proximal stopper member (32) and the proximal end of the distal stopper member (36) may be coated with a lubricious polymer coating (e.g., PTFE), the first and second polymer coatings of the proximal and distal stopper members (32, 36), together with the syringe body (34) define the proximal chamber (40). The lubricious polymer coating also serves to isolate the rubber of the proximal and distal stopper members (32, 36) from the second liquid (254). The proximal and distal stopper members (32, 36) may be oriented as shown in FIGS. 6A and 6B or the distal stopper (36) may be flipped so the lubricious coating faces the distal chamber (42) such that the first liquid (252) in the distal chamber (42) contacts the lubricious coating for storage.

A needle coupling assembly (606) is disposed at the distal end of the distal chamber (42) with a needle cover member (63) installed for storage. The dual chamber safe injection system facilitates sequential injection of a first liquid (252) from the distal chamber (42) followed by injection of a second liquid (254) from the proximal chamber subject to sequential insertion of a plunger assembly (44) relative to the syringe body (34) to various degrees by a user. The plunger assembly (44) includes the proximal stopper member (32), a plunger housing member (69) and a plunger manipulation interface (128). The first and second liquids located in the distal and proximal chambers (42, 40) respectively may be any liquid or gel, such as aqueous or oil based medicine solutions.

The dual chamber safe injection system (100) has a staked needle configuration wherein upon presentation to the user, a needle assembly, including a needle spine assembly ("needle") (76) and a needle coupling assembly (606) are mounted in position ready for injection after removal of a needle cover member (63) which may comprise an elastomeric sealing material on its internal surface to interface with a needle distal end (78) and/or a distal housing portion during storage. Alternatively, the needle cover member (63) may comprise a vent (not shown) for allowing pressure resulting from the transfer of the liquids (252, 254) to escape from inside the syringe body (34) while preventing contamination from entering the syringe body (34). While, the staked needle is depicted as mounted in position, the staked needle may be removably coupled to the syringe body (34) using a Luer slip or a Luer lock interface (not shown), with the proximal end (50) of the needle member extending through the Luer interface and into the distal chamber (42). Alternatively, the needle may be fixedly or removably mounted to the flange on a cartridge body instead of a syringe. Such cartridge injection systems are disclosed in U.S. Utility patent application Ser. No. 15/801,281, which was previously incorporated by reference herein. In the embodiments depicted in FIGS. 6A and 6B, a significant portion of the safe needle retraction hardware resides within a plunger housing.

Figure 7C:
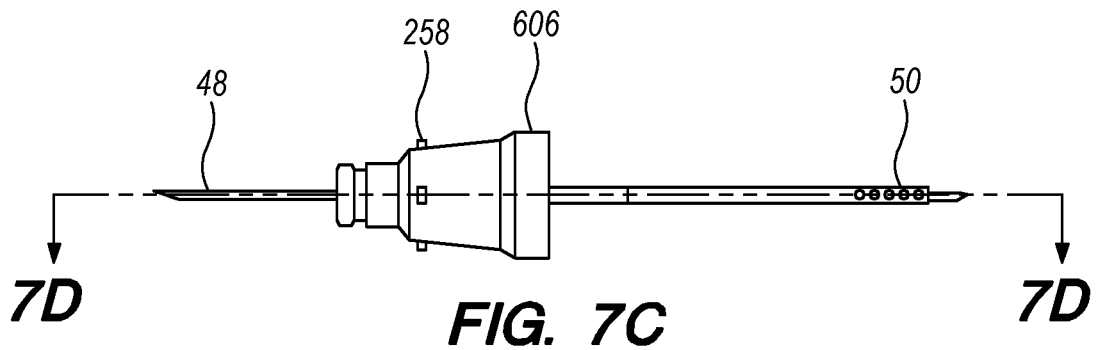
FIGS. 7A to 7P illustrate various aspects of syringe based dual chamber safe injection systems during steps in methods for mixing and injecting using same according to some embodiments.
Figure 7D:
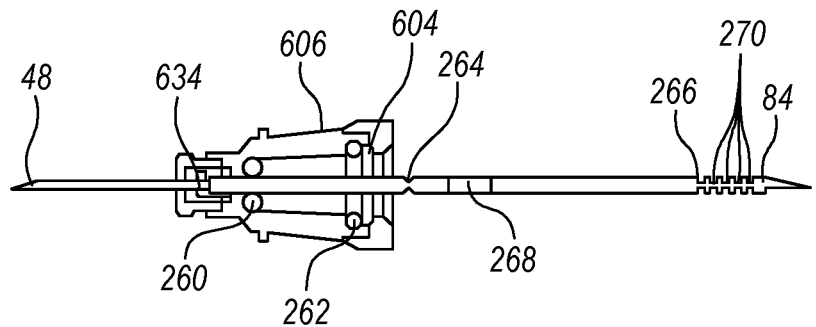
Figure 7E:
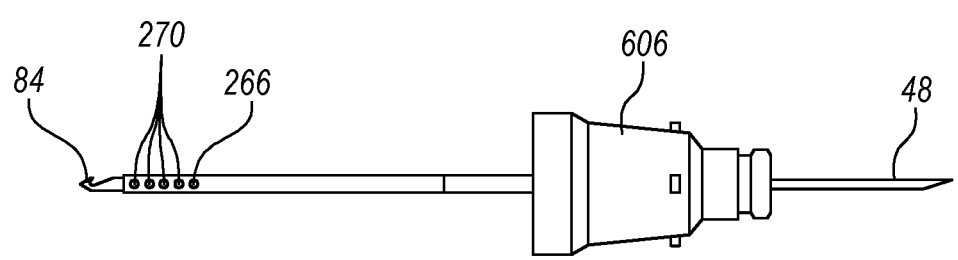
Figure 7F:
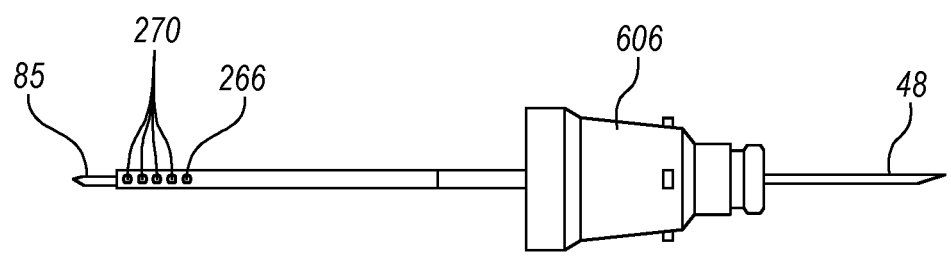
Figure 7I:
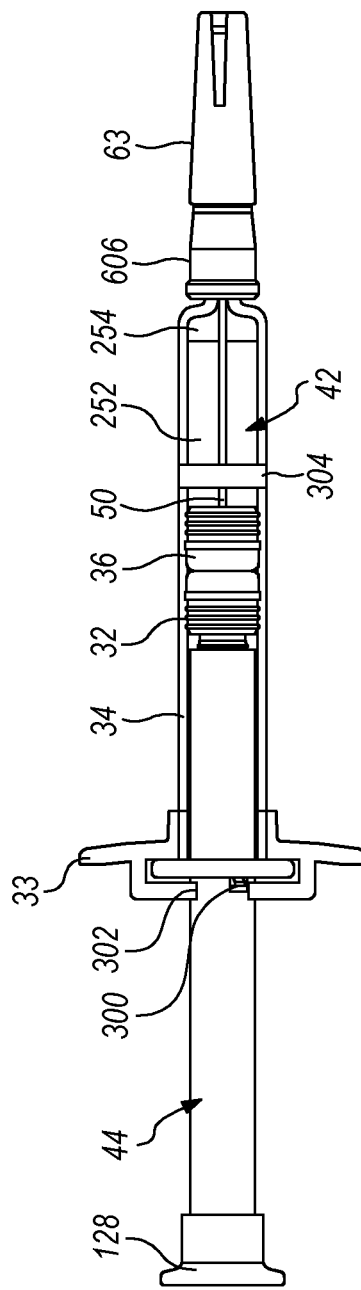
Figure 7J:
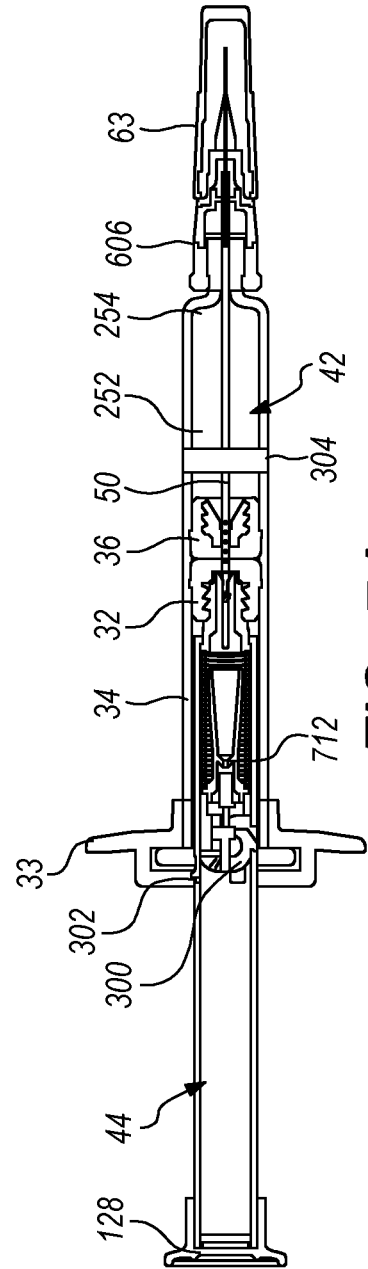
Figure 7M:
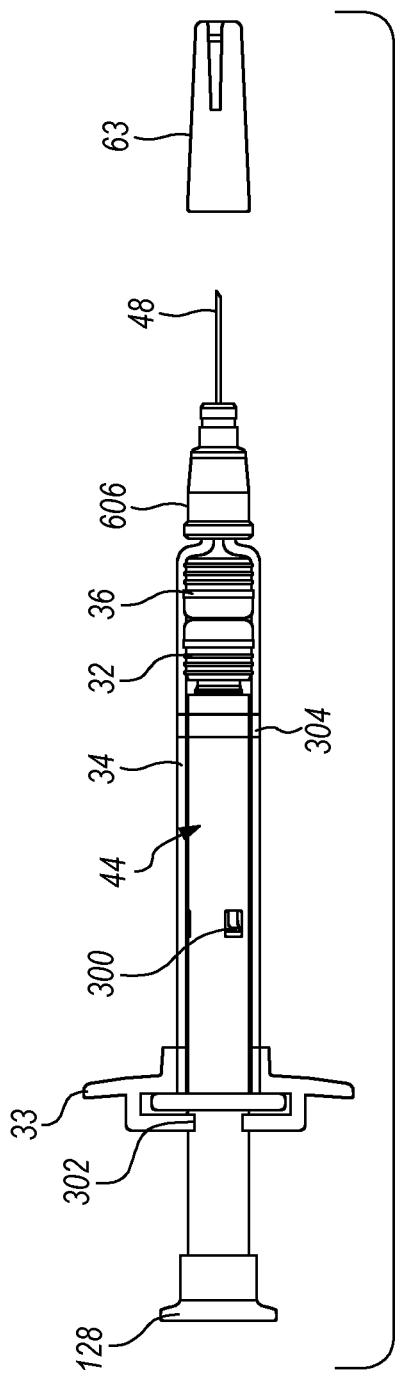
Figure 7N:
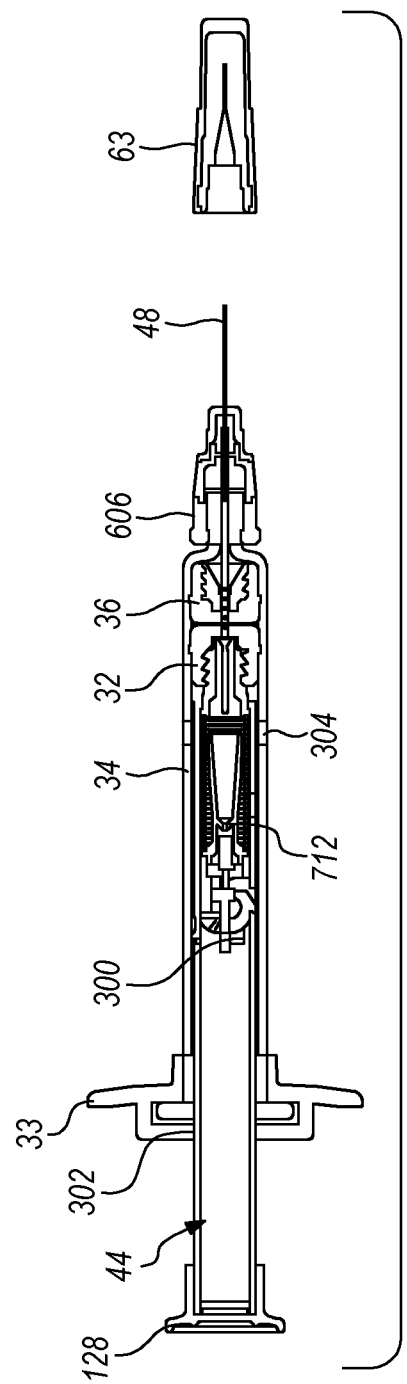
Figure 7O:
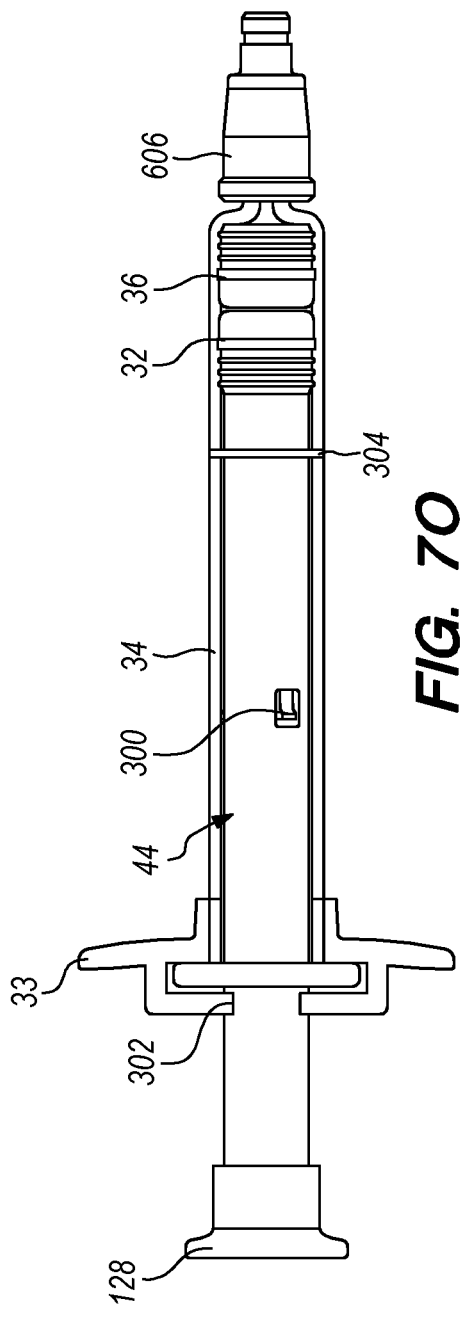
Figure 7P:
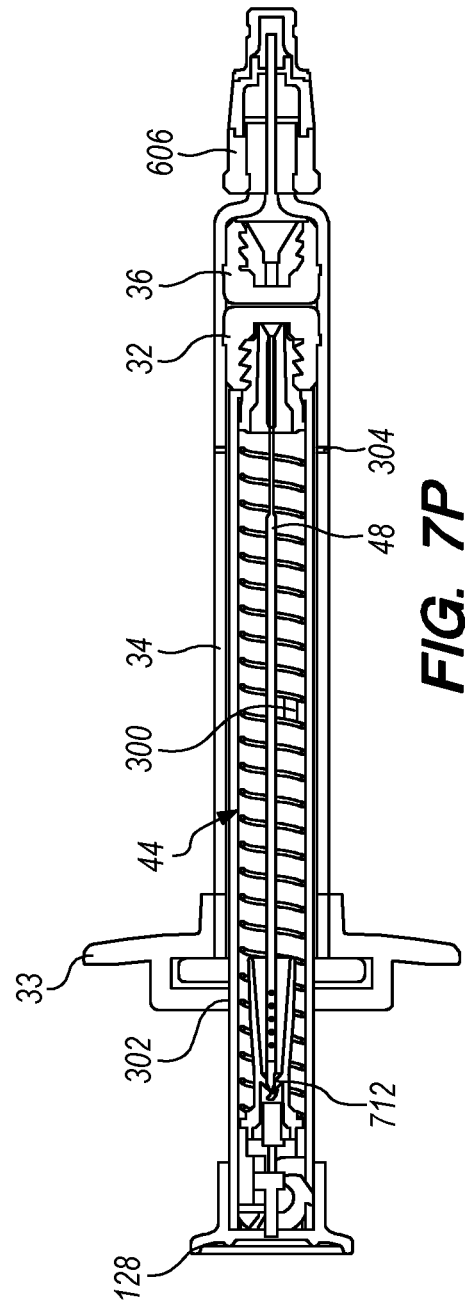

Referring to FIGS. 7A-7P, various aspects of configurations designed to facilitate injection of multi-part medications and retractions of a needle into a syringe body are illustrated, wherein two or more medication components are combined to form an injection combination or solution shortly before delivery into the patient. In one variation, a liquid first medicine component/diluent (252) may be combined with a substantially non-liquid second medicine component (254), such as a powdered form, of a drug agent, such as a freeze-dried or lyophilized drug component, shortly before injection. The configurations described herein in reference to FIGS. 7A-7P relate to dual-chamber configurations, wherein two or more chambers within the same syringe body (34) are utilized to carry, mix, and inject an injection solution.

Referring to FIGS. 7A and 7B, proximal and distal medicine chambers (40, 42) are formed by a distal stopper member (36) in between two portions of the interior of a syringe body (34), such that the distal medicine chamber (42) contains an air or gas gap, as well as a non-liquid medication (254); a proximal medicine chamber (40), on the opposite side of the distal stopper member (36) contains a liquid diluent (252), which is proximally contained by a proximal stopper member (32). The liquid diluent (252) is a first component of a medicine and the non-liquid medication (254) is a second component of the medicine.

Referring to FIG. 7C, and the associated cross sectional view in FIG. 7D, various components of a needle coupling assembly (here a so-called "staked" needle coupling assembly (606) is illustrated, but other needle assemblies as described below, including Luer-coupled as well as staked configurations, may be utilized). Lug features (258) are configured to assist with coupling the needle coupling assembly (606) to a needle cover member (63), as shown in FIG. 7A, for example. A small O-ring may be utilized as a sealing member (260) around the needle shaft, while a larger O-ring may be utilized as a sealing member (262) at the syringe body (34)/needle coupling assembly (606) interface. Alternatively, the small O-ring (260) and the large O-ring (262) may be combined into a single seal that performs both of the O-ring sealing functions. Also, the small O-ring (260) may be used to seal both around the needle shaft and to the syringe body (34).

The needle includes a plurality (e.g., four) of proximal openings/ports (270) configured to allow for entry of a liquid diluent, to be expelled out of a more distally-located middle opening/aperture (266); a lumen plug (268) occludes the needle lumen to create the flow path from the proximal openings (270) to the middle opening (266) under conditions such as those described above in reference to FIGS. 6N and 7H. The needle also includes a distal opening (264) on the opposite side of the lumen plug (268) from the middle opening (266). The distal opening (264) is fluidly coupled to the needle distal end (48) through the needle to inject liquid into a patient.

Referring to FIG. 7E, a proximal harpoon interface (84) is configured to serially penetrate proximal and distal stopper members (32, 36), and couple with a coupling feature (such as a needle retention feature are illustrated, for example, in FIGS. 7N and 7P, element (712)) in the plunger rod. FIG. 7F illustrates a spike style harpoon coupling interface (85) that is configured to serially pierce both proximal and distal stopper members (32, 36) and couple with a coupling feature in the plunger rod to retract the needle member at least partially into the plunger rod after the injection has been given to the patient.

FIGS. 7A, 7B, and 7G-7P illustrate a sequence of actions for an injection procedure utilizing a dual chamber safe injection system such as that described above. Referring to FIGS. 7A and 7B, an injection assembly is in a stable configuration wherein it may be shipped or brought to an injection patient care scenario; a first drug component/liquid diluent (252) is isolated from a second non-liquid drug component (254), both within a syringe body on opposite sides of a distal stopper member (36).

FIGS. 7G and 7H illustrate initial insertion movement of the plunger assembly (44), advancing the distal (36) and proximal (32) stopper members together relative to the syringe body (34). Referring to FIG. 7H, with advancement sufficient to stab the proximal end (50) of the needle assembly across the distal stopper member (36), a fluid pathway is formed between the two previously isolated chambers (40, 42) of the syringe body (34), such that the liquid first drug component (252) in the proximal medicine chamber (40) may flow into at least one of the proximal openings (270), through the transfer pipe (46), and exit the more distal middle opening (266), to reach the non-liquid second drug component (254) in the distal medicine chamber (42).

FIGS. 7I and 7J illustrate that with further insertion until the stopper members (36, 32) are immediately adjacent each other, the liquid first drug component/diluent (252) has moved into the distal medicine chamber (42) to join the non-liquid second drug component (254). FIGS. 7K and 7L illustrate that with time and/or manual agitation, the liquid first drug component/diluent (252) and previously non-liquid second drug component (254) become mixed to form a mixed medication solution (272).

In some embodiment, especially with lyophilized non-liquid second drug components, the mixed medication solution (272) may be formed with minimal or no agitation or time passage. In another embodiment, especially with drugs which are held in suspension or emulsified drugs, vigorous shaking may be necessary to facilitate mixing. In the case of vigorous shaking it is useful to the user to be able to remove their thumb from the plunger manipulation interface (128). During transfer of liquid first medicine component (252) from the proximal to the distal medicine chambers (40, 42) pressure may build up in the distal medicine chamber (42). This pressure acts upon the proximal and distal stopper members (32, 36) to resist stopper motion. The pressure buildup may also move the stopper members (32, 36) and plunger manipulation interface (128) proximally if the user does not have their thumb restraining the plunger assembly (44). Mixed configuration latches or "mix clicks" in the plunger assembly (44) (described in U.S. Utility patent application Ser. No. 15/801,259, which was previously incorporated by reference herein) may be utilized to provide resistance to plunger manipulation interface (128) motion due to pressure buildup and allow the user to release their thumb from the plunger manipulation interface (128) for shaking or mixing of the drug. The mix clicks may also provide an audible and/or tactile indication that the transfer of liquid first medicine component (252) has been completed. The distal medicine chamber (42) may also include an agitation device, which assists in mixing of the medicine components.

With the assembly ready for injection of the mixed solution (272), the needle cover member (63) may be removed and the patient may be injected with the exposed needle distal end (48) with depression/insertion of the plunger assembly (44) and associated stopper members (36, 32) as shown in FIGS. 7M and 7N. Referring to FIGS. 7O and 7P, with full depression/insertion of the plunger assembly (44) and associated stopper members (32, 36), the sharp needle distal end/point (48) may automatically retract at least partially through the distal and proximal stopper members (36, 32) to a safe position within either the syringe body (34), the needle coupling assembly (606), or at least partially within the plunger assembly (44). Automatic retraction of the needle at least partially within the plunger is described in U.S. utility patent application Ser. No. 14/696,342, which was previously incorporated by reference herein.

Further details regarding multiple chamber injection systems (components, methods using same, etc.) are disclosed in U.S. Utility patent application Ser. No. 15/801,259, and U.S. Provisional Patent Application Ser. Nos. 62/682,381 and 62/729,880, which were all previously incorporated by reference herein.

Exemplary Fluid Transfer Assembly for Dual Chamber Safe Injection Systems

Figure 8:
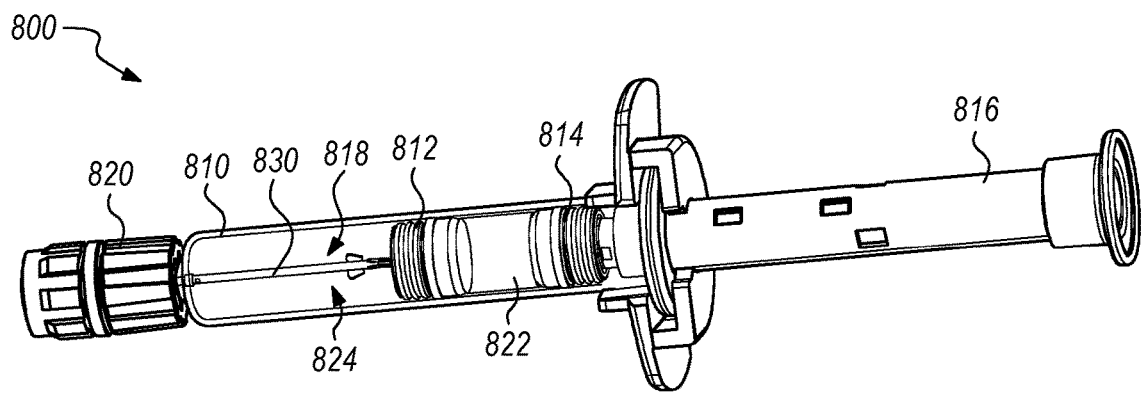
FIGS. 8 and 9 depict dual chamber injection systems according to some embodiments.

FIG. 8 depicts a dual chamber injection system 800 including a fluid transfer assembly configured to provide precise control of the handling, mixing, and delivery of the components of a multi-component injectable according to some embodiments. Similar to the dual chamber injection systems 100 depicted in FIGS. 6A-7B and 7G-7P, the dual chamber injection system 800 includes a syringe body 810, proximal and distal stopper members 812, 814, and a plunger member 816. The plunger member 816 is inserted into an interior 818 of the syringe body 810 via a proximal opening in the syringe body. The syringe body 810 also includes a distal needle interface 820 at the distal end thereof. While the dual chamber injection systems 100 depicted in FIGS. 6A-7B and 7G-7P have a staked needle, the syringe body 810 has a Luer lock type distal needle interface 820. The distal needle interface 820 is not limited to Luer lock and may be any other type of needle/tubing interface. The proximal and distal stopper members 812, 814 together with the syringe body 810 define a proximal drug chamber 822. The distal stopper member 814 and the syringe body 810 define a distal drug chamber 824. The plunger member 816 may be manually manipulated to insert the proximal stopper member 812 relative to the syringe body 810. If a non-compressible fluid is disposed in the proximal drug chamber 822, inserting the proximal stopper member 812 also inserts the distal stopper member 814 relative to the syringe body 810.

While the dual chamber injection systems 100 depicted in FIGS. 6A-7B and 7G-7P have a needle with various openings for fluid transfer and delivery (see FIGS. 7C-7F), the dual chamber injection system 800 includes a fluid conveying assembly 830 for fluid transfer and delivery.

Figure 9:
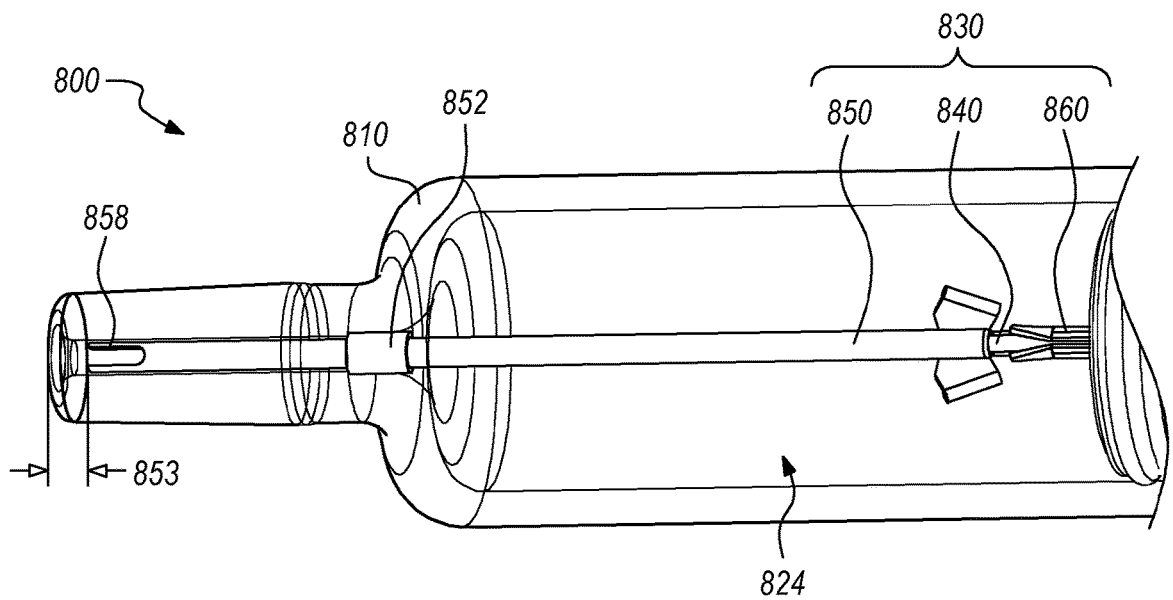

As shown in FIG. 9, the fluid conveying assembly 830 according to some embodiments includes a penetrating member 840, a distal exit tube 850, and a transfer member 860. The penetrating member 840 is partially disposed within the distal exit tube 850 and partially disposed within the transfer member 860. The distal exit tube 850 is generally an elongate tubular member including a jam ring 852 welded thereon to prevent distal movement of the distal exit tube 850 during use of the dual chamber injection system 800. The position of the jam ring 852 on the distal exit tube is configured to leave a seal clearance 853 between the distal end of the distal exit tube and the distal end of the syringe body 810. The seal clearance 853 prevents the syringe cap from leaking during storage and transport.

Figure 10:
FIG. 10 depicts components of a fluid conveying assembly for use in dual chamber injection systems according to some embodiments.

FIG. 10 depicts the penetrating member 840 inserted into the distal exit tube 850 without the overlying transfer member 860 omitted for clarity according to some embodiments. The junction between the penetrating member 840 and the distal exit tube 850 is welded to form a watertight seal to prevent unintended fluid flow. The penetrating member 840 is generally an elongate solid member including a geometric feature 844 at a proximal end thereof. The geometric feature 844 depicted in FIG. 10 has a three-dimensional arrowhead shape that is configured to penetrate the distal stopper member 814. The outer diameter of the penetrating member 840, with the exception of the geometric feature 844, is substantially consistent and configured to fit snugly within an interior of the distal exit tube 850. In other words, the outer diameter of the penetrating member 840 is slightly less than an inner diameter of the distal exit tube 850.

The distal end of the geometric feature 844 has an outer dimension/diameter that is larger than the outer diameter of the penetrating member 840. The proximal end of the distal exit tube 850 also has an outer dimension/diameter that is larger than the outer diameter of the penetrating member 840. As such, the distal end of the geometric feature 844 and the proximal end of the distal exit tube 850 form proximal and distal shoulders 846, 854 surrounding an annularly recessed portion 848 of the penetrating member 840. The annularly recessed portion 848 is sized and shaped to hold the transfer member in a closed configuration (described below).

The penetrating member 840 is of sufficient length to substantially fill the interior of the distal exit tube 850 between a proximal opening 842 of the distal exit tube 850 and a side opening 856 formed in the side wall of the distal exit tube 850 near the jam ring 852. In the embodiment depicted in FIG. 10, the distal end of the penetrating member 840 extends to point X adjacent to and proximal of the side opening 856. In addition to filling the interior of the distal exit tube 850 between the proximal opening 842 in the side opening 856, the penetrating member 840 has sufficient additional length to form the annularly recessed portion 848.

The distal exit tube also includes a distal opening having a split end 858, and is hollow between the side opening 856 and the distal opening 858. The distal tube between the side opening 856 and the distal opening 858 form a flow path Y through which fluid can exit from the distal drug chamber and out the distal opening 858. The split end at the distal opening 858 is configured to couple the distal exit tube 850 to a tubular member that forms a distal exit from the dual chamber injection system 800. Exemplary tubular members include but are not limited to needles and tubing, both of which may be attached to Luer connectors.

Figure 11:
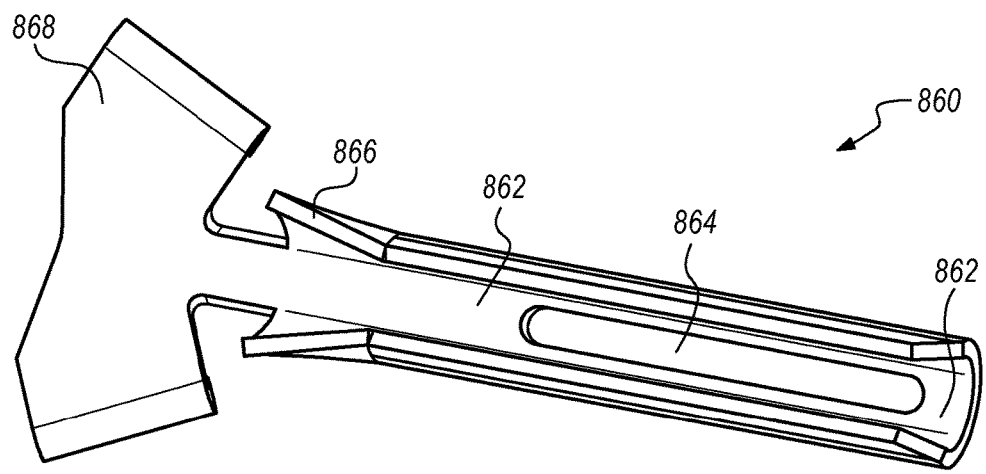
FIGS. 11 to 14 depict assembly of components of a fluid conveying assembly for use in dual chamber injection systems according to some embodiments.

FIGS. 11 to 14 depict the transfer member 860 as it is being mounted onto the annularly recessed portion 848 of the penetrating member 840 according to some embodiments. FIG. 11 depicts the transfer member 860 before it is mounted. The transfer member 860 may be cut from a sheet of metal. The transfer member 860 includes two plastic/living hinges 862 and a longitudinal opening 864 sized and shaped to facilitate conversion of the transfer member 860 between a closed and an open configuration (described below). The plastic/living hinges 862 and the longitudinal opening 864 can be modified to modulate a gripping force of the transfer member 860 on the penetrating member 840. The transfer member 860 also includes a funnel 866 at a distal end thereof. The transfer member 860 further includes two radially extending members 868 each in the shape of a wing that are configured to interfere with the distal stopper member 814 to prevent distal movement of the distal stopper member 814 relative to the transfer member 860.

Figure 12:
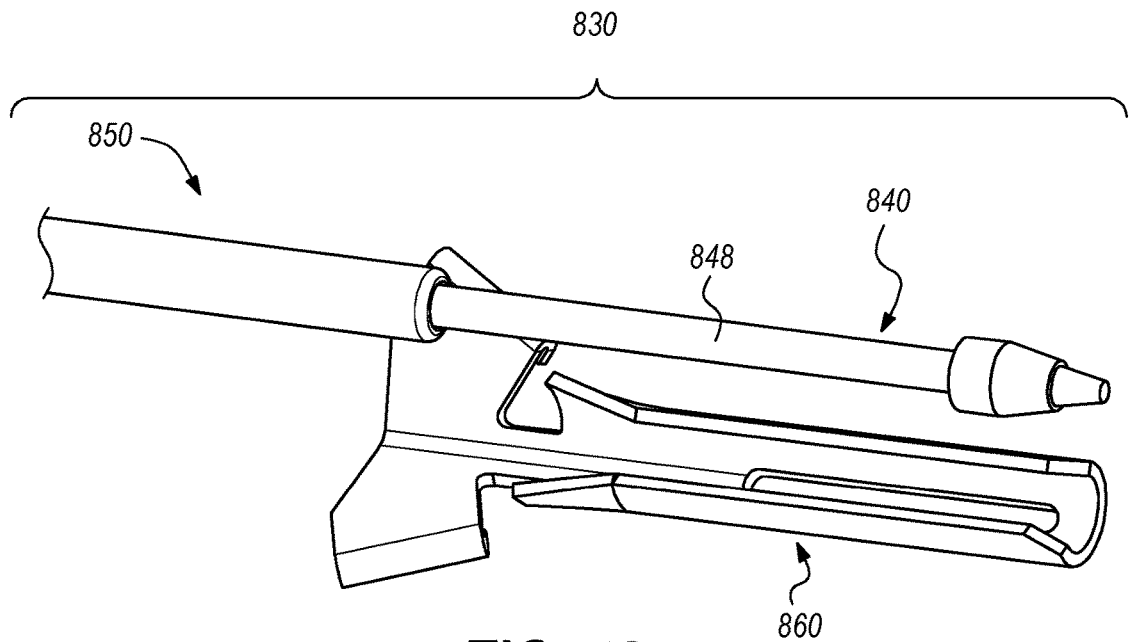

FIG. 12 depicts the relative positions of the penetrating member 840 (which is already coupled to the distal exit member 850) and the transfer member 860 before the fluid conveying assembly 830 is assembled. The transfer member 860 is aligned with the annularly recessed portion 848 of the penetrating member 840.

Figure 13:
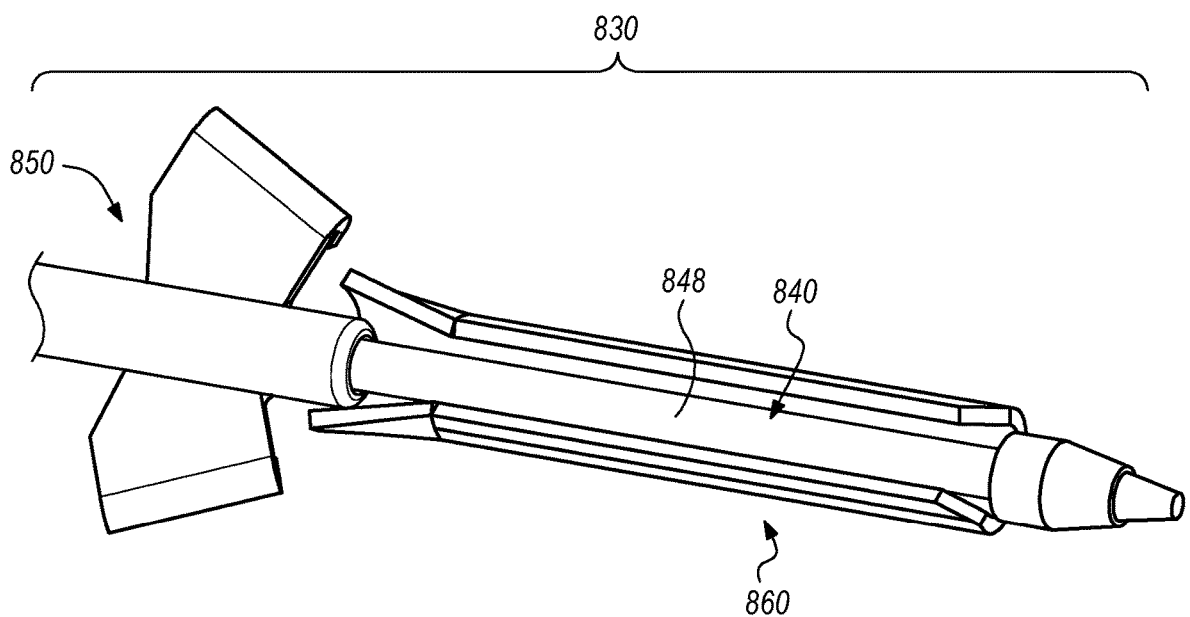

FIG. 13 depicts movement of the penetrating member 840 and the transfer member 860 toward each other such that the transfer member 860 is disposed over the annularly recessed portion 848 of the penetrating member 840.

Figure 14:
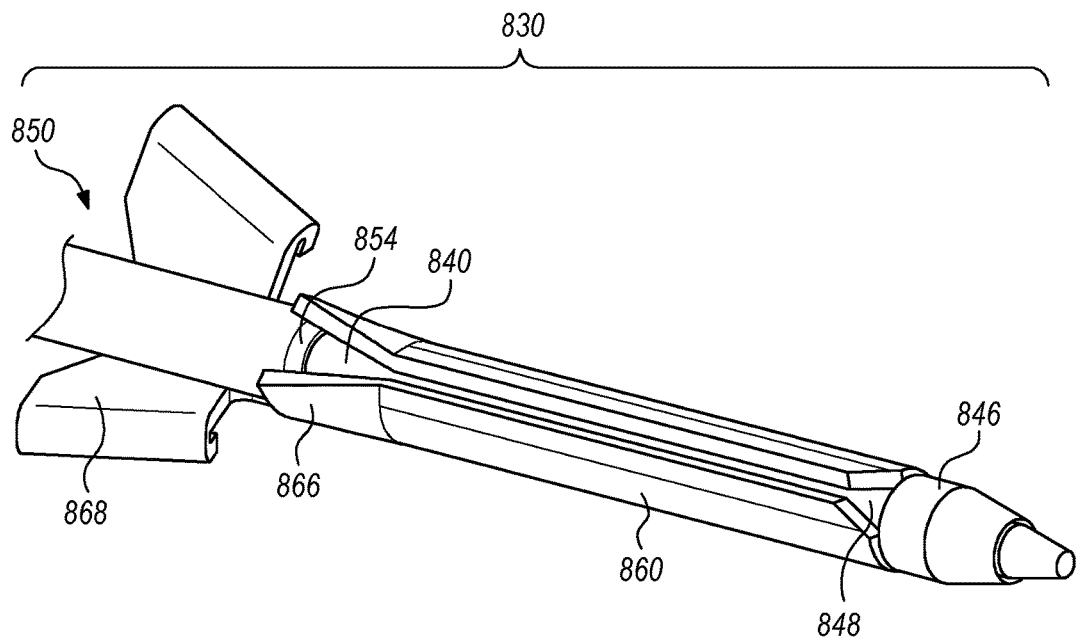

FIG. 14 depicts crimping of the transfer member 860 around the annularly recessed portion 848 of the penetrating member 840. The crimping may be performed manually or by a machine/robot. Crimping the transfer member 860 seats the transfer member 860 in the annularly recessed portion 848 of the penetrating member 840. Once seated, the transfer member 860 is in its closed configuration. In the closed configuration, the proximal shoulder 846 interferes with a proximal end of the transfer member 860 to prevent distal movement of the penetrating member 840 relative to the transfer member 860. Further, in the close configuration, the distal shoulder 854 interferes with the funnel 866 at the distal end of the transfer member 860 to prevent proximal movement of the penetrating member 840 relative to the transfer member 860.

With the transfer member 860 in the closed configuration depicted in FIG. 14 and seated in the annularly recessed portion 848 of the penetrating member 840, the fluid conveying assembly 830 is ready to be assembled with the other components of the dual chamber injection system 800.

Figure 15:
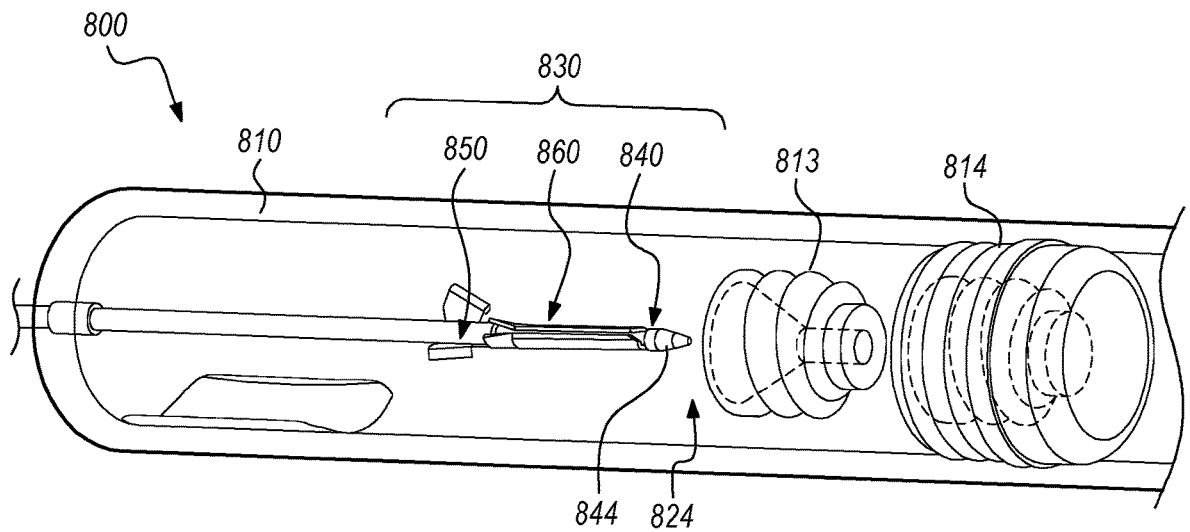

FIG. 15 depicts an exploded view of select components of a dual chamber injection system 800 according to some embodiments. The assembled fluid conveying assembly 830 is inserted through a proximal opening in the syringe body 810 until the jam ring 852 interferes with a distal end of the syringe body 810 to prevent further distal movement of the fluid conveying assembly 830 relative to the syringe body 810. The distal stopper member 814 includes a guide/funnel 813 configured to direct the geometric feature 844 at a proximal end of the penetrating member 840 to a center of the distal stopper member 814. The distal stopper member 814 including the guide/funnel 813 is then inserted through the proximal opening in the syringe body 810 until the geometric feature 844 at the proximal end of the penetrating member 840 is seated in the center of the guide/funnel 813 adjacent the center of the distal stopper member 814. Inserting the distal stopper member 814 defines the distal drug chamber 824. Next, the proximal stopper member 812 is inserted through the proximal opening in the syringe body 810 to define the proximal drug chamber 824 (see FIG. 8). The plunger member 816 is then inserted through the proximal opening in the syringe body 810 and coupled to the proximal stopper member 812 (e.g., by screwing the plunger member 816 into the proximal stopper member 812; see FIG. 8).

Figure 16:
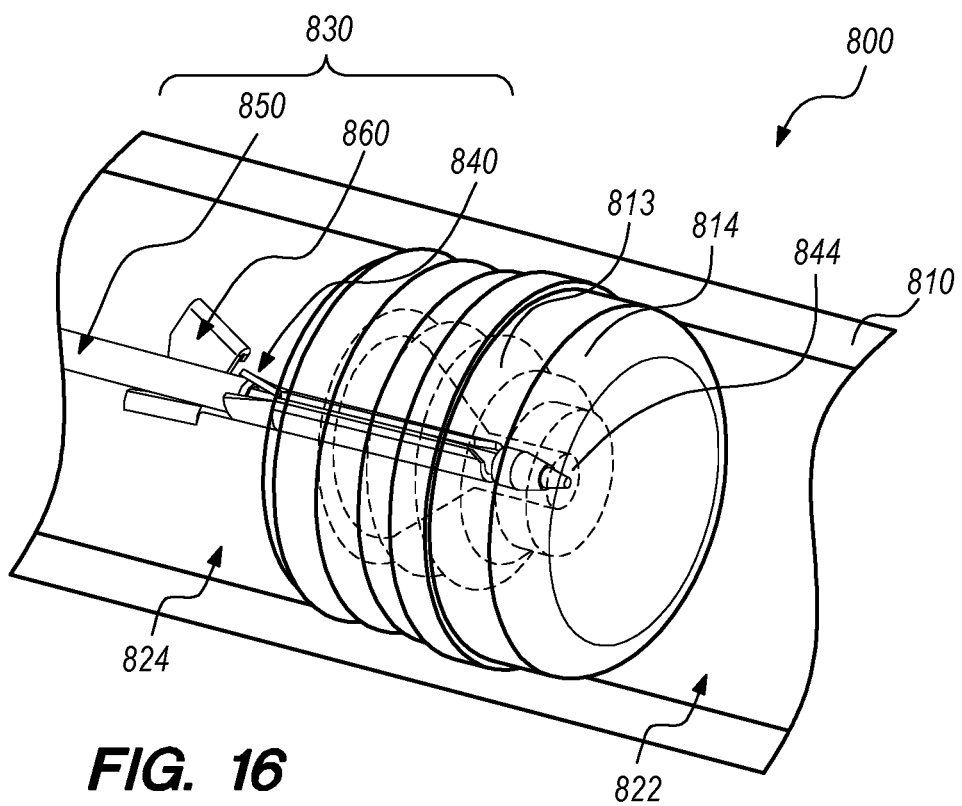

FIG. 16 depicts a dual chamber injection system 800 in a transport/as shipped configuration according to some embodiments. In the transport/as shipped configuration, a proximal end of the geometric feature 844 of the penetrating member 840 rests in respective centers of the guide/funnel 813 and the distal stopper member 814. The proximal end of the geometric feature 844 rests on an inner surface of the distal stopper member 814 and is ready to pierce the distal stopper member 814 in response to a distally directed force applied to the distal stopper member 814. In the transport/as shipped configuration, the proximal and distal drug chambers 822, 824 are isolated from each other, and any drug components contained therein are also isolated from each other. Further, any drug component contained in the proximal drug chamber 822 is only exposed to the glass sides of the syringe body 810 and the proximal and distal stopper members 812, 814, which may facilitate transport of metal sensitive drug components in the proximal drug chamber 822.

Figure 17:
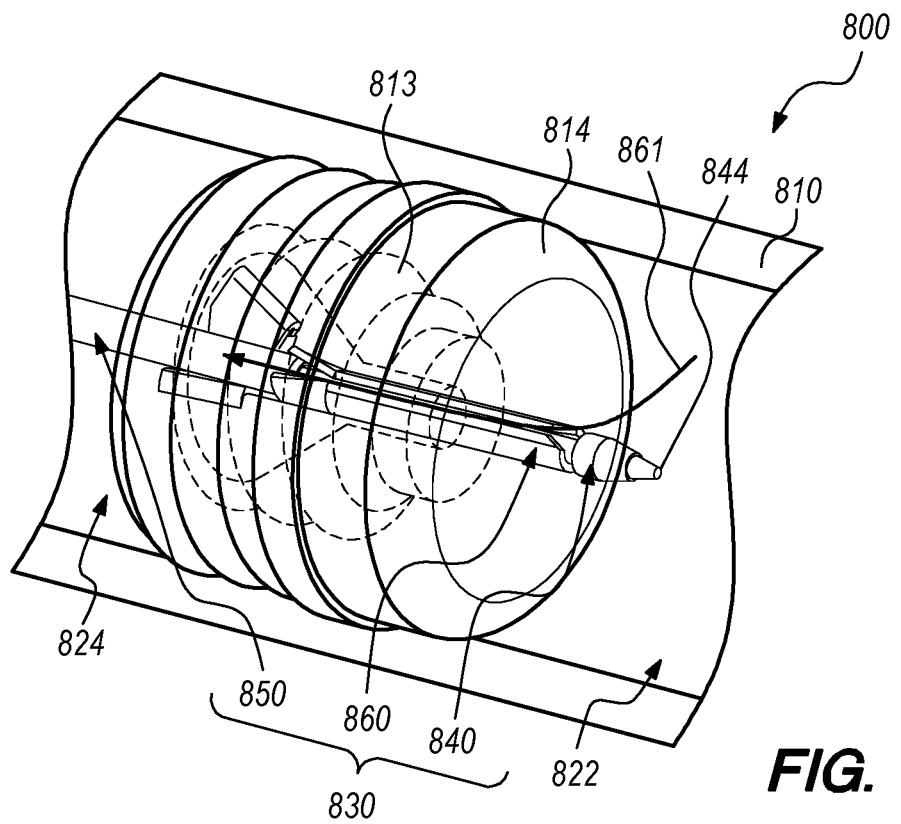

FIG. 17 depicts a dual chamber injection system 800 in a transfer configuration according to some embodiments. In the transfer configuration, the geometric feature 844 has pierced the distal stopper member 814 in response to a distally directed force applied to the distal stopper member 814 (e.g., originally applied through the plunger member 816, the proximal stopper member 812, and an incompressible fluid in the proximal drug chamber 822). An amount of distally directed force required to drive the geometric feature 844 through the distal stopper member 814 may be approximately 3 lbf to approximately 5 lbf. In the transfer configuration, a proximal end of the transfer member 860 is disposed in the proximal drug chamber 822. The transfer member 860 defines a fluid passage (e.g., trench) 861 on top of the annularly recessed portion 848 (see FIGS. 10 and 14) of the penetrating member 840. In the transfer configuration, the fluid passage 861 is a fluid flow path between the proximal and distal drug chambers 822, 824. Accordingly, with increased pressure in the proximal drug chamber 822, which may be provided by distal movement of the plunger member 816 and the proximal stopper member 812 coupled thereto, fluid is transferred from the proximal drug chamber 822 to the distal drug chamber 824. The transfer member 860 also includes chamfered corners and a proximal end thereof configured to reduce resistance to liquid flow through the fluid passage 861.

In the transfer configuration, the user may apply distally directed force to the plunger member 816 to transfer a liquid drug component in the proximal drug chamber 822 to a distal drug chamber 824 to solubilize a powdered drug component therein. The liquid drug component is transferred through the fluid passage 861 formed in the distal stopper member 814 by the transfer member 860 of the fluid conveying assembly 830.

Figure 18:
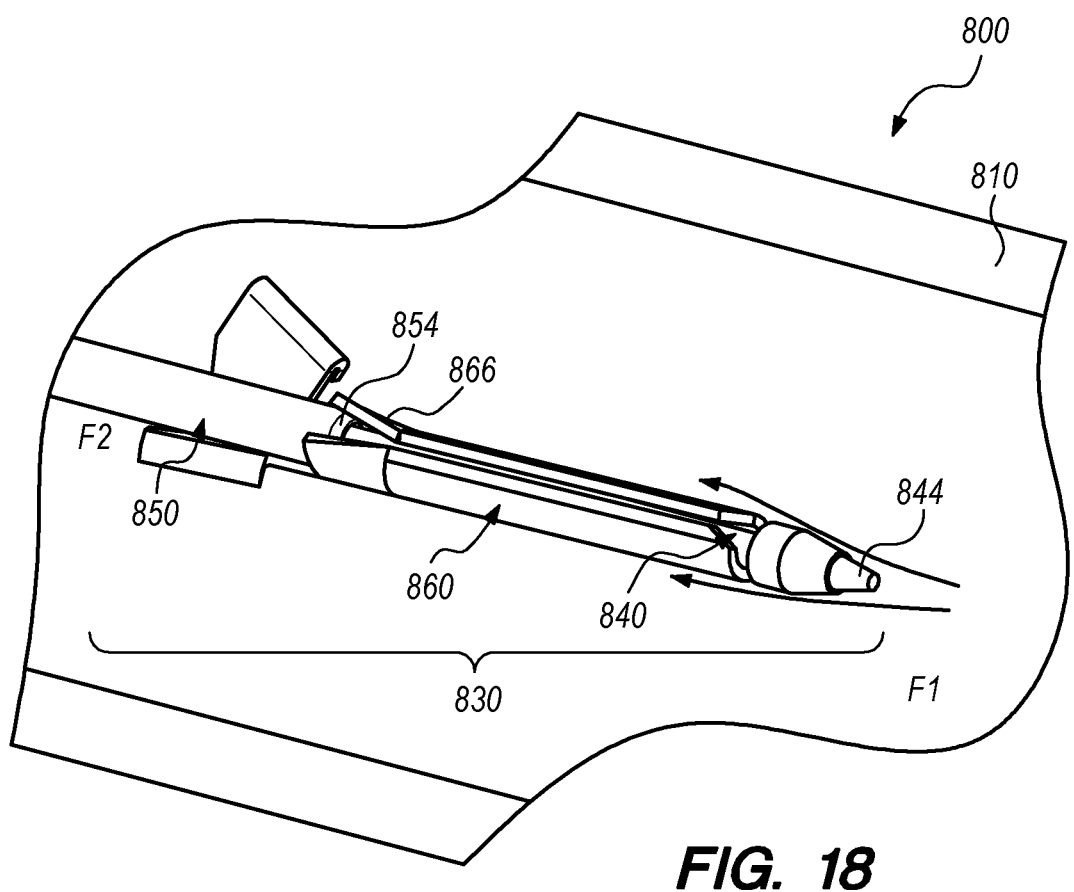

FIG. 18 depicts the forces acting on the transfer member 860 while the fluid conveying assembly 830, led by the geometric feature 844, penetrates completely through the distal stopper member 814 (see FIG. 17) according to some embodiments. During insertion of the fluid conveying assembly 830 through the distal stopper member 814 the friction of the distal stopper member material exerts a distally directed force F1 on the transfer member 860. However the distally directed force F1 is countered by a reaction force F2 generated by the interference between the distal shoulder 854 and the funnel 866 on the distal end of the transfer member 860. The balancing of forces F1 and F2 results in the transfer member 860 remaining in the annularly recessed portion 848 (see FIGS. 10 and 14) of the penetrating member 840 as the fluid conveying assembly 830 penetrates the distal stopper member 814. The distal stopper member 814 and the geometric feature 844 are configured such that the amount of force that the distal stopper member 814 exerts on the geometric feature 844 necessary to cause the fluid conveying assembly 830 to penetrate the distal stopper member 814 is between approximately 3 lbf to approximately 5 lbf.

Figure 19:
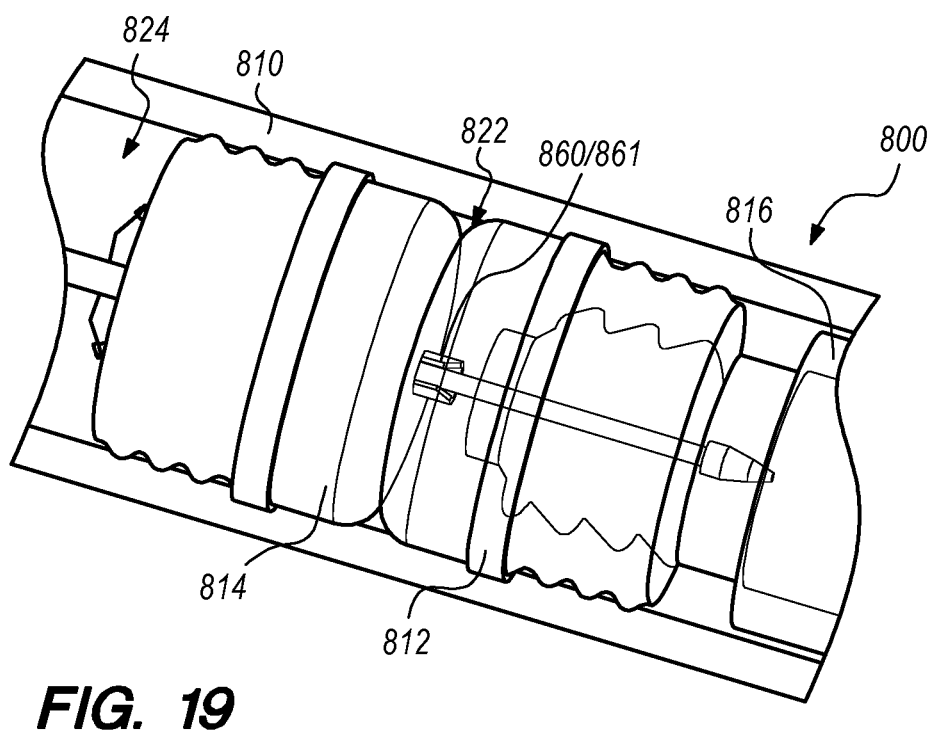

FIG. 19 depicts a dual chamber injection system 800 after the dual chamber injection system 800 has reached a mixed configuration according to some embodiments. In the mixed configuration, the proximal stopper member 812 has advanced distally such that the proximal and distal stopper members 812, 814 are in contact with each other, thereby substantially collapsing the proximal drug chamber 822. In the mixed configuration, any liquid drug component in the proximal drug chamber 822 has been transferred through the fluid passage 861 formed in the distal stopper member 814 by the transfer member 860 to the distal drug chamber 824. At that point, the dual chamber injection system 800 may be agitated (e.g., by inverting) to mix the drug components in the distal drug chamber 824. After mixing the drug components, the multi-component injectable drug is ready for delivery/injection.

After the dual chamber injection system 800 has reached the mixed configuration, further application of distally directed force at the plunger member 816 pushes the proximal and distal stopper members 812, 814 distally relative to the penetrating member 840 (see FIG. 18). Initially, the distally directed force moves the proximal and distal stopper members 812, 814 distally relative to the transfer member 860. However, with distal movement of the distal stopper member 814 relative to the transfer member 860, the radially extending members/wings 868 abut an inner surface of the guide/funnel 813 thereby preventing further distal movement of the distal stopper member 814 (see FIGS. 19 and 20) relative to the transfer member 860. The interference between the radially extending members/wings 868 and the guide/funnel 813 allow additional force to be applied to the transfer member 860 by the guide/funnel 813. This additional force (i.e., approximately 6 lbf to approximately 10 lbf) is sufficient to transform the transfer member 860 from the closed configuration (see FIG. 18) to the open configuration depicted in FIG. 20. When the amount of distally directed force reaches approximately 6 lbf to approximately 10 lbf, the distal shoulder 854 formed by the proximal end of the distal exit tube 850 wedges against the funnel 866 at the distal end of the transfer member 860, thereby opening the tubular transfer member 860. When the transfer member 860 is wedged open, it transforms from its closed configuration to its open configuration.

With the transfer member 860 and the open configuration, the distal exit tube 850 and the penetrating member 840 coupled thereto can move proximally relative to the proximal and distal stopper members 812, 814. With such distal movement, the penetrating member 840 penetrates the proximal stopper member 812. Because the transfer member 860 penetrates only the distal stopper member 814 and not the proximal stopper member 812, there is no fluid leak path into the plunger member 816. The proximal stopper member 812 will seal around the penetrating member 840 and the distal exit tube 850 as they penetrate the proximal stopper member 812.

Figure 20:
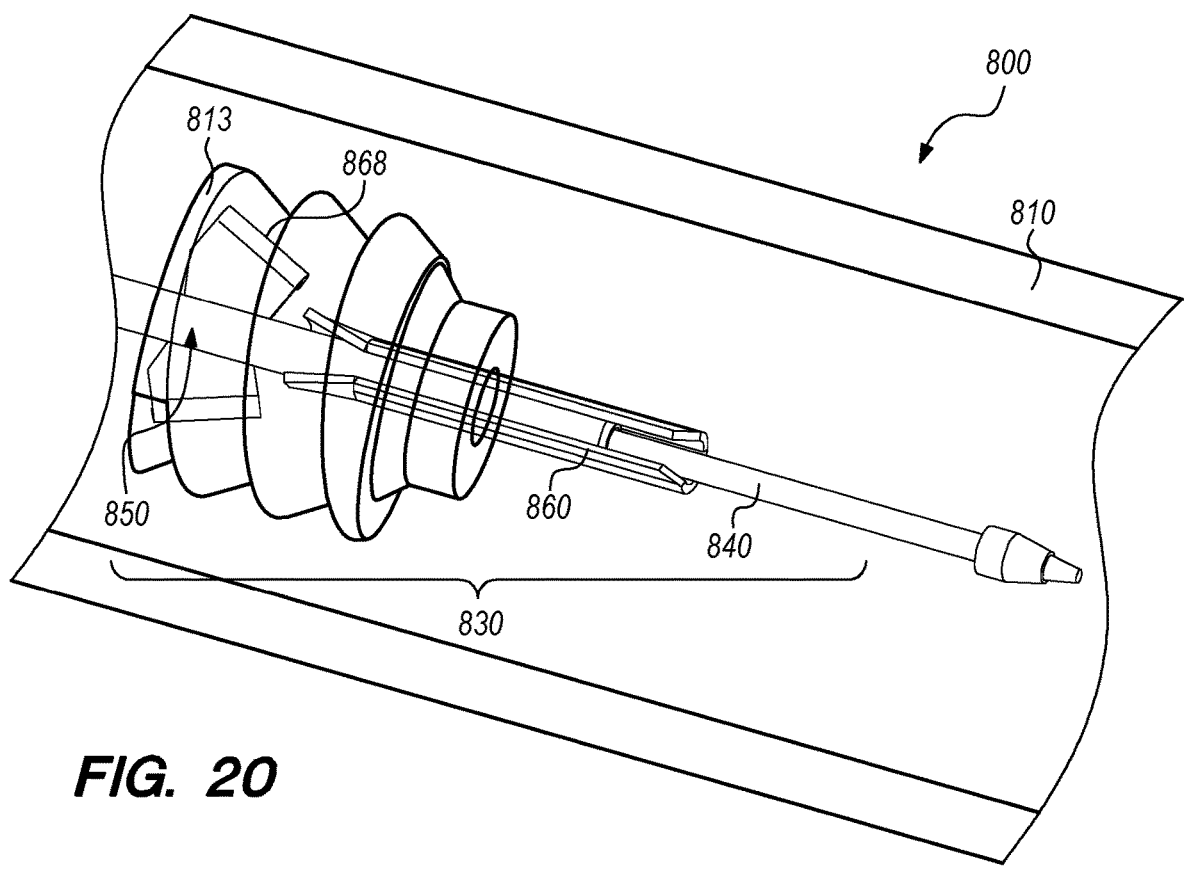

FIG. 20 depicts the relative positions of the fluid conveying assembly 830 and the guide/funnel 813 in the distal stopper member (not shown for clarity) after a dual chamber injection system 800 has reached the mixed configuration and the a transfer member 860 has reached an open configuration according to some embodiments. The radially extending members/wings 868 of the transfer member 860 interfere with the guide/funnel 813 to prevent distal movement of the guide/funnel 813 and the distal stopper member 814 relative to the transfer member 860.

Figure 21A:
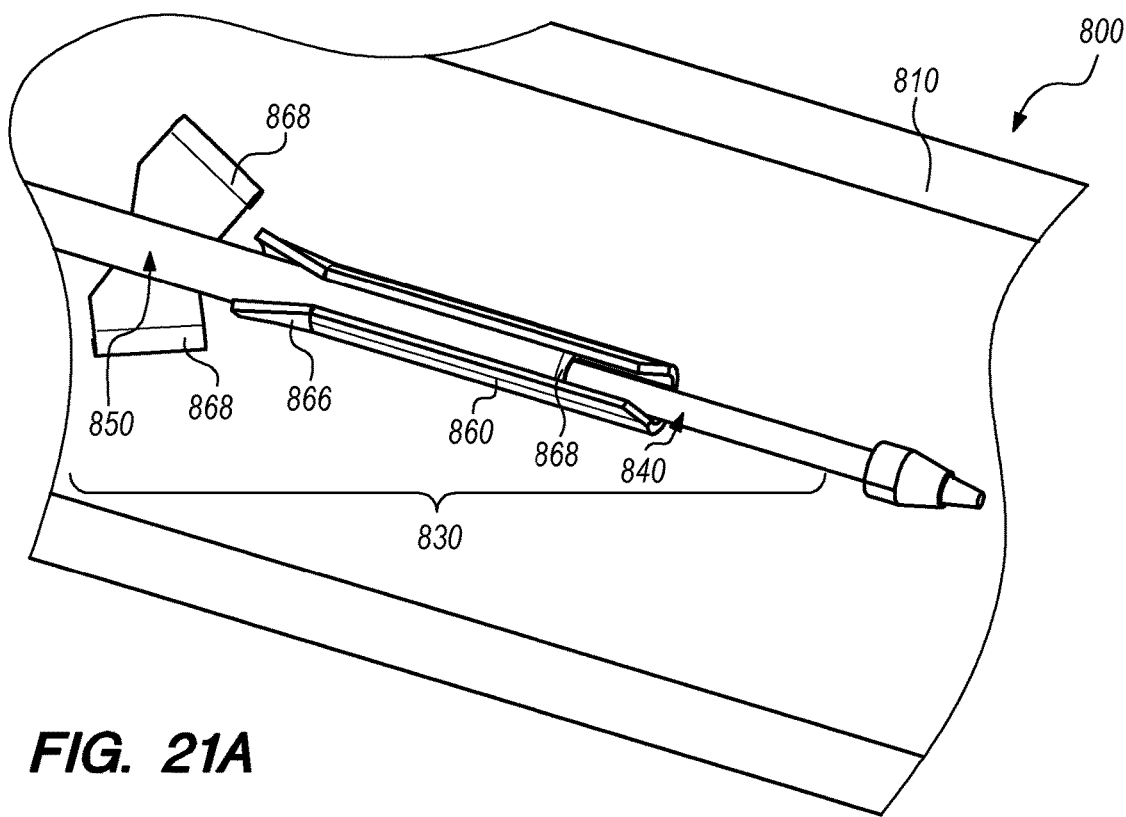

FIG. 21A depicts a fluid conveying assembly 830 with a transfer member 860 in an open configuration according to some embodiments. The guide/funnel 813 and the distal stopper member are omitted for clarity. The dual chamber injection system 800 has moved beyond the mixed configuration by ejecting some of the mixed multi-component injectable from the dual chamber injection system 800. As described above, the distal shoulder 868 formed by the proximal end of the distal exit tube 850 wedges the transfer member 860 into the open configuration starting from the funnel 866 at the distal end of the transfer member 860. With the transfer member 860 in the open configuration, the transfer member 860 can move proximally relative to the distal exit tube 850.

Figure 21B:
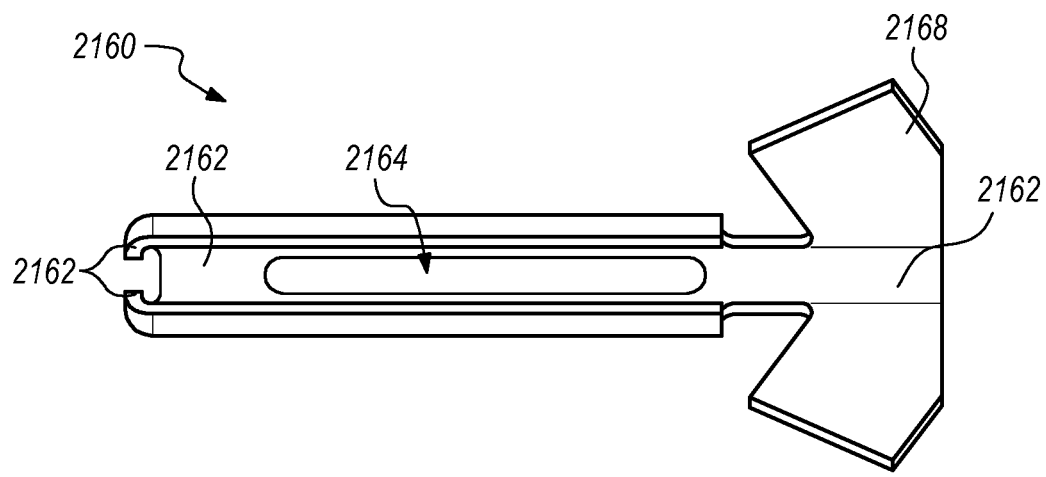
FIGS. 21B to 21E depict a fluid conveying assembly and components thereof for use in dual chamber injection systems according to some embodiments.
Figure 21C:
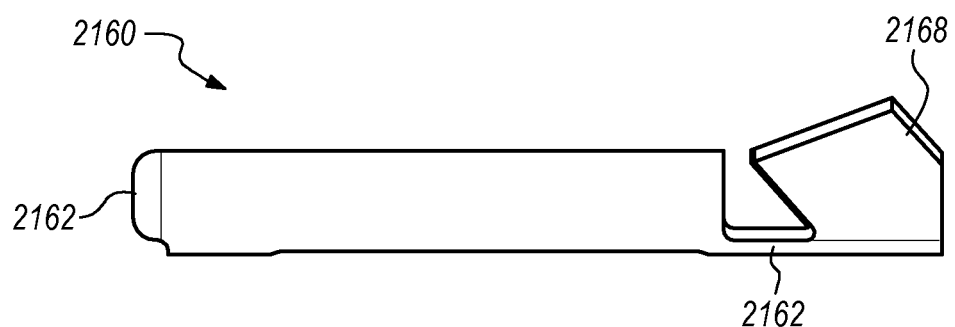
Figure 21D:
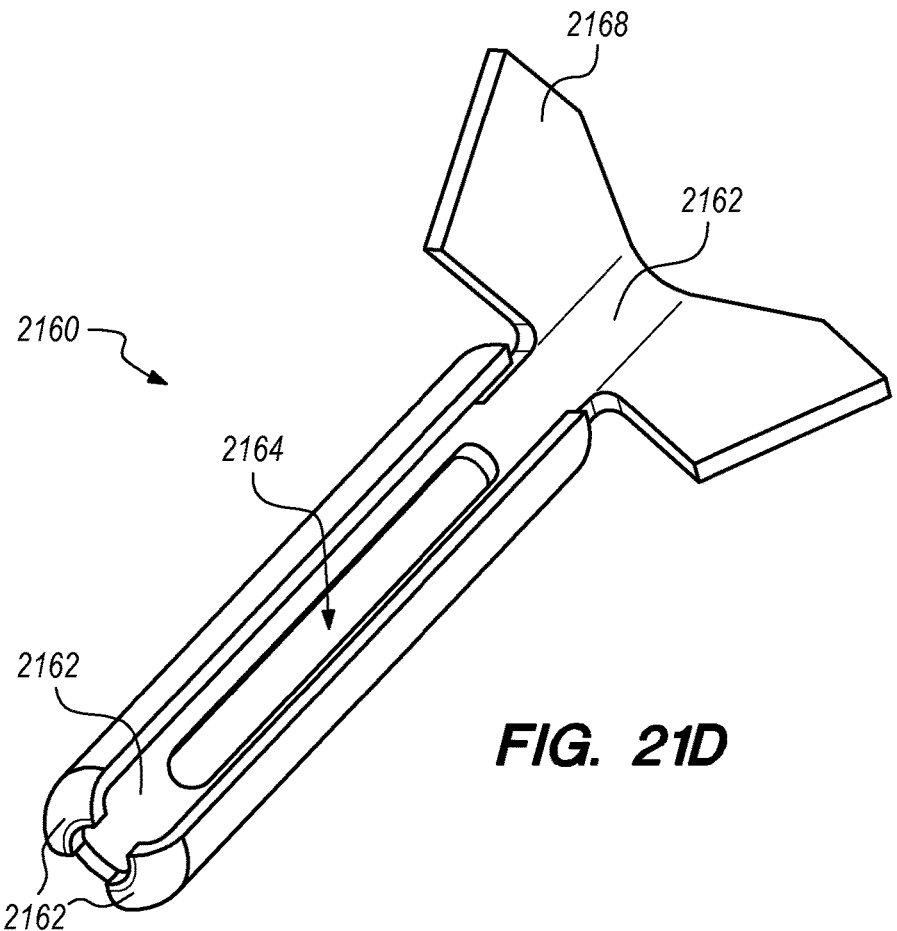
Figure 21E:
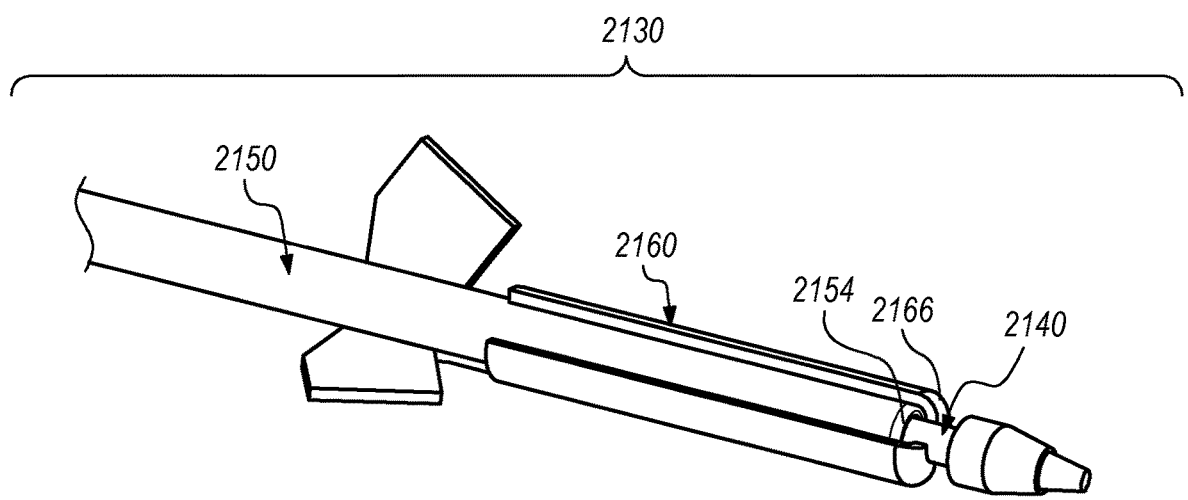

FIGS. 21B to 21E depict a fluid conveying assembly 2130 (see FIG. 21E) according to some embodiments. The fluid conveying assembly 2130 includes a penetrating member 2140, a distal exit tube 2150, and a transfer member 2160. The penetrating member 2140 and the distal exit tube 2150 are similar to the penetrating member 840 and the distal exit tube 850 depicted in FIGS. 7 to 21A and described above. One difference is that the penetrating member 2140 in FIG. 21E is shorter than the penetrating member 840 depicted in FIGS. 7 to 21A. The shorter length of the penetrating member is to accommodate the transfer member 2160, which is described below.

FIGS. 21B to 21D depict the transfer member 2160 in a top, side, and perspective views. The transfer member 2160 in FIGS. 21B to 21D is similar to the transfer member 860 in FIG. 11. For instance, the transfer member 2160 has plastic hinges 2162, a longitudinal opening 2164, and a pair of radially extending member/wings 2168. These components of the transfer member 2160 are almost identical to the corresponding components in transfer member 860 depicted and described above. One difference between the transfer members 2160, 860 is that the transfer member 2160 depicted in FIGS. 21B to 21D does not have a funnel/guide such at a distal end thereof as the funnel/guide 866 at the distal end of the transfer member 860 depicted in FIG. 11. Another difference is that the transfer member 2160 depicted in FIGS. 21B to 21D has a pair of detents 2166 at a proximal end thereof configured to interfere with the distal shoulder 2154 formed at a proximal end of the distal exit tube 2150 (see FIG. 21E).

The detents 2166 are configured to prevent proximal movement of the distal exit tube 2150 and the penetrating member 2140 coupled thereto relative to the transfer member 2160 when the transfer member 2160 is in the closed configuration depicted in FIGS. 21A to 21E. The transfer member 2160 is configured to remain in its closed configuration until a predetermined amount of distally directed force (e.g., approximately 6 lbf to approximately 10 lbf) is applied to the transfer member 2160. In some embodiments when the predetermined amount of distally directed force is applied to the transfer member 2160, the distal shoulder 2154 pushes past the detents 2162, thereby prying open the transfer member 2160 and converting it to an open configuration. With the transfer member 2160 in its open configuration the distal exit tube 2150 and the penetrating member 2140 coupled thereto are free to move distally relative to the transfer member 2160.

As described above with reference to the transfer configuration depicted in FIG. 17, the amount of force required to drive the geometric feature 844 through the distal stopper member 814 may be approximately 3 lbf to approximately 5 lbf. After the dual chamber injection system 800 is in the transfer configuration, additional force drives fluid from the proximal chamber 822 to the distal chamber 824 (see FIG. 17). After most of the fluid has transferred from the proximal chamber 822 to the distal chamber 824, the dual chamber injection system 800 is in the mixed configuration. With further application of distally directed force as shown in FIGS. 19 and 20, additional distally directed force applied to the plunger member 816 will move the distal stopper member 814 distally relative to the transfer member 860 until the radially extending members/wings 868 abut an inner surface of the guide/funnel 813 of the distal stopper member 814. At this point, the interference between the members/wings 868 and the guide/funnel 813 allow more force (e.g., approximately 6 lbf to approximately 10 lbf) to be applied to the distal shoulders 854, 2154 formed by the proximal end of the distal exit tubes 850, 2150, which then wedges the transfer members 860, 2160 into their respective open configurations. As such, the fluid conveying assemblies 830, 2130 depicted in FIGS. 8 to 21E facilitates piercing of the distal stopper member 814 to transform the dual chamber injection system 800 from the transport configuration depicted in FIG. 16 to the transfer configuration depicted in FIG. 17 with the application of a smaller (e.g., approximately 3 lbf to approximately 5 lbf) of force. The fluid conveying assembly 830 also facilitates transfer of a fluid from the proximal drug chamber 822 to the distal drug chamber 824 during while the dual chamber injection system 800 is in the transfer configuration depicted in FIG. 17. The fluid conveying assembly 830 further facilitates wedges open of the transfer member 860 with the application of a larger (e.g., approximately 6 lbf to approximately 10 lbf) of force to transform the transfer member 860 from its closed configuration to its open configuration.

Accordingly, the fluid conveying assembly 830 facilitates increased control during transfer of the fluid from the proximal drug chamber 822 to the distal drug chamber 824, mixing of the fluid with a second drug component in the distal drug chamber 824, and ejection of the mixed multi-component injectable from the dual chamber injection system 800. The fluid conveying assemblies 830, 2130 depicted in FIGS. 8 to 21E and described above may be used with off-the-shelf components such as stopper members, syringe bodies, cartridge bodies, and Luer connectors. The fluid conveying may also be used with safety needle retraction components such as the plunger members and needle hubs described in U.S. Utility patent application Ser. No. 14/696, 342, which was previously incorporated by reference herein.

While specific amounts of force are described above, the fluid conveying assembly 830 can be modified to vary the amount of force needed to penetrate the distal stopper member 814, to transfer the fluid from the proximal drug chamber 822 to the distal drug chamber 824, and to eject the mixed multi-component injectable. Varying the amounts of force needed to accomplish various functions of the dual chamber injection system 800 provides increased control of system 800.

Figure 22:
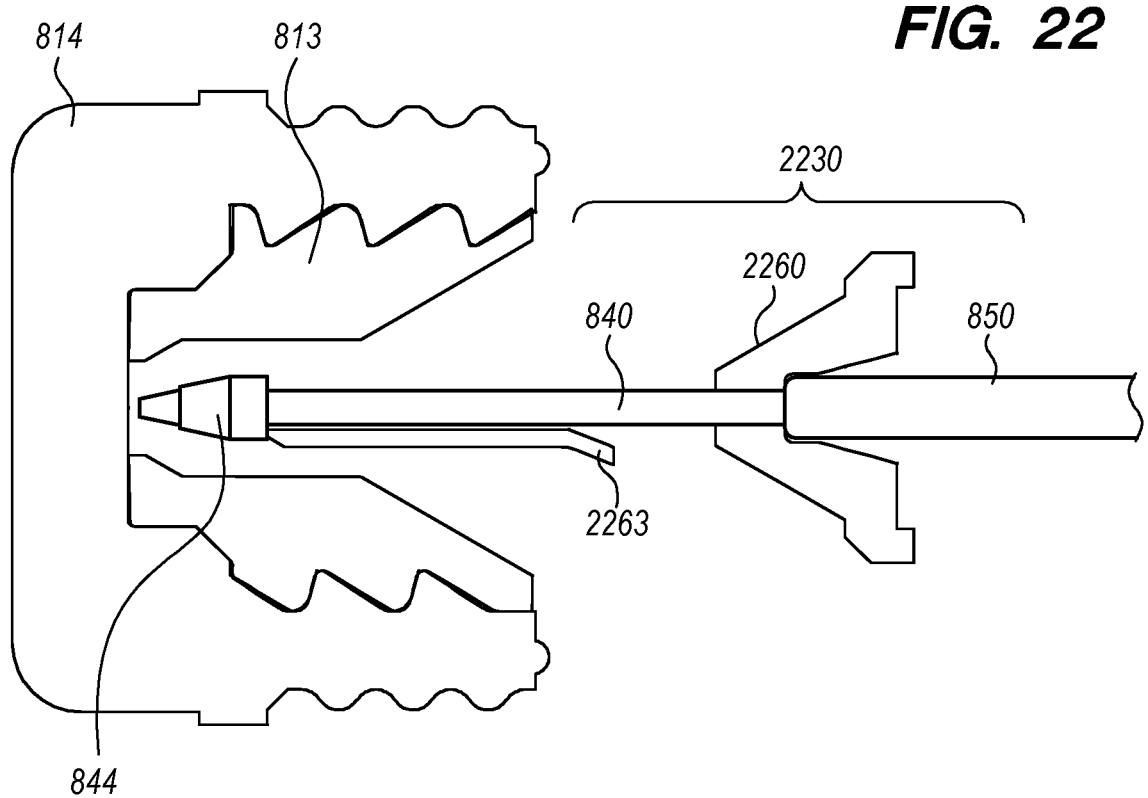
FIGS. 22 to 29H depict a fluid conveying assembly and components thereof for use in dual chamber injection systems according to some embodiments.

Exemplary Fluid Transfer Assembly for Dual Chamber Safe Injection Systems with Polymer Transfer Member FIG. 22 depicts a fluid transfer assembly 2230 and a distal stopper member 814 for use in a dual chamber injection system according to some embodiments. Other components of the dual chamber injection system can be identical to those in the dual chamber injection system 800 depicted in FIG. 8 and described above. These other components may be off-the-shelf components such as stopper members, syringe bodies, cartridge bodies, and Luer connectors. These other components may also be safety needle retraction components such as the plunger members and needle hubs described in U.S. Utility patent application Ser. No. 14/696, 342, which was previously incorporated by reference herein.

The fluid transfer assembly 2230 depicted in FIG. 22 includes a penetrating member 840 and a distal exit tube 850. Both of these components are identical to those depicted in FIGS. 8 to 21E and described above. The difference between the fluid transfer assembly 2230 and the fluid transfer assembly 830 described above is the transfer member 2260. Unlike the transfer member 860 described above, which is formed from a sheet of metal, the transfer member 2260 is formed from a polymer. In some embodiments, the transfer member 2260 is molded from polymer.

The fluid transfer assembly 2230 and the distal stopper member 814 and the guide/funnel 813 are in a transport configuration in FIG. 22. In that configuration, a geometric FIG. 844 is disposed in respective centers of the guide/funnel 813 and the distal stopper member 814.

Figure 23:
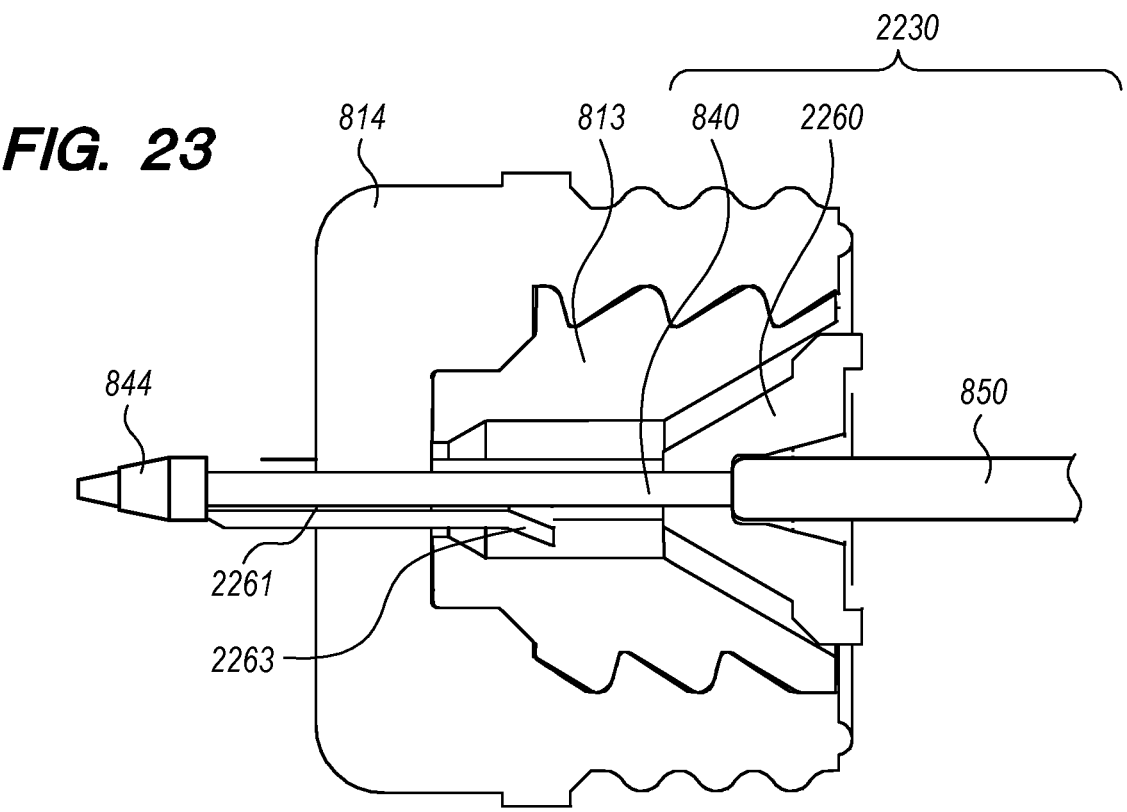

FIG. 23 depicts the fluid transfer assembly 2230 and the distal stopper member 814 in a transfer configuration according to some embodiments. As described above with respect to fluid transfer assembly 830, the fluid transfer assembly 2230 and the distal stopper member 814 are configured such that a predetermined amount of distally directed force (e.g., approximately 3 lbf to approximately 5 lbf) applied to the distal stopper member 814 will cause the geometric FIG. 844 to pierce the distal stopper member 814. In the transfer configuration, the penetrating member 840 and the transfer member 2260 also penetrate the distal stopper member 814. A recess in a longitudinal section of the transfer member 2260 forms a fluid passage (e.g., trench) 2261 through the distal stopper member 814. As described above, after the dual chamber injection system is in the transfer configuration, continued application of distally directed force will drive fluid from a proximal chamber to a distal chamber (not shown).

Figure 24:
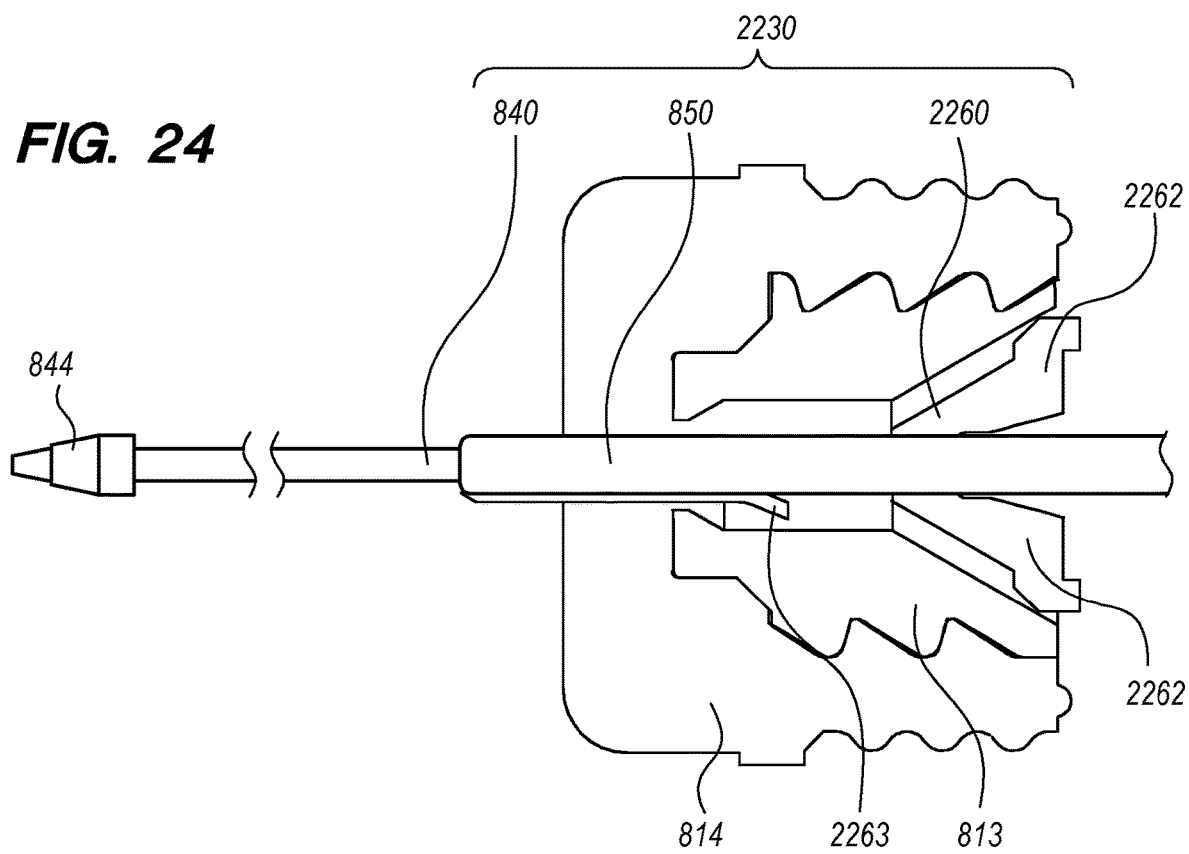

FIG. 24 depicts the fluid transfer assembly 2230 and the distal stopper member 814 after the dual chamber injection system has reached a mixed configuration according to some embodiments. The transfer member 2260 includes a pair of latches 2262, which prevent movement of the distal exit tube 850 proximally past the latches 2262 when the latches 2262 are biased in a closed state (see FIGS. 22 and 23). The latches 2262 are actuated when they abut a surface of the guide/funnel 813 and are acted on by a proximal end of the distal exit tube 850. Actuating the latches 2262 transforms the latches 2260 open state allowing the distal exit tube 850 to move proximally past the latches 2262, as shown in FIG. 24. The latches 2262 are configured such that the amount of force applied to the distal stopper member 814 sufficient to actuate the latches 2262 may be approximately 6 lbf to approximately 10 lbf. The transfer member 2260 also includes a funnel 2263 to provide a smoother transition (i.e., minimize force/resistance variation) as the proximal end of the distal exit tube 850 passes through the transfer member 2260.

Figure 25:
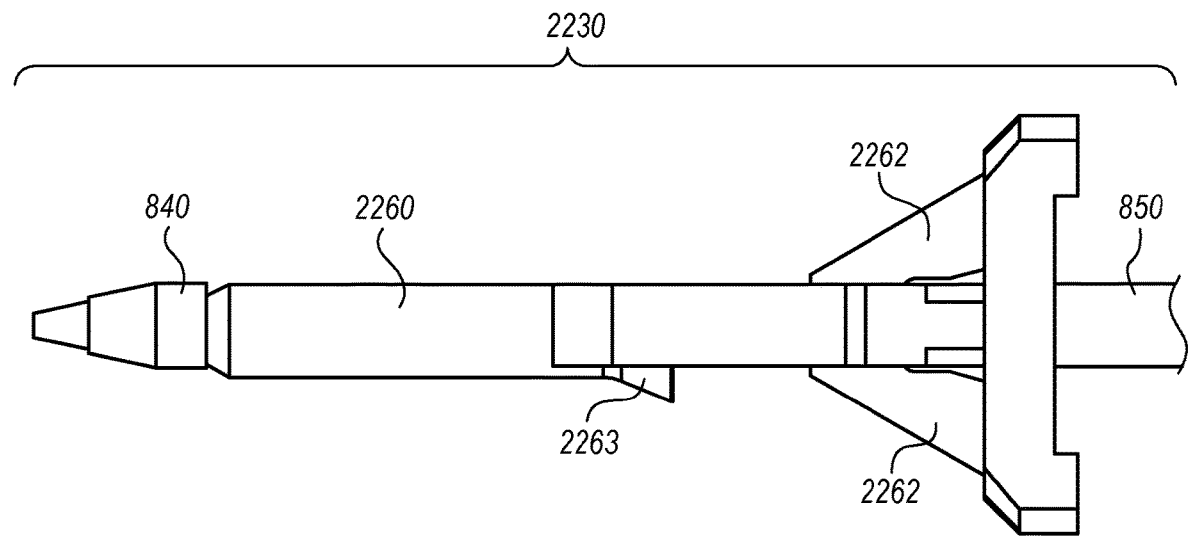
Figure 26:
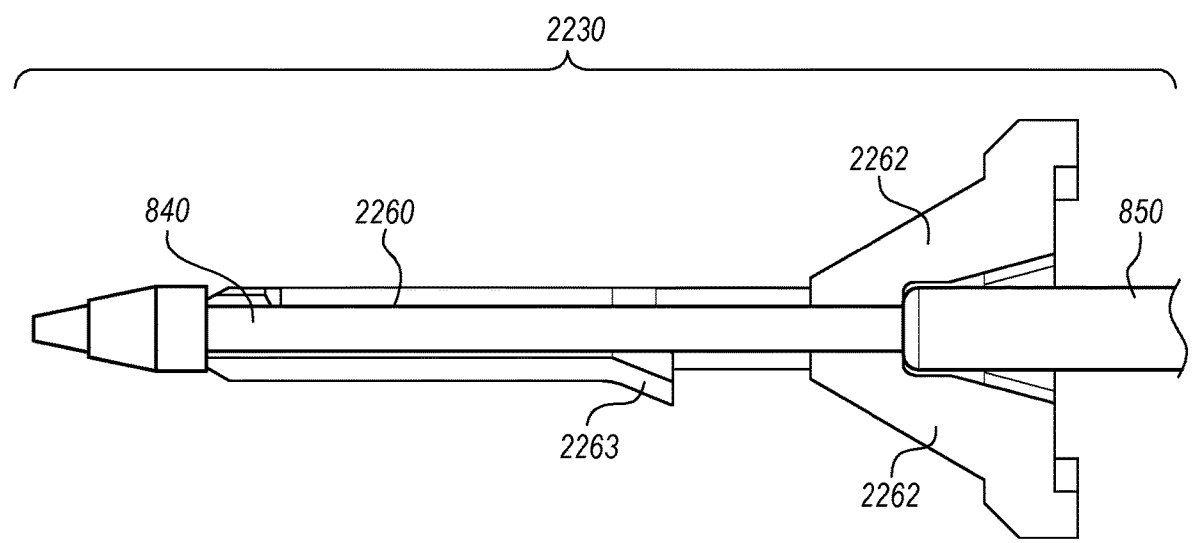
Figure 27:
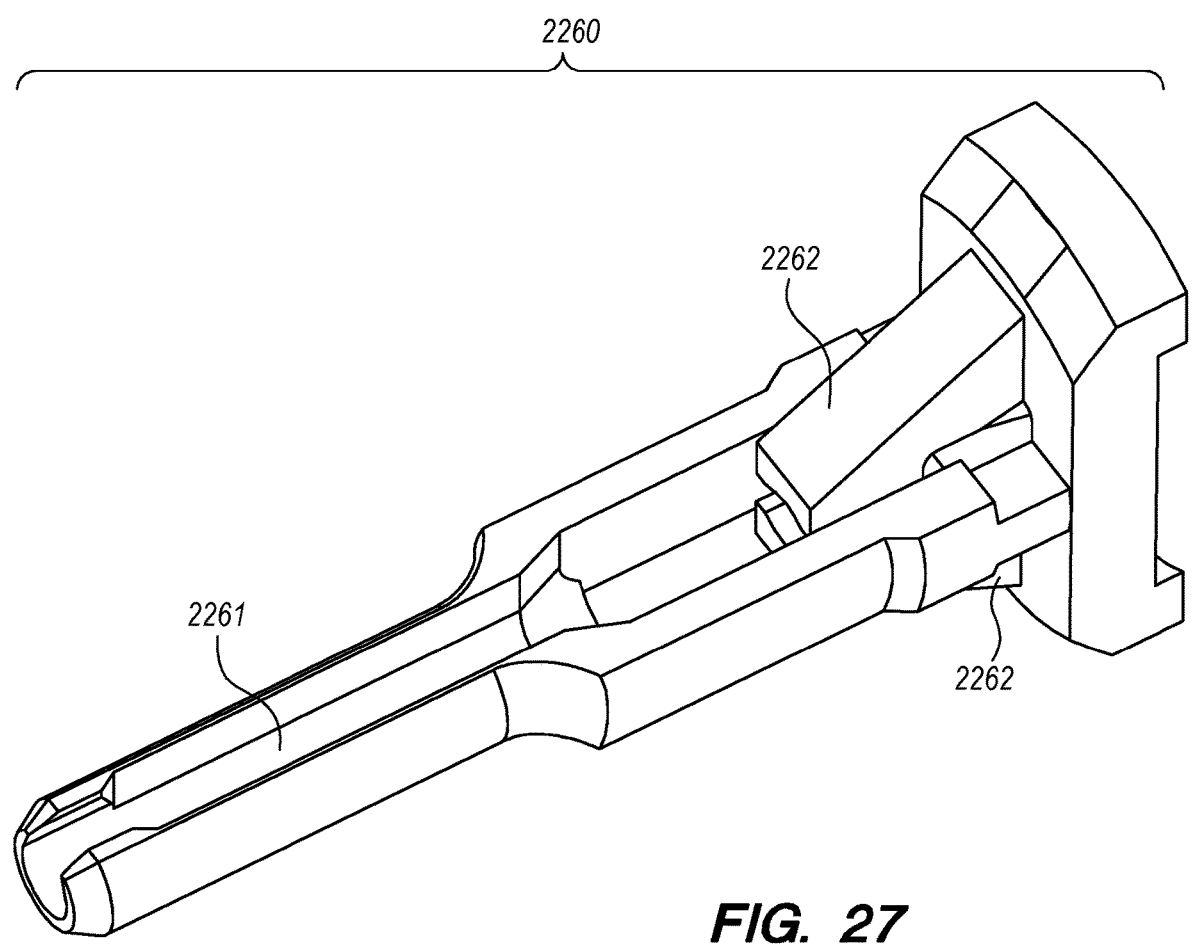

FIGS. 25 to 27 depict a proximal end of a fluid transfer assembly 2230 according to some embodiments. The transfer member 2260 and its latches 2262 are shown in FIGS. 25 and 26. The latches are configured such that they will remain in their biased closed state when the amount of force (e.g., approximately 3 lbf to approximately 5 lbf) for the penetrating member 840 to pierce the distal stopper member is applied. This prevents premature release of the distal exit tube 850 and the penetrating member 840 from the transfer member 2260 until sufficient force (e.g., approximately 6 lbf to approximately 10 lbf) is applied to actuate the latches 2262. Accordingly, the latches 2262 in the fluid transfer assembly 2230 depicted in FIGS. 22 to 27 provide a mechanism of control over the distal stopper penetration, fluid transfer, and fluid ejection steps in multi-component injectable delivery as described above.

Figure 28:
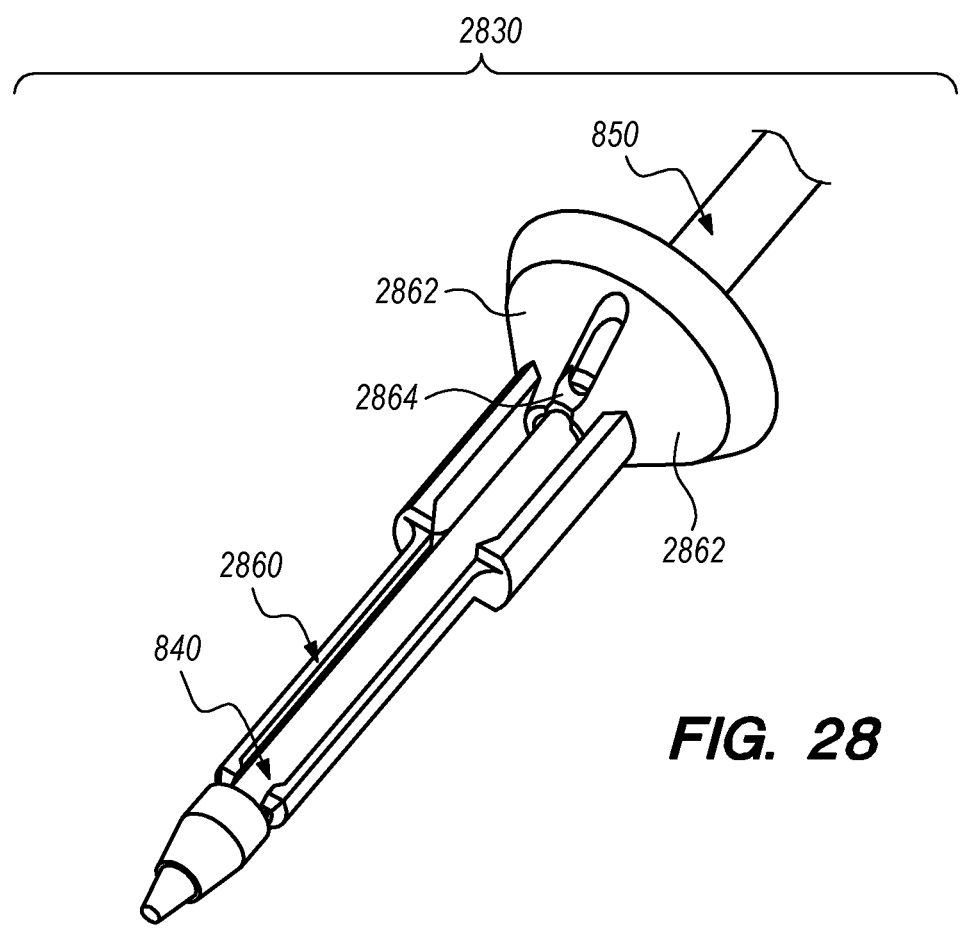
Figure 29A:
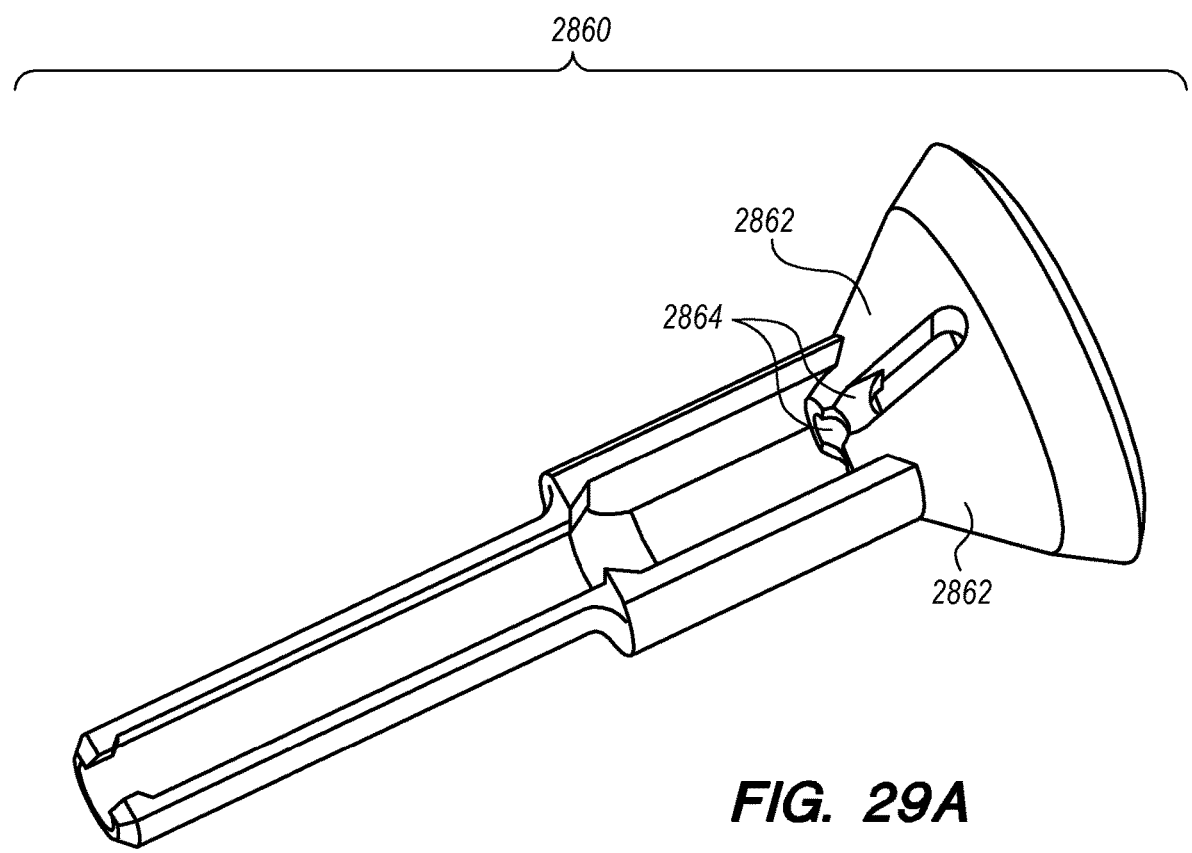

FIG. 28 depicts a fluid transfer assembly 2830 for use in a dual chamber injection system according to some embodiments. The fluid transfer assembly 2830 is similar to the fluid transfer assembly 2230 depicted in FIGS. 22 to 27. The difference between the fluid transfer assemblies 2230, 2830 is the design of the latching mechanisms in the transfer members 2260, 2860. In addition to latches 2862, the transfer member 2860 depicted in FIG. 28 also includes a pair of frangible links 2864 (see FIG. 29A). The frangible links 2864 prevents the latches 2862 from transforming to their opened state until a sufficient force (e.g., approximately 6 lbf to approximately 10 lbf) is applied to the distal stopper member. This additional mechanism provides another control over the distal stopper penetration, fluid transfer, and fluid ejection steps in multi-component injectable delivery as described above.

Figure 29B:
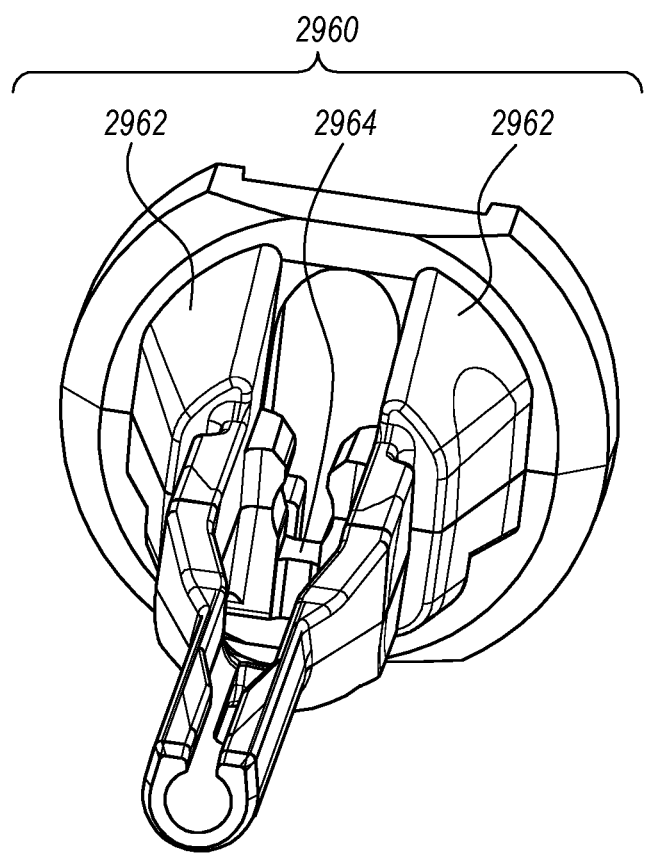
Figure 29C:
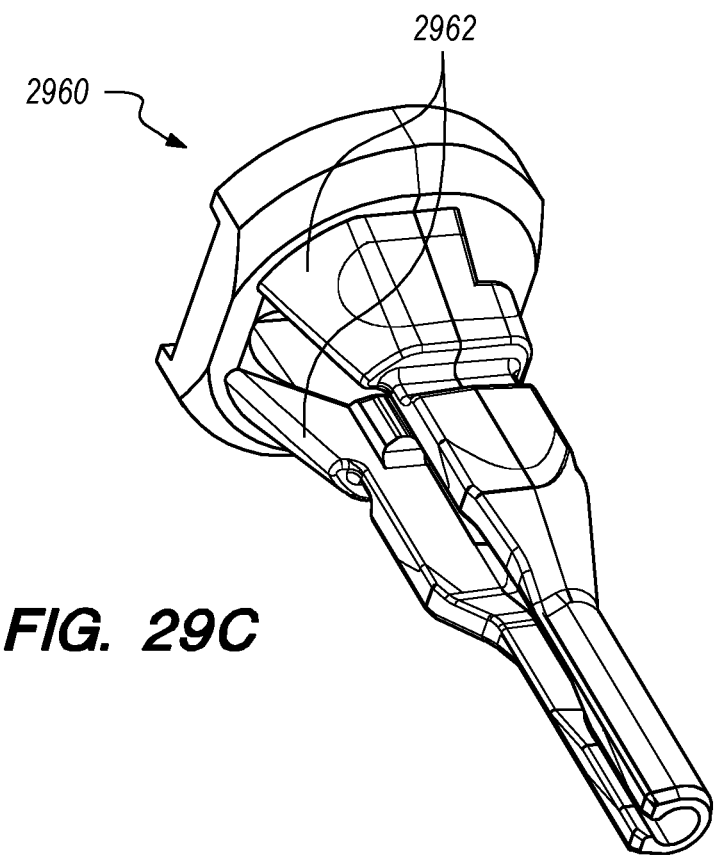
Figure 29D:
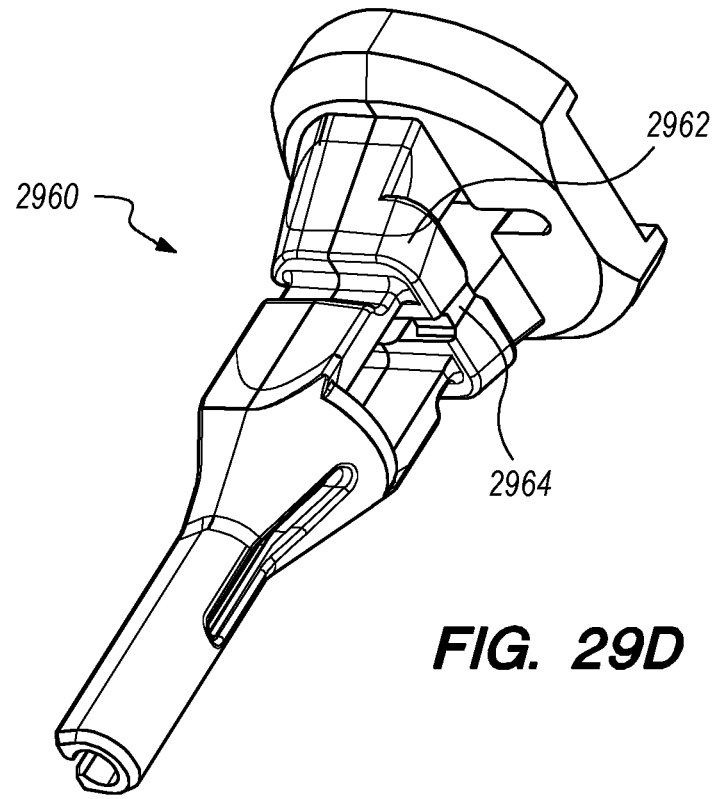
Figure 29E:
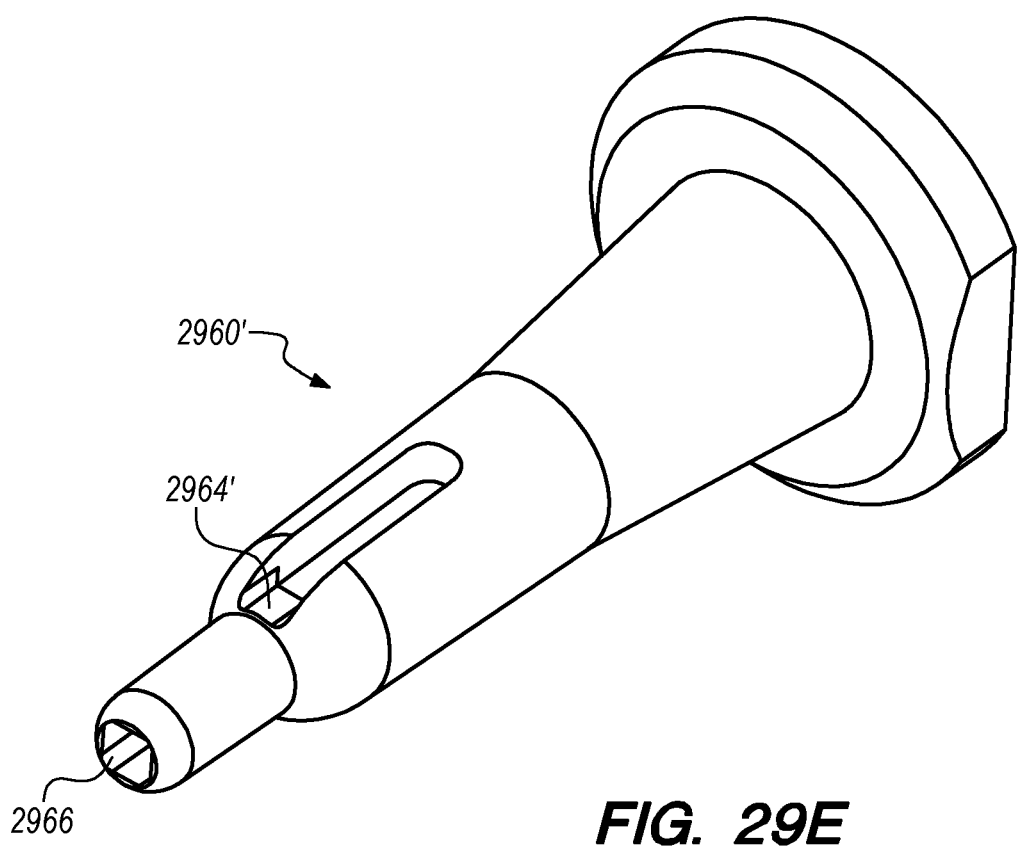
Figure 29F:
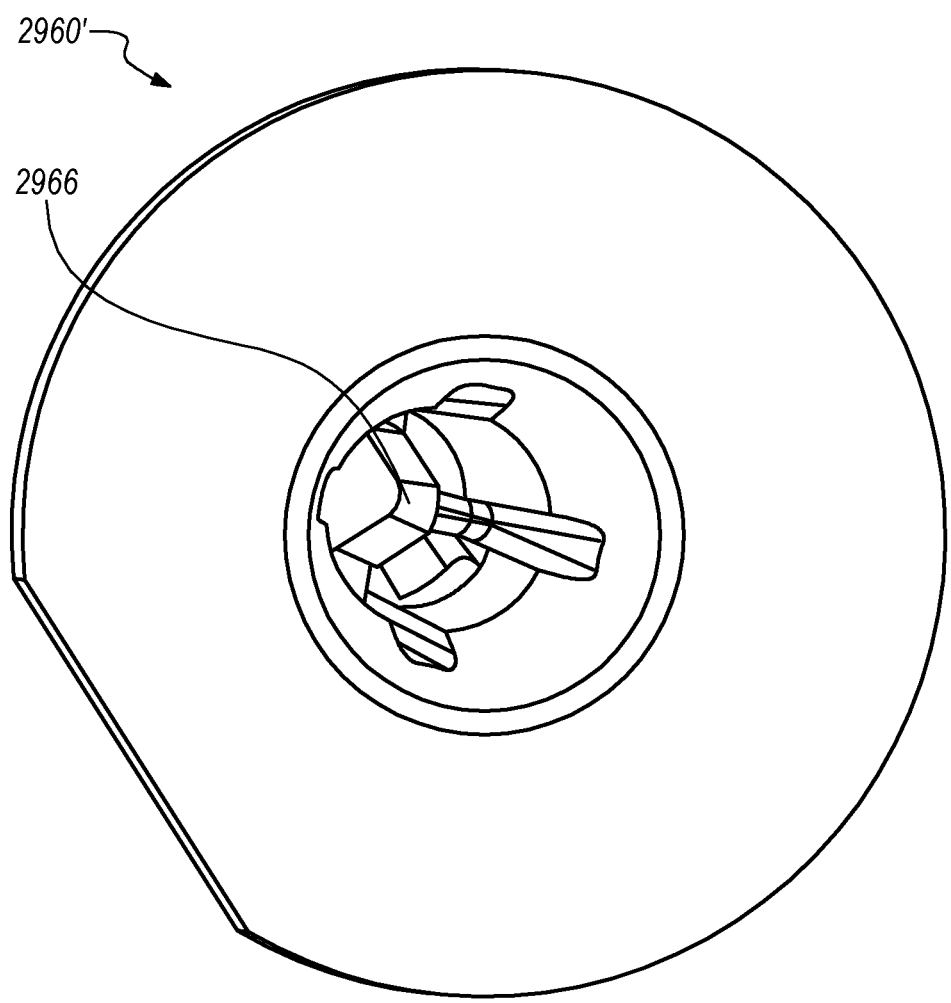
Figure 29G:
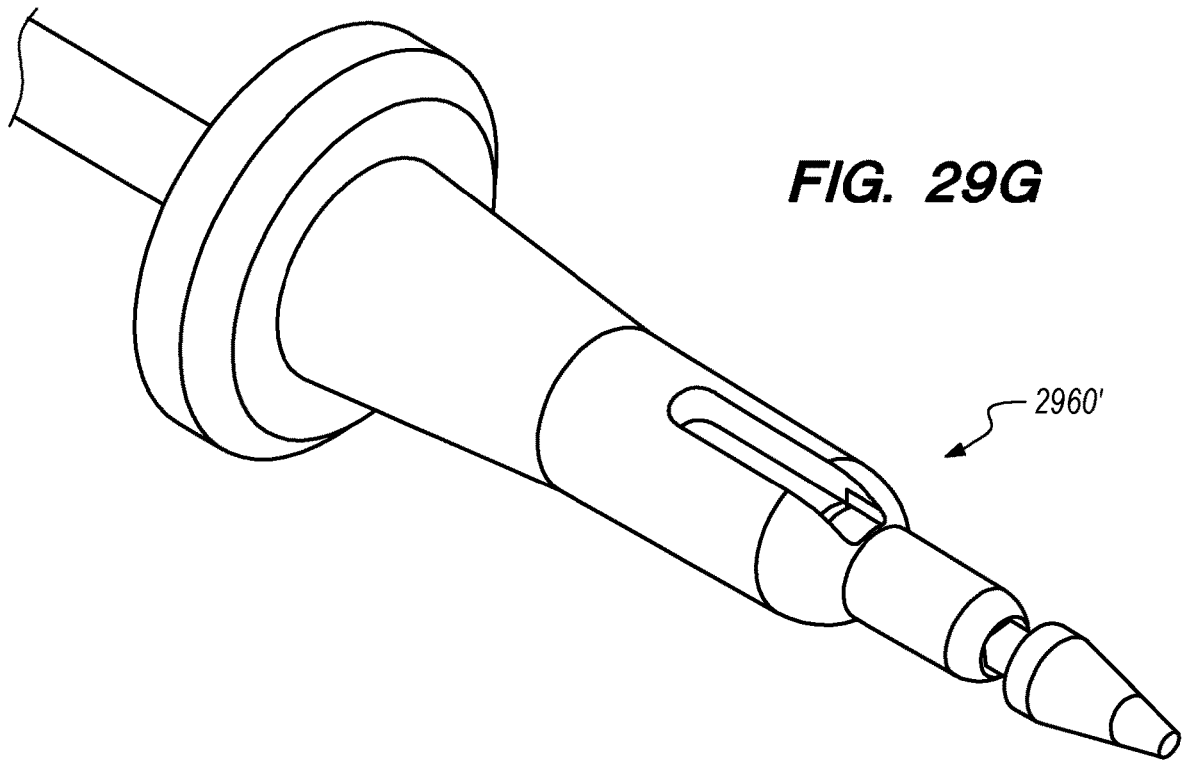
Figure 29H:
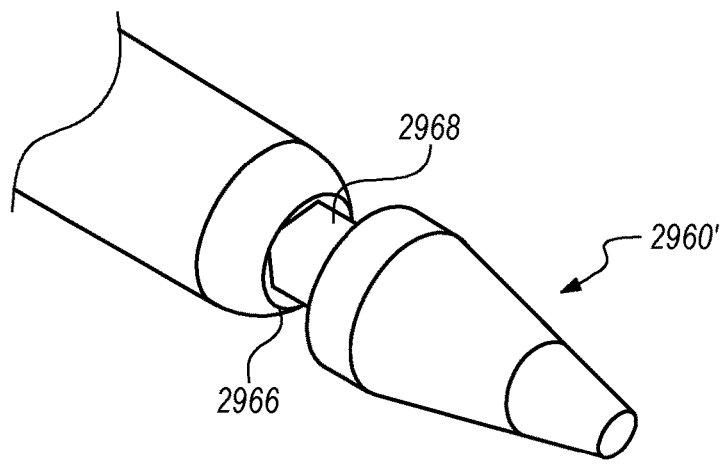

FIGS. 29B to 29D depict a transfer member 2960 for use with a fluid transfer assembly according to some embodiments. The transfer member 2960 is very similar to the transfer member 2860 depicted in FIG. 29A. For instance, the transfer member 2960 depicted in FIGS. 29B to 29D also has a pair of latches 2962 forming a latching mechanism. The difference between the transfer members 2860, 2960 is that the transfer member 2960 depicted in FIGS. 29B to 29D has only one frangible link 2964. The frangible link 2964 prevents the latches 2962 from transforming to their opened state until a sufficient force (e.g., approximately 6 lbf to approximately 10 lbf) is applied to the distal stopper member. This single frangible link 2964 design provides another design option for increased control over the distal stopper penetration, fluid transfer, and fluid ejection steps in multi-component injectable delivery as described above.

FIGS. 29E to 29H depict a transfer member 2960' that includes a distal end, a proximal end, and a frangible link 2964'. The transfer member has interior flow channels 2966 that are define by an interior surface of the transfer member 2960' and may extend through the transfer member 2960' to facilitate fluid flow. The transfer member 2960' may be configured with a single flow channel or a plurality of flow channels. Four flow channels are present in the transfer member 2960' depicted in FIGS. 29E to 29H The interior flow channels 2966 may extend from a proximal end to a distal end of the transfer member 2960'. Alternatively, the interior flow channels 2966 may extend over part of the length of the transfer member 2960'. The proximal end of the transfer member 2960' is configured to surround the proximal end of a penetrating member (2968; see FIG. 29G) circumferentially by forming a complete ring with no breaks. The circumferential nature of the proximal end of the transfer member 2960' increases the radial stiffness of the transfer member 2960', resisting collapsing forces which are generated as the proximal end of the transfer member 2960' penetrates the rubber material of stopper members. The transfer member 2960' may be constructed of a polymer such as COC, COP, Polypropylene, or other medical grade polymer. Installation of the transfer member 2960' onto the penetrating member 2968 may be accomplished by sliding the transfer member 2960' over proximal end of the penetrating member 2968. The proximal end of the transfer member 2960' is configured to expand elastically to allow the proximal end of the penetrating member 2968 to pass through a proximal end opening of the transfer member 2960'. After the proximal end of the penetrating member 2968 passes proximally of the proximal end of the transfer member 2960', the proximal end opening of the transfer member 2960' elastically snaps back to a smaller diameter preventing the transfer member 2960' from being uncoupled from the penetrating member 2968. Upon completion of fluid transfer the user applies a distally directed force to the plunger member, thereby overcoming/breaking the frangible link 2964' to allow the penetrating member 2968 to move longitudinally relative to the transfer member 2960'.

Exemplary Dual Chamber Safe Injection System Conversion Kit

Figure 30:
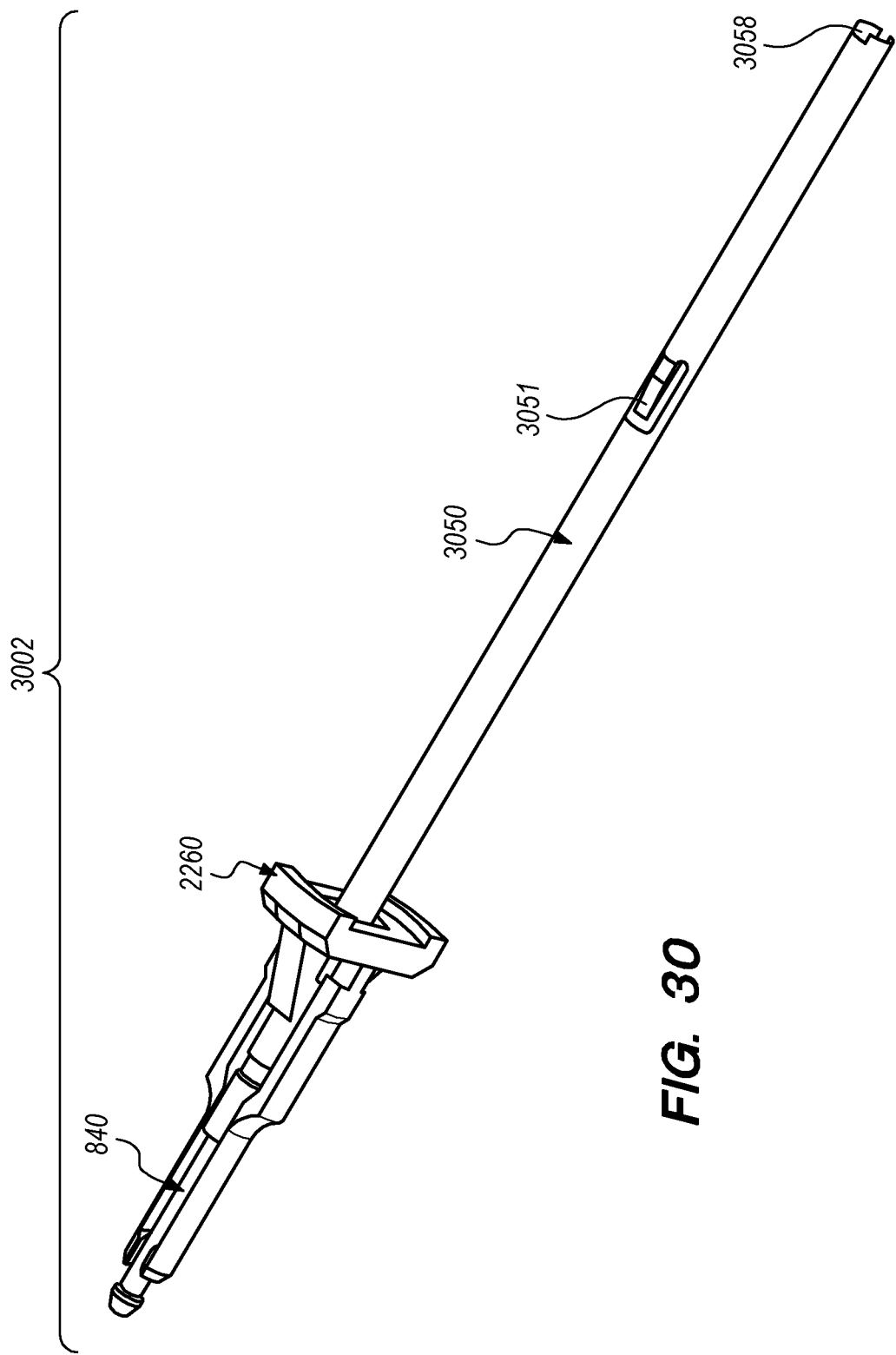
Figure 31:
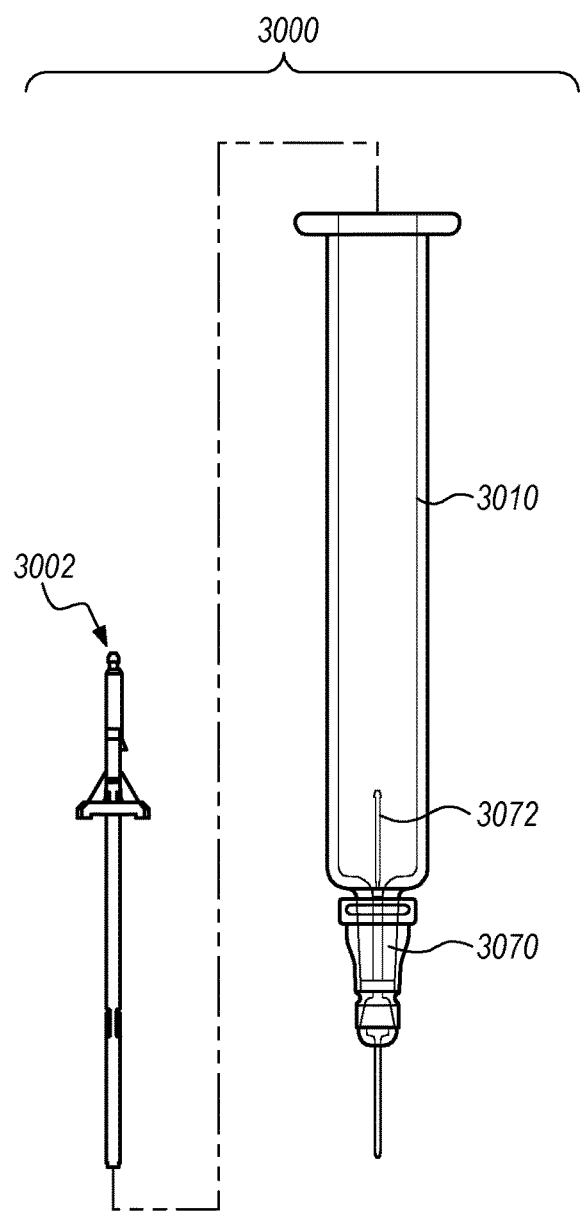

FIG. 30 depicts a fluid transfer assembly 3002, which can form part of a dual chamber injection system conversion kit 3000 (see FIGS. 31 to 34). The fluid transfer assembly 3000 can be used with an off the shelf syringe such as the one shown in FIG. 31 to convert a single chamber injection system to a dual chamber injection system, as shown in described below. The fluid transfer assembly 3002 includes a penetrating member 840, a transfer member 2260, and a distal exit member 3050, which are similar to the corresponding components described above. A latch 3051 in the distal exit member 3050 allows the fluid transfer assembly 3002 to couple to a proximal end of a needle. A split distal and 3058 in the distal exit member 3050 allows the fluid transfer assembly 3002 to couple to a variety of exit modalities (e.g., needles, Luer connectors, tubing).

FIGS. 31 to 34 depict a method for converting a single chamber injection system using the dual chamber injection system conversion kit 3000. In this step depicted in FIG. 31, the fluid transfer assembly 3002 is inserted through a proximal opening of an off the shelf syringe body 3010. The distal exit tube 3050 of the fluid transfer assembly 3002 is inserted over a proximal end of a needle 3072 from a needle hub assembly 3070, thereby coupling the fluid transfer assembly 3002 to the needle 3072 and the needle hub assembly 3070.

Figure 32:
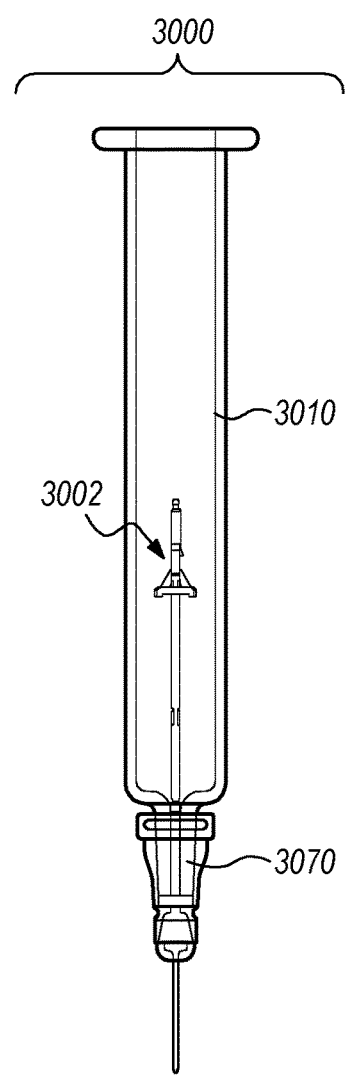

FIG. 32 depicts the result of coupling the fluid transfer assembly 3002 to the needle hub assembly 3070.

FIG. 33 depicts addition of a dry/lyophilized component 3015 of a multi-component injectable into the syringe body 3010 through the proximal opening therein. Then an off-the-shelf distal stopper member 3014 is inserted through the proximal opening in the syringe body 3010 until a proximal end of the penetrating member 840 (see FIG. 30) is disposed in the center of the distal stopper member 3014. Placing the distal stopper member 3014 in the syringe body 3010 and forms the distal drug chamber 3024 in which the dry/lyophilized component 3015 is disposed.

FIG. 34 depicts addition of a liquid/diluent component 3017 of the multi-component injectable into the syringe body 3010 through the proximal opening therein. Then an off-the-shelf proximal stopper member 3012 is inserted through the proximal opening in the syringe body on top of the liquid/diluent component 3017. Placing the proximal stopper member 3012 in the syringe body 3010 and forms the proximal drug chamber 3022 in which the liquid/diluent component 3017 is disposed. Next a finger flange 3080 and a plunger member 3016 are added to the now dual chamber injection system. The needle hub assembly 3070 and the plunger member 3016 may include safety needle retraction components such as the plunger members and needle hubs described in U.S. Utility patent application Ser. No. 14/696, 342, which was previously incorporated by reference herein.

While the fluid transfer assembly 3002 has been described as including a penetrating member 840, a transfer member 2260, and a distal exit member 3050, which are similar to the corresponding components described above, the fluid transfer assembly in the dual chamber safe injection system conversion kit can include various equivalent components, such as the transfer member 860 and/or the distal exit member 850 described above.

Exemplary Finger Flange with Anti-Retraction Feature

Multiple chamber multi-component mixing injection systems may build up pressure in a first chamber when fluid from another one of the chambers is forced into the first chamber. Pressure in the first chamber may push a plunger member backwards/proximally, thereby interfering with the function of the multiple chamber multi-component mixing injection systems.

FIGS. 35 to 43 depict the addition of a one-way ratchet to the dual chamber injection systems described herein (and in the other patent applications incorporated by reference herein). The one-way ratchet enables the plunger member to be moved distally with minimal drag force and prevents the plunger member from moving proximally by the engagement of ratchet teeth onto the outer surface of the plunger member. During the mixing phase of the multi-component injectable preparation air pressure accumulates in the distal chamber as the liquid is transferred. This pressure builds and produces a proximally directed reaction force on the user's thumb. The addition of a toothless ratchet counteracts this reaction force, preventing the plunger member from moving proximally. With the toothless ratchet engaged, the user does not need to continually apply a distally directed force to maintain plunger member position. The ratchet may be toothless, where the plunger member is smooth on the outside surface and the ratchet arms are configured to dig into the plunger member. In this case the position of the plunger member is maintained in infinitely small increments. Alternatively, the ratchet may engage with annular grooves in or threads on the outside surface of the plunger member, providing an incremental position stop. The annular grooves may provide a tactile and/or audible click or feedback to the user that the ratchet is engaged.

Figure 35:
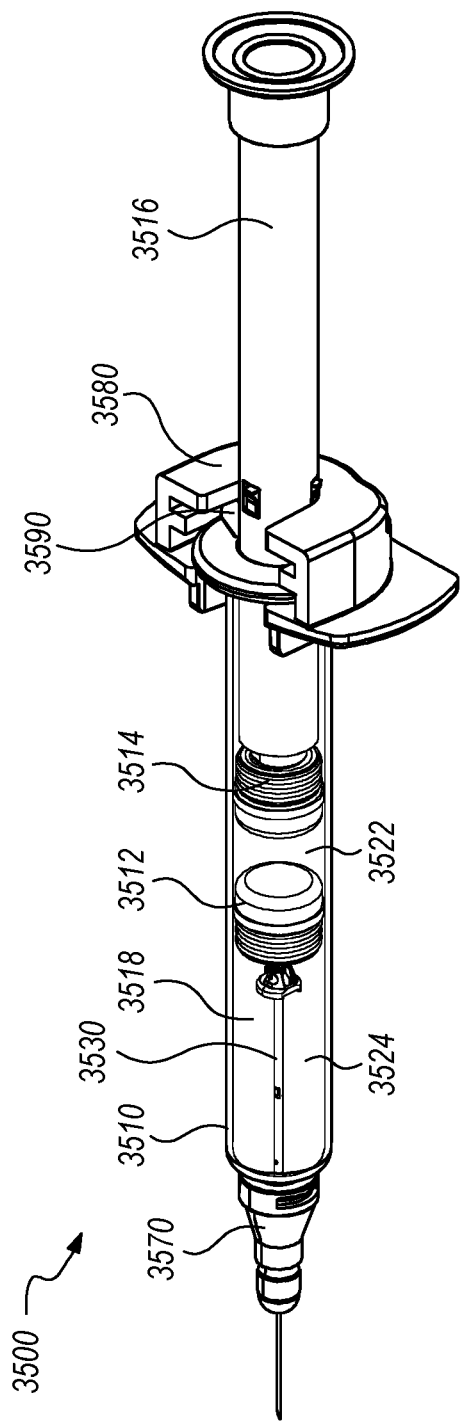
FIGS. 35 to 43 depict an anti-retraction mechanism for use in dual chamber injection systems according to some embodiments.

FIG. 35 depicts a dual chamber injection system 3500 with a finger flange 3580 having an anti-retraction feature 3590 according to some embodiments. The anti-retraction feature 3590 prevents proximal movement of the plunger member 3516 relative to the syringe body 3510, while allowing distal movement. In addition to the syringe body 3510, the plunger member 3516, the finger flange 3580, and the anti-retraction feature 3590, the dual chamber injection system 3500 also includes proximal and distal stopper members 3512, 3514, and a needle hub assembly 3570. The plunger member 3516 is inserted into an interior 3518 of the syringe body 3510 via a proximal opening in the syringe body. The proximal and distal stopper members 3512, 3514 together with the syringe body 3510 define a proximal drug chamber 3522. The distal stopper member 3514 and the syringe body 3510 define a distal drug chamber 3524. The plunger member 3516 may be manually manipulated to insert the proximal stopper member 3512 relative to the syringe body 3510. If a non-compressible fluid is disposed in the proximal drug chamber 3522, inserting the proximal stopper member 3512 also inserts the distal stopper member 3514 relative to the syringe body 3510.

Figure 36:
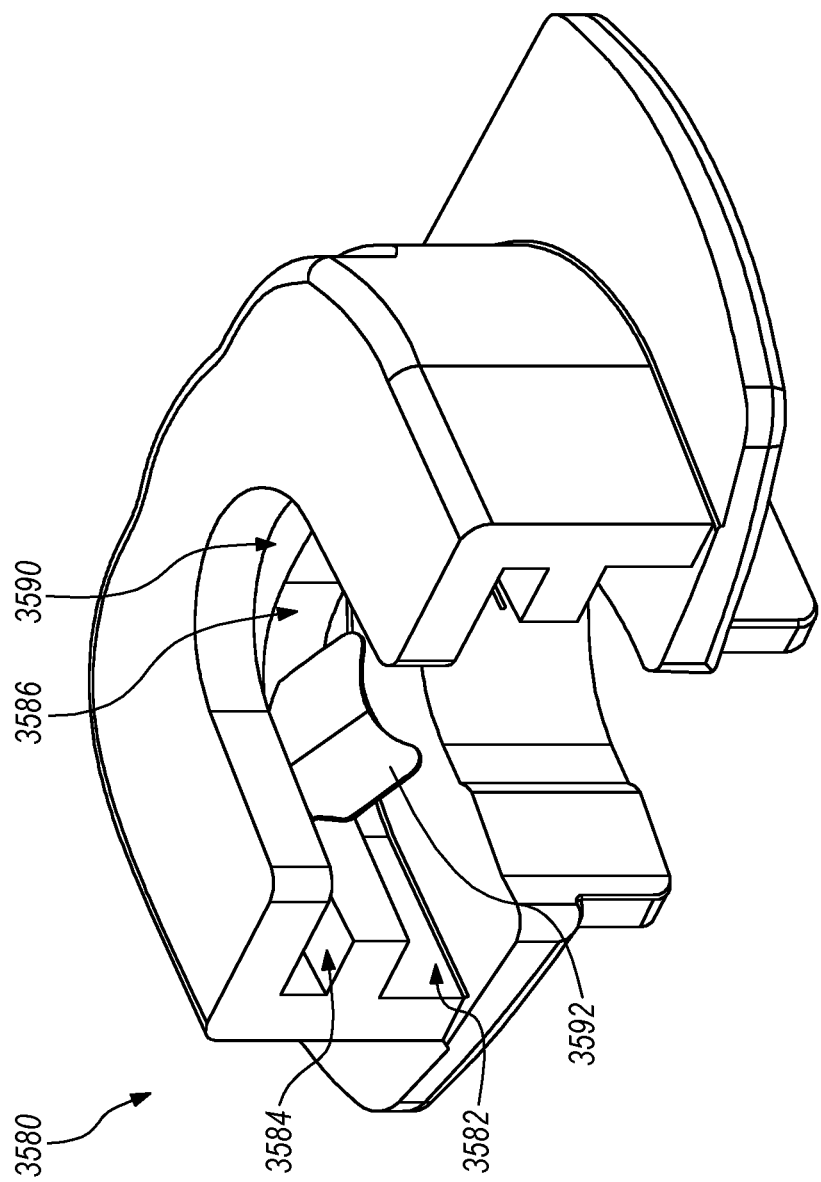
Figure 39:
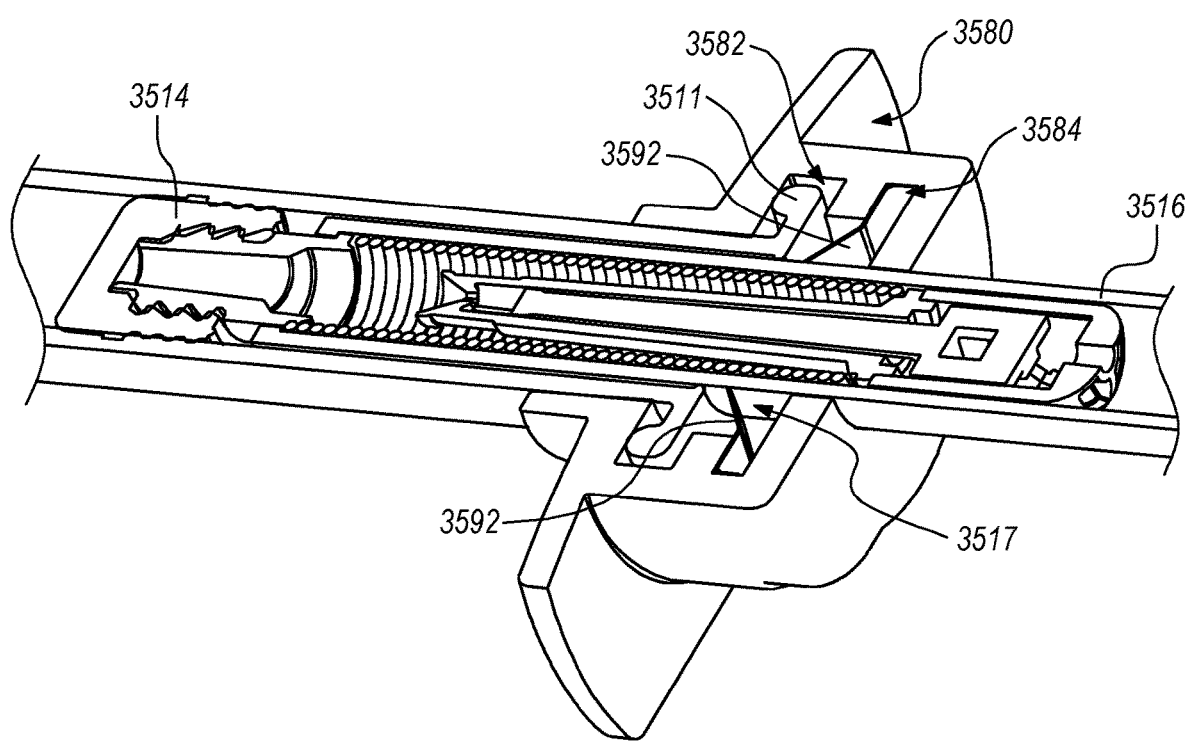
Figure 40:
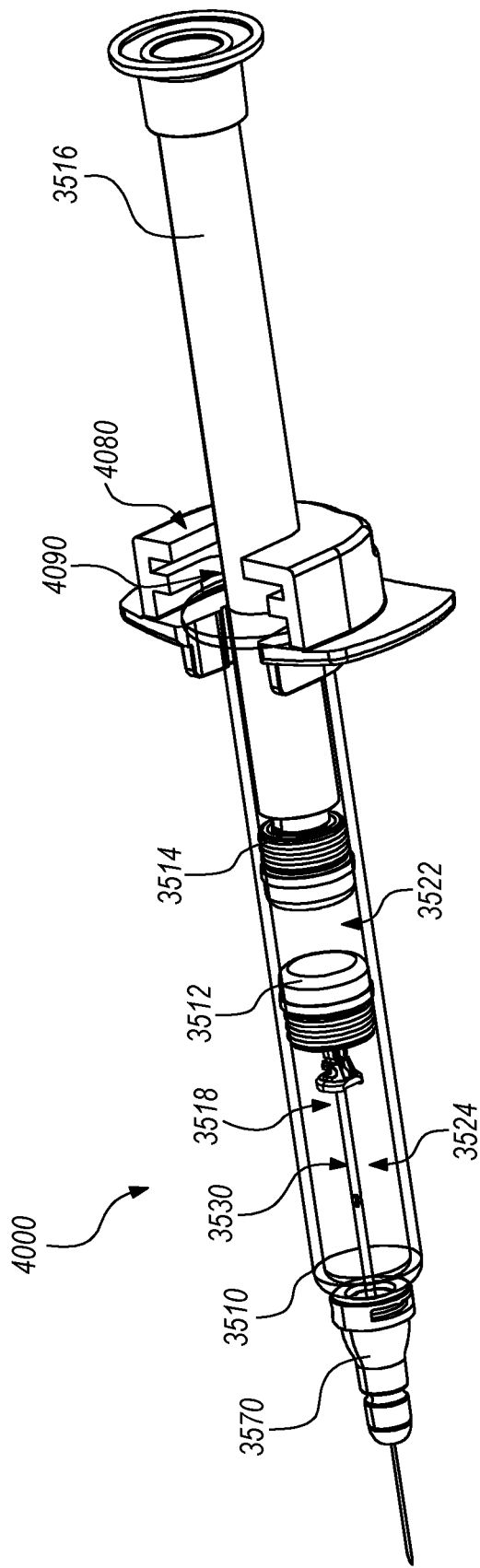
Figure 41:
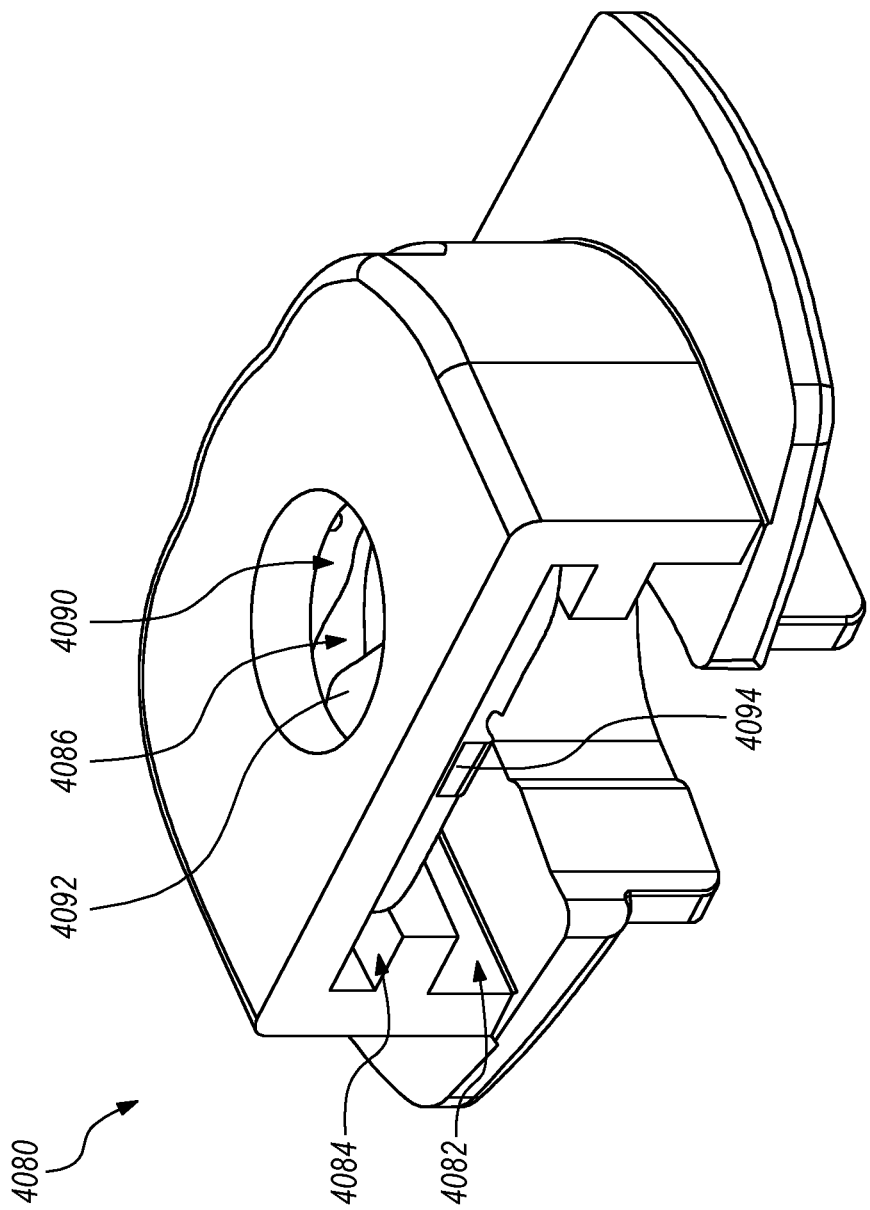

FIGS. 36 to 39 depict the finger flange 3580, which is configured to be mounted onto a small flange 3511 formed at the proximal end of the syringe body 3510 (see FIG. 39). As shown in FIG. 36, the finger flange 3580 defines a first recess 3582 configured to receive the small flange 3511 to couple the finger flange 3580 to the syringe body 3510. The finger flange 3580 also defines a second recess 3584 configured to receive the anti-retraction mechanism 3590. The anti-retraction mechanism 3590 includes a pair of brake tabs 3592 configured to provide an opposing force with proximal movement of the plunger member 3516 relative to the anti-retraction mechanism 3590, while allowing distal movement. The opposing force may include a frictional force as the brake tabs 3592 contact an outer surface 3517 of the plunger member 3516 and a reaction force as the brake tabs 3592 dig into an outer surface 3517 of the plunger member 3516. The acute angle of the brake tabs 3592 creates the reaction force parallel to the plunger member 3516, exerted by a sharp curved edge of each of the brake tabs 3592 contacting the surface 3517 of the plunger member 3516. This reaction force along with the frictional force prevents the plunger member 3516 from moving in the proximal direction. The finger flange 3580 further defines a "C" shaped opening 3586 configured to receive the plunger member 3516 (see FIG. 35). Due to the "C" shaped opening 3586, the finger flange 3580 can be slid onto the small flange 3511 from the side of the small flange 3511 after the plunger member 3516 is inserted during assembly. The "C" shaped finger flange 3580 and anti-retraction mechanism 3590 depicted in FIGS. 35 to 39 can be slid/snapped on to the small flange 3511 of the syringe body 3510 after the plunger member 3516 is inserted. Syringe bodies 3510 with plunger members 3516 screwed into proximal stopper members 3514 are able to pack more tightly into shipping trays for transportation. The finger flange 3580 with is the anti-retraction mechanism 3590 is snapped after shipping, and snaps around both the syringe body 3510 and the plunger member 3516.

Figure 37:
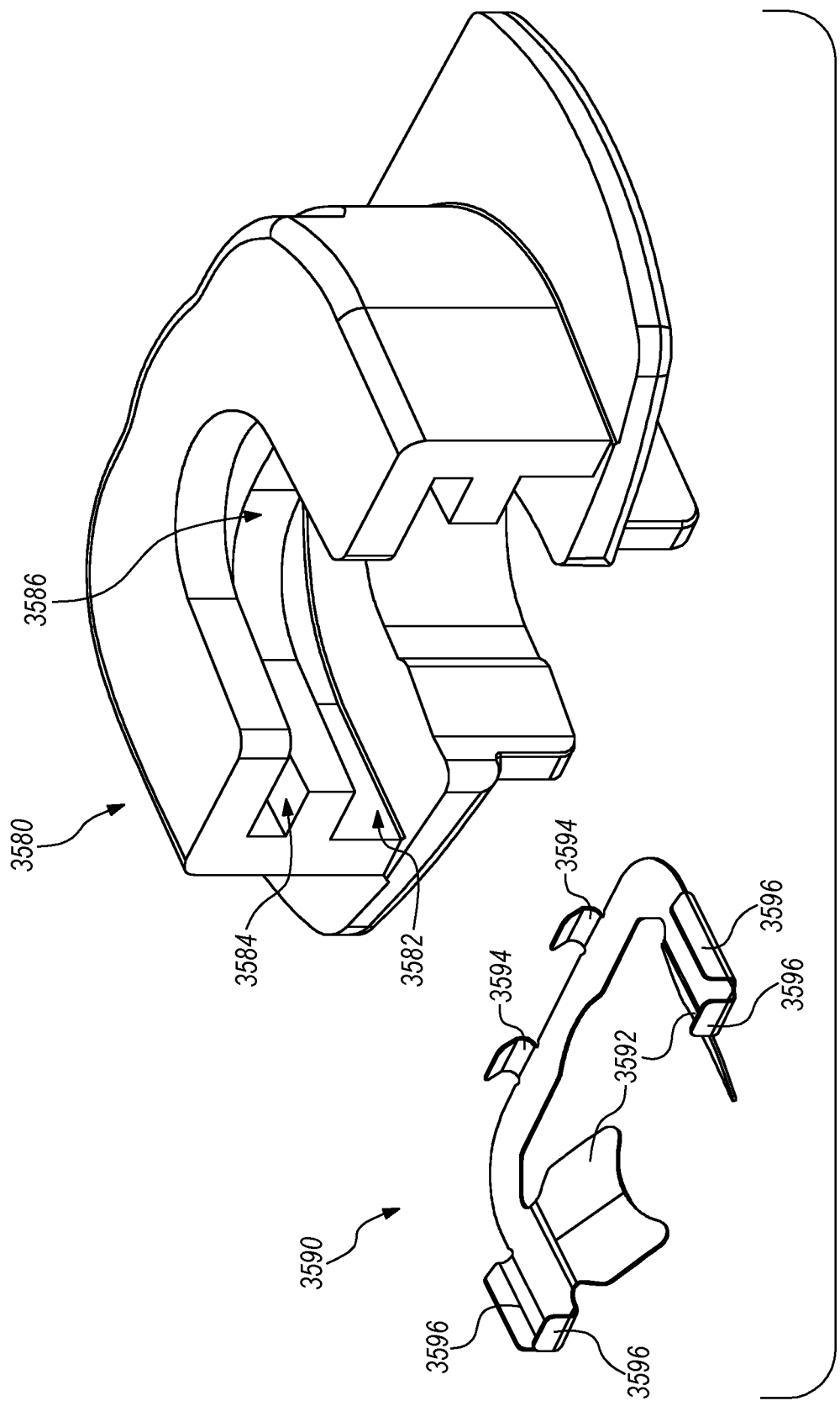
Figure 38:
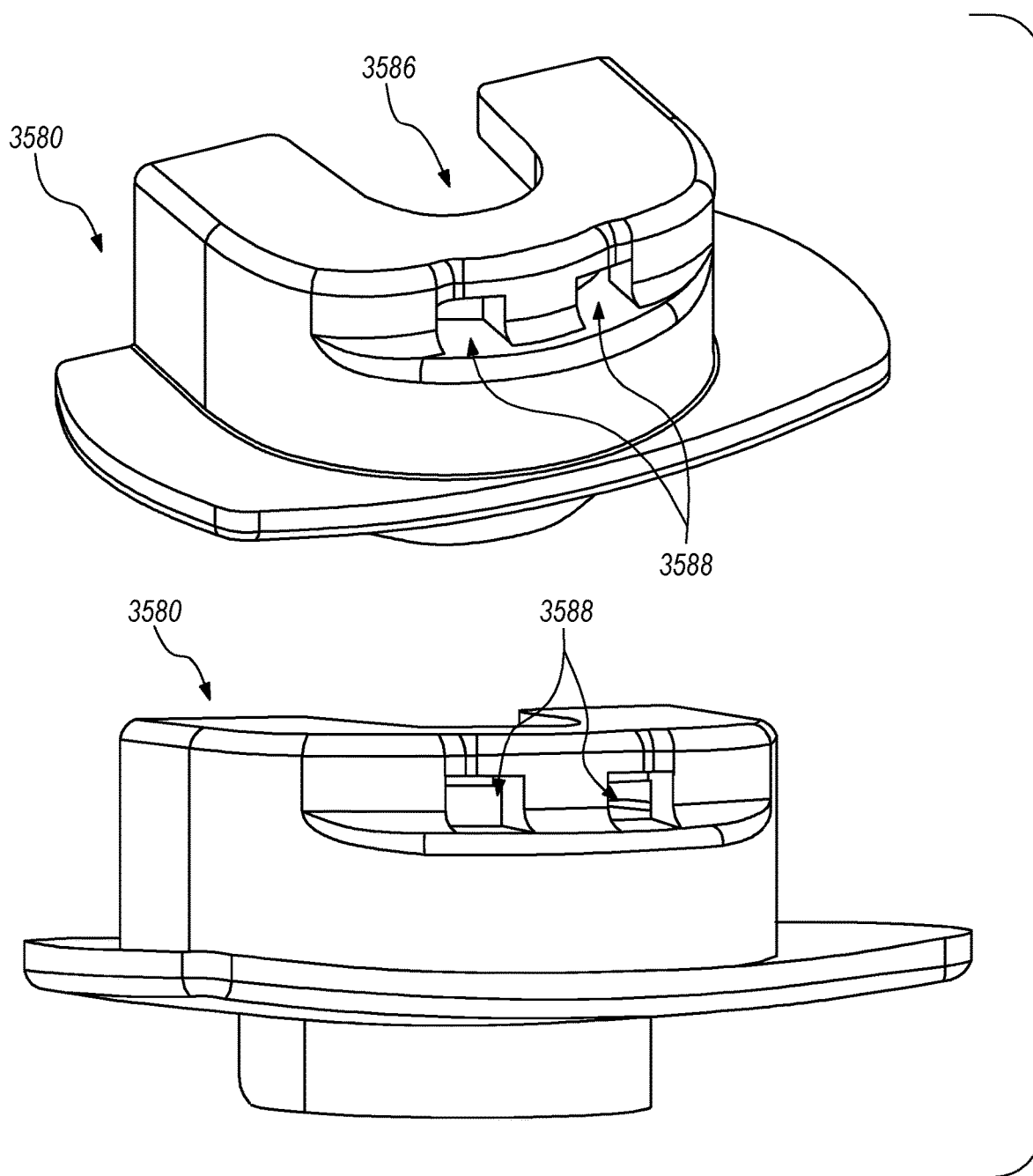

As shown in FIG. 37, the anti-retraction mechanism 3590 is a generally "C" shaped clip. In some embodiments, the anti-retraction mechanism 3590 is cut or stamped from a sheet of metal and then certain portions thereof are bent to the final shape. The anti-retraction mechanism 3590 includes a pair of brake tabs 3592 configured to provide an opposing frictional force with proximal movement of the plunger member 3516 as described above. The brake tabs 3592 are the elastically deformable and self-energizing. The brake tabs 3592 extend at an acute angle in a distal direction relative to the plane of the anti-retraction mechanism 3590 (i.e., the brake tabs 3592 are bent downwards). The angle and elasticity of the brake tabs 3592 allows the plunger member 3516 to slide past the break tabs 3592 in the in distal direction. When the plunger member 3516 is pulled in a proximal direction relative to the brake tabs 3592, the brake tabs 3592 make contact with and dig into an outer surface 3517 of the plunger member 3516 and prevent proximal plunger member 3516 movement relative to the break tabs 3592. Because the brake tabs 3592 are self-energizing, with attempted proximal movement, the brake tabs 3592 engages with the plunger member 3516 by increasing a frictional force applied to the plunger member 3516 and an amount of digging into the plunger member 3516 to prevent its proximal movement. In effect, the brake tabs 3592 form a pair of pawls to engage the plunger member 3516 and prevent proximal movement thereof. In some embodiments, the plunger member (not shown) may have annular grooves threads and/or formed thereon to increase the ratcheting effect of the brake tabs 3592. The anti-retraction mechanism 3590 and the brake tabs 3592 prevent removal of the plunger member 3516 from the dual chamber injection system 3500 after use.

The anti-retraction mechanism 3590 also includes a pair of retention tabs 3594 configured to hold the anti-retraction mechanism 3590 in the second recess 3584 of the finger flange 3580. The retention tabs 3594 are bent inward so that they are configured to grip the inside of the second recess 3584 in the finger flange 3580 with a frictional force and a reaction force to prevent removal of the anti-retraction mechanism 3590 from the second recess 3584. The retention tabs 3594 are also self-energizing to provide increasing frictional and reaction force as the anti-retraction mechanism 3590 is pulled from the second recess 3584. In the embodiment depicted in FIG. 38, the finger flange 3580 includes a pair of openings 3588 configured to receive the retention tabs 3594 from the anti-retraction mechanism 3590 to retain the anti-retraction mechanism 3590 in the second recess 3584 by interference instead of friction.

As shown in FIG. 37, the anti-retraction mechanism 3590 also includes four fit tabs 3596 configured to reduce a tolerance between the second recess 3584 and the anti-retraction mechanism 3590 thereby providing a tighter fit of the anti-retraction mechanism 3590 in the second recess 3584. The original tolerance is larger because, in some embodiments, the finger flange 3580 is molded from a polymer, and therefore has minimum size limitations for recesses that can be accurately and precisely formed therein. On the other hand, the anti-retraction mechanism 3590 is cut from a sheet of metal, and therefore has a thinner profile then the height of the second recess 3584. The fit tabs 3596 increase the thickness/height of the anti-retraction mechanism 3590, thereby providing a tighter fit in the second recess 3584. The fit tabs 3596 also provide rigidity to the anti-retraction mechanism 3590. Accordingly, when the plunger member 3516 is pulled proximally, the brake tabs 3592 (because of their elasticity and angle) exert an outward force on the anti-retraction mechanism 3590. This outward force is transferred through the anti-retraction mechanism 3590 and the fit tabs 3596 to push against the inside of the second recess 3584 of the finger flange 3500 due to the rigidity of the anti-retraction mechanism 3590. This outward force is the reactive force to the frictional and reaction forces applied to the plunger member 3516 to prevent its proximal movement.

FIGS. 40 to 43 depict a dual chamber injection system 4000 with a finger flange 4080 having an anti-retraction feature 4090 according to some embodiments. The dual chamber injection system 4000 has many of the same components as the dual chamber injection system 3500 depicted in FIGS. 35 to 39 and described above. Those components have the same reference numerals as the corresponding components in the dual chamber injection system 3500. The difference between the dual chamber injection systems 3500, 4000 is in the finger flanges 3590, 4090. Unlike the finger flange 3590 depicted in FIGS. 36 and 37, which has a "C" shaped opening 3586 for receiving the plunger member 3516, the finger flange 4090 depicted in FIGS. 41 and 42 has an "O" shaped opening 4086 for receiving the plunger member 3516. The "O" shaped opening 4086 provides an additional mechanism for preventing removal of the plunger member 3516 from the dual chamber injection system 4000 after use.

Figure 42:
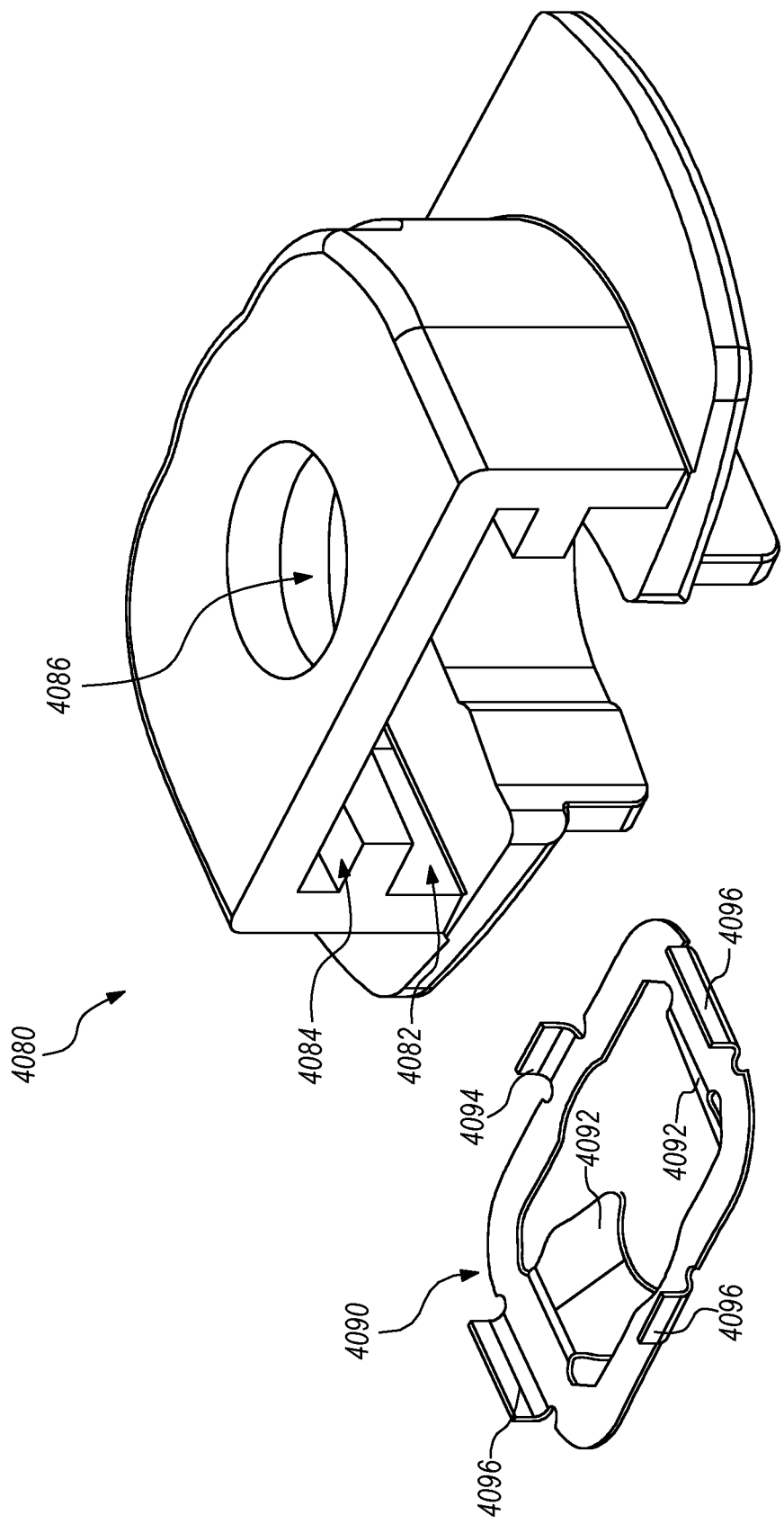
Figure 43:
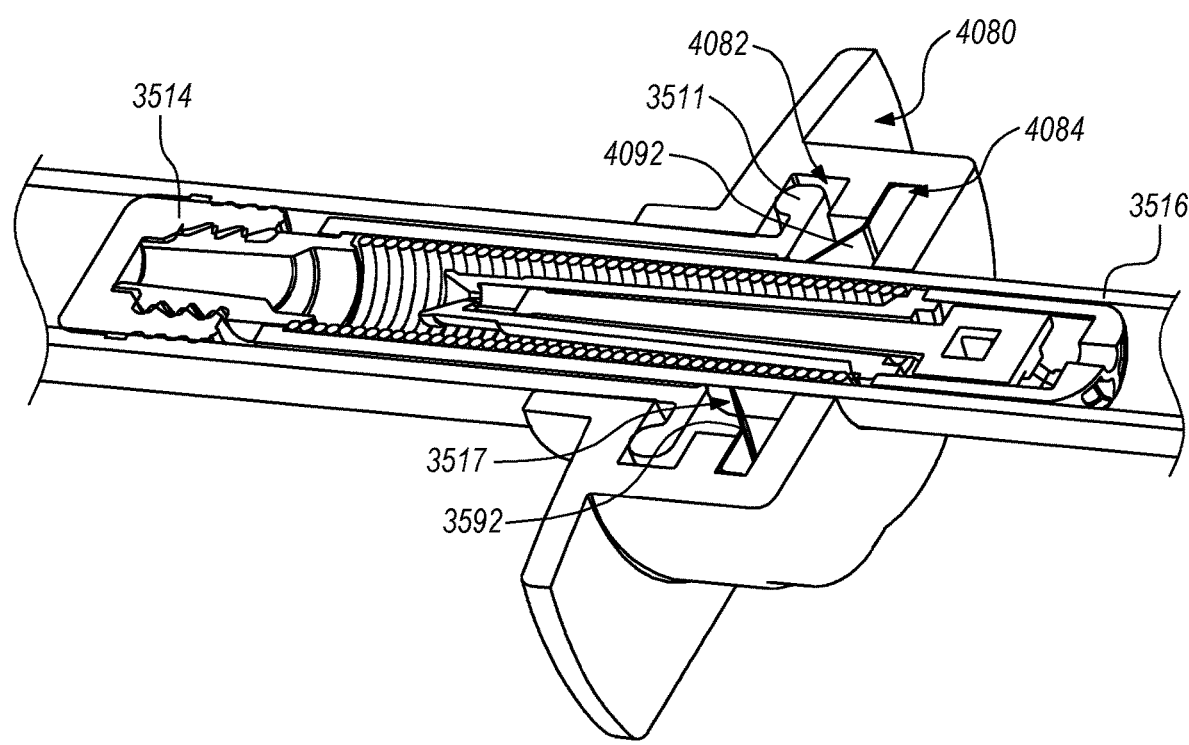

As shown in FIG. 42, the anti-retraction mechanism 4090 in the finger flange 4080 has an "O" and/or rectangular shape. The anti-retraction mechanism 4090 can be cut from a sheet of metal. Due to the "O" and/or rectangular shape of the anti-retraction mechanism 4090, the anti-retraction mechanism 4090 is inserted into the finger flange 4080, and the finger flange 4080 with the anti-retraction mechanism 4090 is snapped onto the small flange 3511 before the plunger member 3516 is inserted into the syringe body 3510 (see FIGS. 40 and 43). In such embodiments, the plunger member 3516 is inserted through the "O" shaped opening 4086 in the finger flange 4080. As such, interference between the "O" shaped opening 4086 in the finger flange 4080, the plunger member 3516, and the syringe body 3510 prevents removal of the finger flange 4080 from the syringe body 3510 after assembly. On the other hand, the finger flange 3580 depicted in FIGS. 35 to 40, which has a "C" shaped opening 3586 can be slid/snapped onto the small flange 3511 from the side of the small flange 3511 at any time during assembly. The "O" shaped opening 4086 in the finger flange 4080 also aligns the plunger member 3516 in the syringe body 3510.

The brake tabs 4092 in the anti-retraction mechanism 4090 depicted in FIG. 42 are identical to the brake tabs 3592 in the anti-retraction mechanism 3590 depicted in FIG. 37, which are described above. The retention tab 4094 in the anti-retraction mechanism 4090 depicted in FIG. 42 are similar to the retention tabs 3594 in the anti-retraction mechanism 3590 depicted in FIG. 37, which are described above. The difference is that there is a single retention tab 4094 in anti-retraction mechanism 4090, while there is a pair of retention tabs 3594 in anti-retraction mechanism 3590. The fit tabs 4094 in the anti-retraction mechanism 4090 depicted in FIG. 42 are similar to the fit tabs 3596 in the anti-retraction mechanism 3590 depicted in FIG. 37, which are described above. The difference is that there are three fit tabs 4094 in anti-retraction mechanism 4090, while there are four fit tabs 3594 in anti-retraction mechanism 3590.

The anti-retraction mechanism 4090 depicted in FIGS. 40 to 43 is symmetrical, simplifying high volume assembly whether manual or automated. In embodiments where the plunger member (not shown) has annular grooves and/or threads, the anti-retraction mechanism 4090 may prevent removal of plunger member 3516 from the dual chamber injection system 4000. Further, the pair of long beams in the "O" shaped anti-retraction mechanism 4090 are deformable, allowing the anti-retraction mechanism 4092 bow outward, thereby transferring an outside reactive force to the interior walls of the second recess 4084 via the outside/long fit tabs 4096.

Exemplary Elastic Needle Latches

Figure 44A:
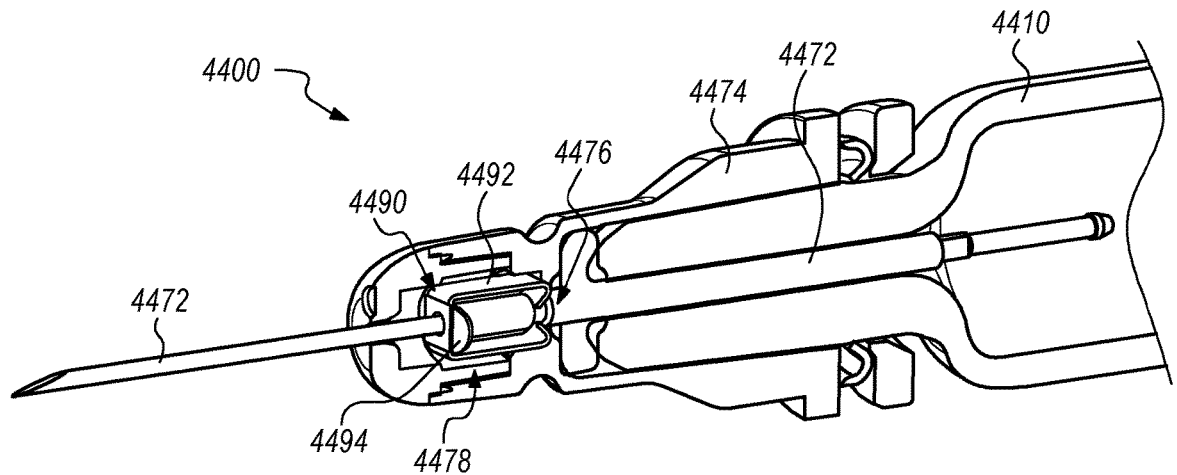
FIGS. 44A to 44E depict needle hub assembly with an elastic needle latch for use with safe needle retraction injection systems according to some embodiments.

FIGS. 44A to 45B depict a needle latching mechanism 4490 for use with safe injection needle retraction systems 4400 according to some embodiments. An elastic needle latch 4490 is disposed in a needle hub 4474 and retains a needle 4472 in the distal end of a syringe body 4410 during injection and releases the needle 4472 for retraction after the injection is complete. FIG. 44A is a semi-cross sectional view of the injection system 4400 depicting the needle 4472 in the latched state in which the needle latch 4490 couples the needle 4472 to the needle hub 4474. The needle 4472 has an annular latching groove 4476 which couples to the elastic needle latch 4490. The elastic needle latch 4490 is configured such that it has a latched state (see FIG. 44A) where a pair of latching arms 4492 are restrained and/or compressed into engagement with the needle annular latching groove 4476 and an unlatched state (see FIG. 44B) where the latching arms 4492 are free to spring open, disengaging from the annular latching groove 4476 and releasing the needle 4472 for retraction. The needle hub 4474 defines a recess 4478 with an inner diameter and a restraining surface configured to restrain the elastic needle latch 4490 in the latched configuration.

Figure 44B:
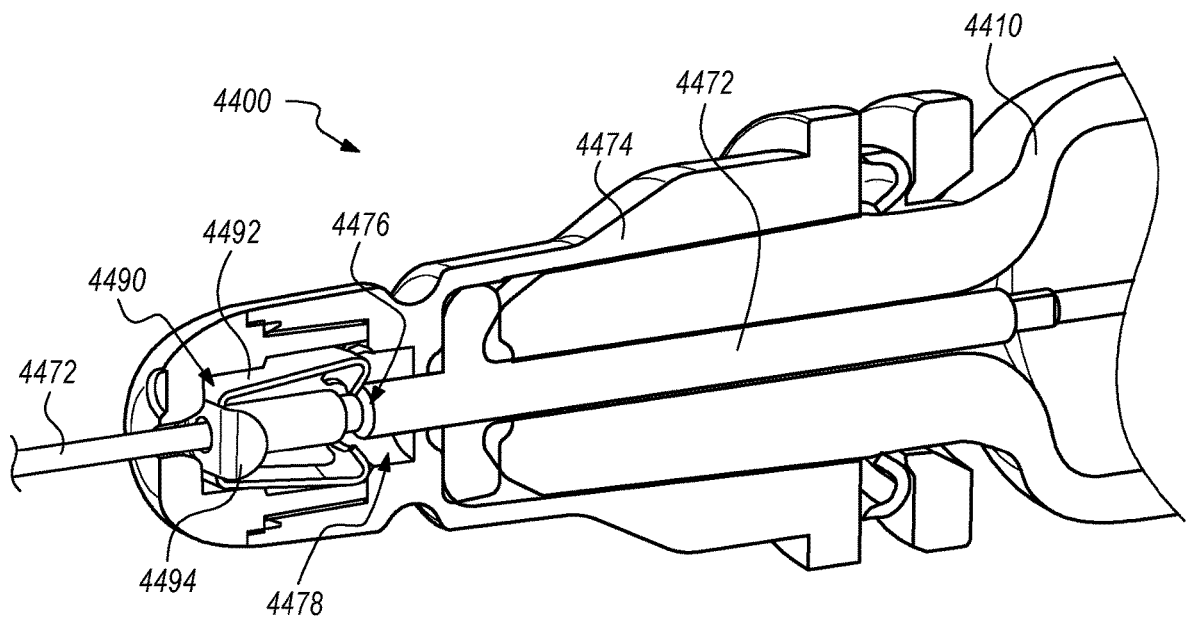

FIG. 44B is another semi-cross sectional view that illustrates the needle unlatching process. To unlatch the needle 4472, the needle 4472 and the coupled elastic needle latch 4490 are pushed distally by the advancing a plunger member (not shown). The elastic needle latch 4490 is configured such that the needle latch 4490 is pushed distally after the injection is substantially complete. The distal movement of the elastic needle latch 4490 moves it out of the recess 4478 and allows the latching arms 4492 to slide distal of the restraining surface in the recess 4478, allowing the latching arms 4492 to expand radially (as the latching arms 4492 are biased to expand). The latching arms 4492 expanding radially dis-engages the latching surfaces of the latching arms 4492 from the needle annular latching groove 4476, thereby releasing the needle 4472 to be retracted proximally relative to the needle hub 4474 and the syringe body 4410. Needle retraction mechanisms with which the elastic needle latch 4490 may be used are described in U.S. Utility patent application Ser. No. 14/696,342, which was previously incorporated by reference herein.

Figure 44C:
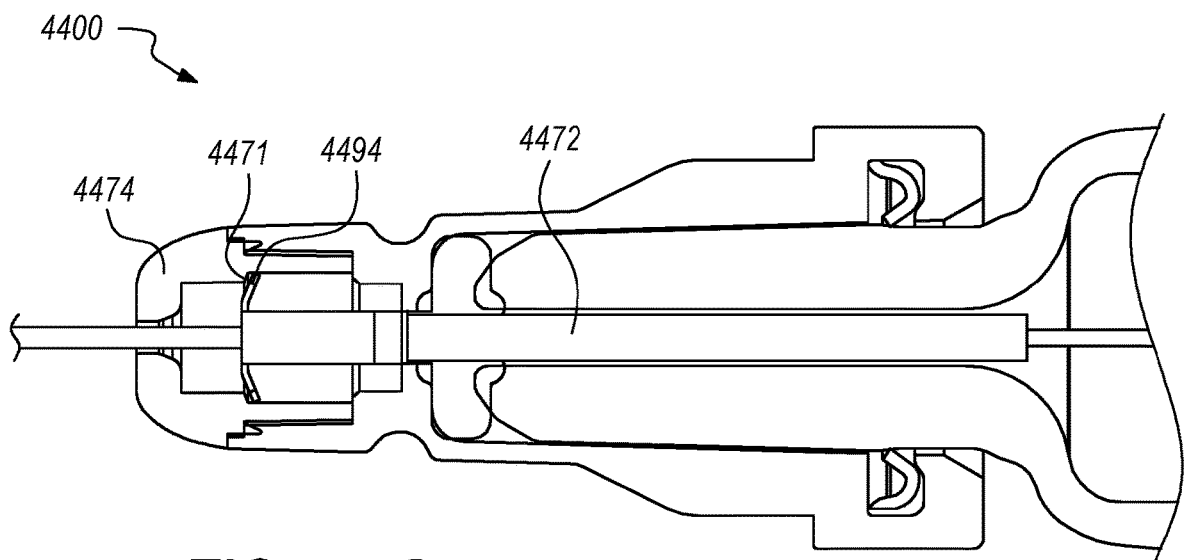
Figure 44D:
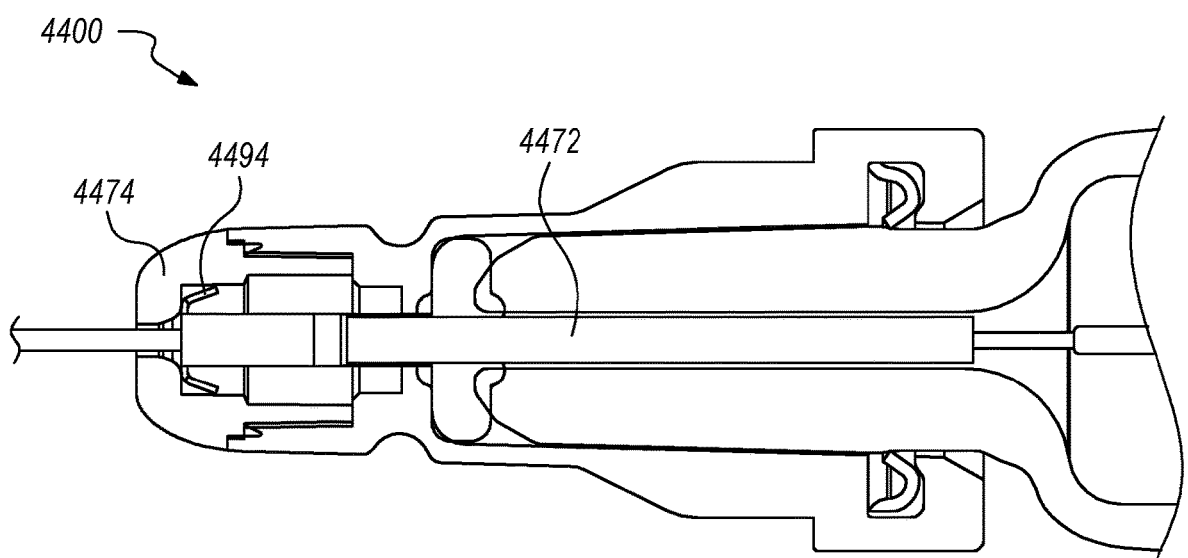
Figure 44E:
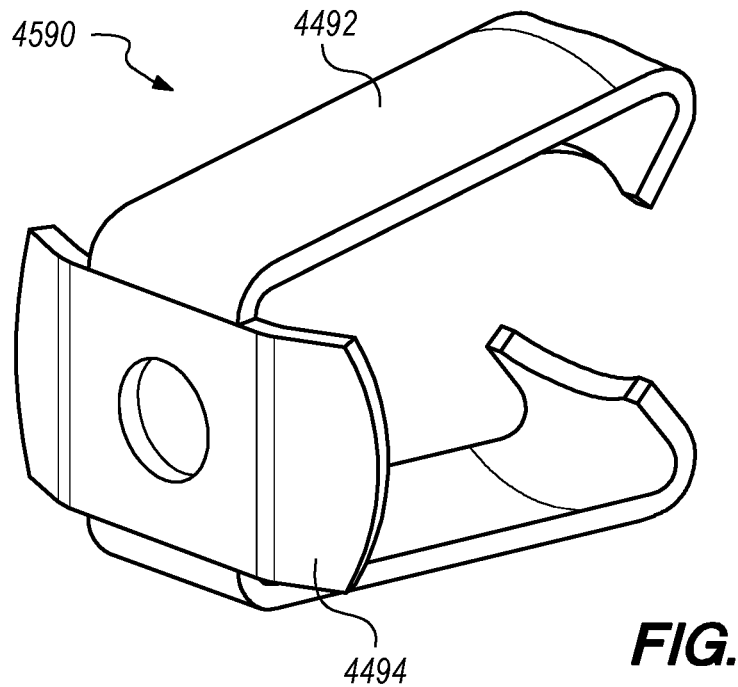
Figure 44F:
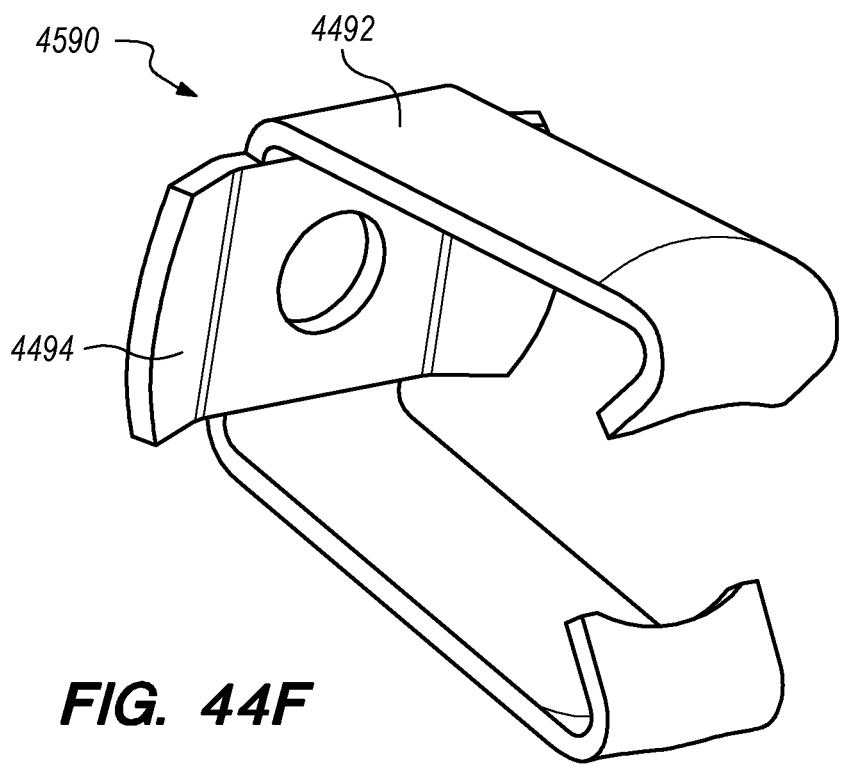

FIGS. 44C and 44D are semi-cross sectional views (rotated 90 degrees from FIGS. 44A and 44B on the longitudinal axis) that illustrate a pair of flexible unlatch force arms/retaining tabs 4494 on the elastic needle latch 4490. FIG. 44C depicts the needle 4472 in the latched state, and FIG. 44D depicts the needle 4472 in the unlatched state. The desired force to unlatch the needle 4472 is between approximately 2 lbf and approximately 4 lbf. To configure the elastic needle latch to unlatch at the desired unlatching force, the retaining tabs 4494 engage a generally proximally facing annular shelf 4471 in the inside of the nose cone of the needle hub 4474. In FIG. 44C, the retaining tabs 4494 are in a straight state, wherein they prevent the elastic needle latch 4490 from moving distally out of the recess (see FIG. 44A). The retaining tabs 4494 are configured so that upon application of a distally directed force onto the needle assembly (which transmit distally directed force to the elastic needle latch 4490), the retaining tabs 4494 engage the annular shelf 4471. The retaining tabs 4494 react the distally directed needle unlatch force until desired unlatch force is reached. At that point the retaining tabs 4494 bend proximally, transforming into a bent state and allowing the elastic needle latch 4490 to advance distally out of the recess 4478, causing the latching restraint to be removed, and allowing the needle 4472 to be released. FIGS. 44E and 44F are isometric views of the elastic needle latch 4490 of FIGS. 44A to 44D with the latching arms 4492 in the unlatched state and the retaining tabs 4494 in the straight state.

Exemplary Elastomeric Needle Retention Systems

Figure 45A:
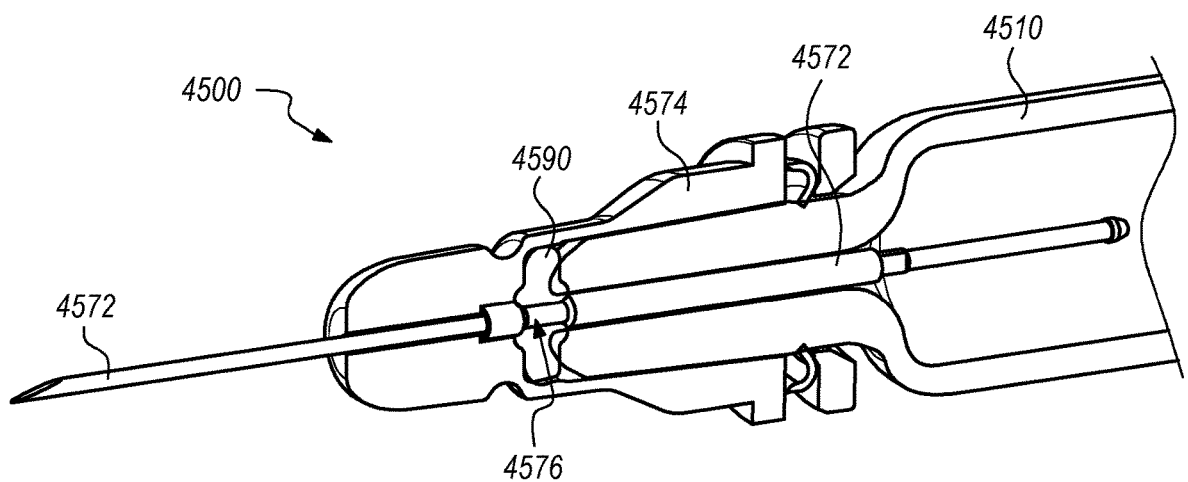
FIGS. 45A to 45D depict needle hub assembly with an elastomeric needle retention system for use with safe needle retraction injection systems according to some embodiments.
Figure 45B:
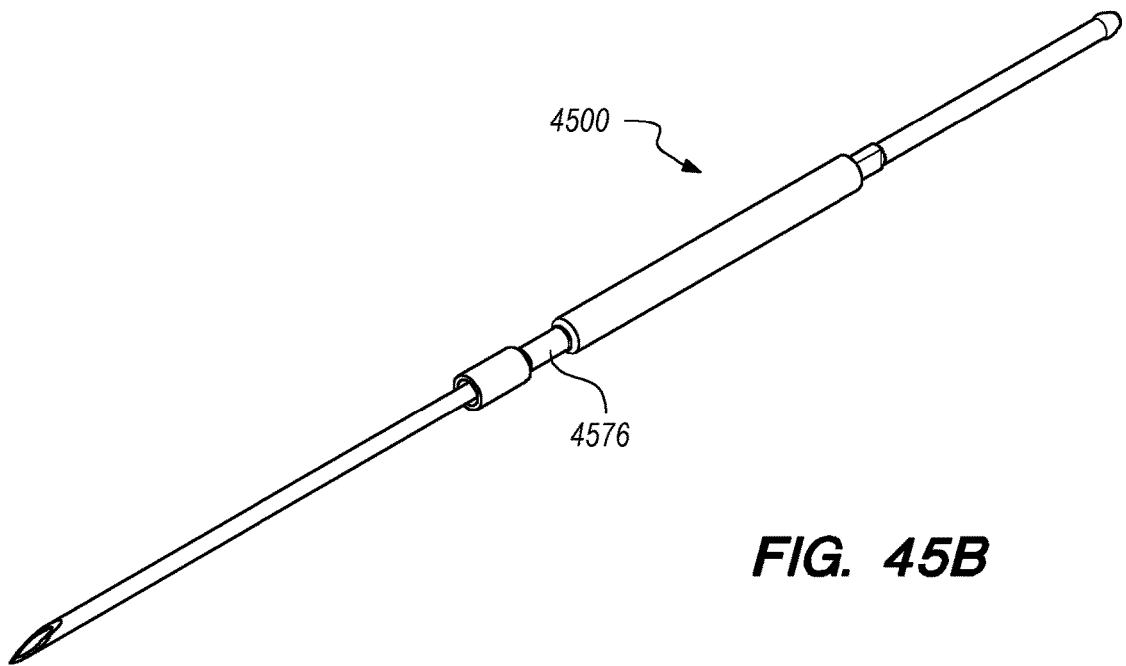
Figure 45C:
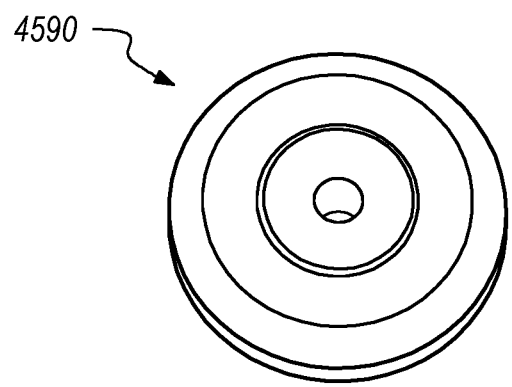
Figure 45D:
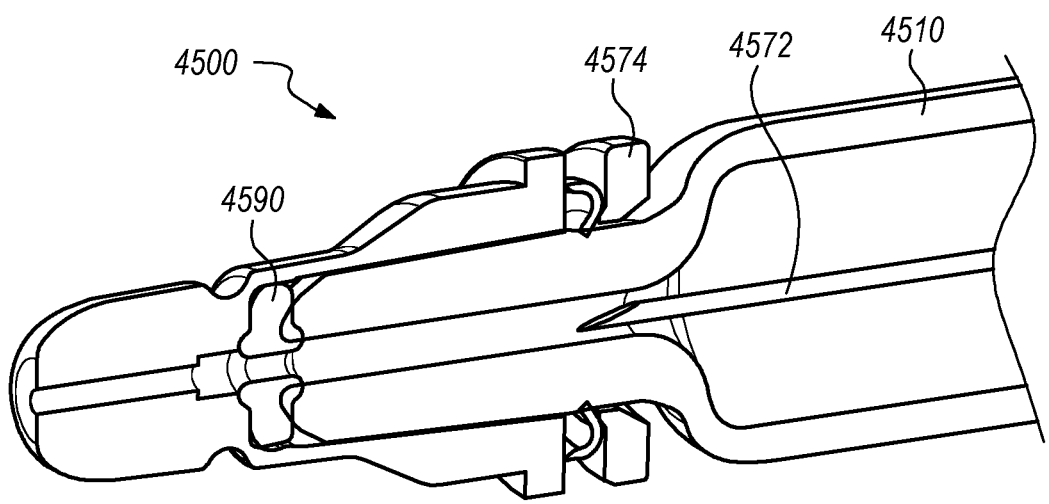

FIGS. 45A to 45D are a semi cross-section views depicting a mechanism for retaining a needle 4572 during injection and allowing the needle 4572 to be retracted after the injection has been completed according to some embodiments. The needle retention systems depicted in FIGS. 45A to 45D are similar to those described in U.S. patent application Ser. No. 14/321,706, and are applicable to U.S. Provisional Patent Application Ser. No. 62/827,767 62/827, 767, which have been previously incorporated by reference herein. The safe injection system 4500 includes a needle hub 4574, an elastomeric seal 4590, and a needle 4572 with an annular seal seat 4576 (FIG. 45B). The elastomeric seal 4590 (FIG. 45C) has an internal sealing surface, a syringe sealing surface, and a needle hub sealing surface. The elastomeric seal 4590 is configured to provide a pressure seal between the inside of the syringe body 4510, the needle hub 4574, and the outside of the needle 4572. The elastomeric seal 4590 is also coupled to the outside of the needle 4572 by a frictional and/or mechanical engagement mechanism, which provides resistance to proximal movement of the needle 4572 into the interior of the syringe body 4510 during injection. The resistance to proximal movement is tuned such that it is sufficient to perform the injection while not strong enough to prevent the needle retraction mechanism from grasping and retracting the needle 4572 into the syringe body 4510 and/or into the plunger member as described in U.S. Utility patent application Ser. No. 14/696, 342, which was previously incorporated by reference herein. Proximal movement resistance forces above approximately 1.5 lbf and below approximately 3.0 lbf provide sufficient movement resistance to allow assembly and injection while also allowing the retraction spring to overcome the needle retention force and retract the needle 4572 (see FIG. 45D). Alternatively, the elastomeric seal may be an O-Ring or a slab of elastomer (not shown) that is pierced by the needle 4572 upon assembly. In some embodiments, the needle 4572 has a distally facing surface that engages with a proximally facing surface inside the needle hub 4574 to prevent distal movement of the needle 4572 during cap removal, handling, injection of medication, and/or during removal of the needle 4572 from the patient.

Exemplary Needle Hub Attachment Mechanisms for Polymeric Syringe Bodies

Figure 46A:
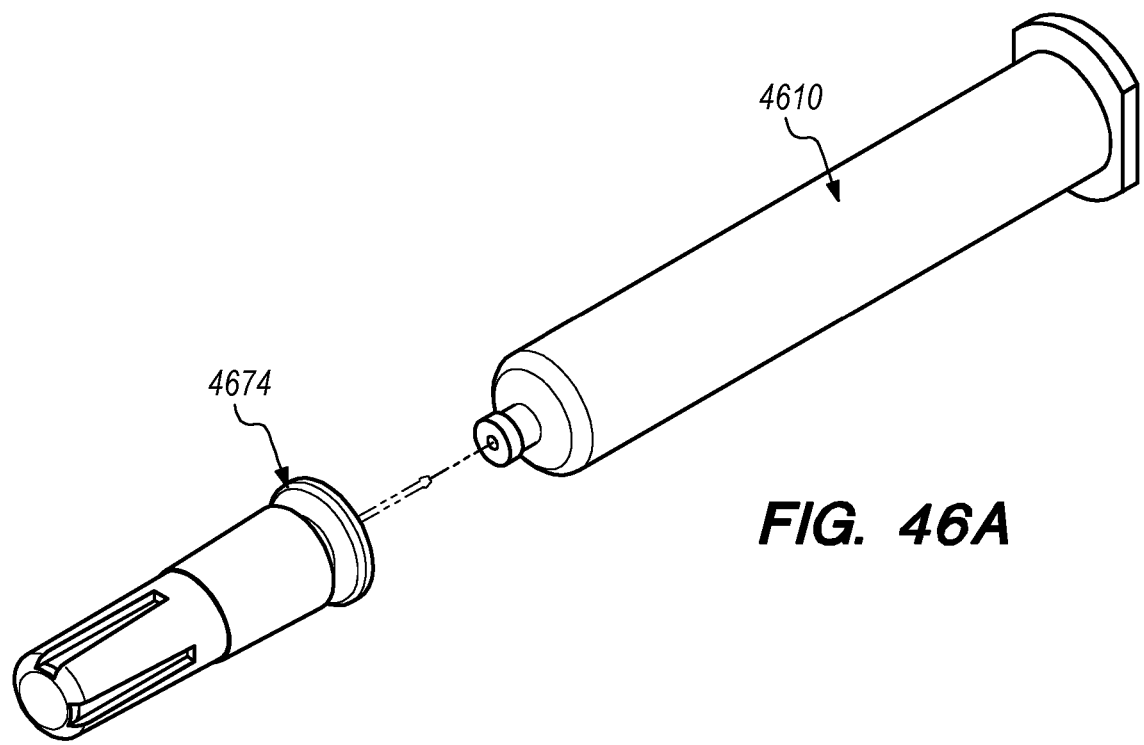
FIGS. 46A to 47H injection systems having needle hub attachment mechanisms according to some embodiments.
Figure 46B:
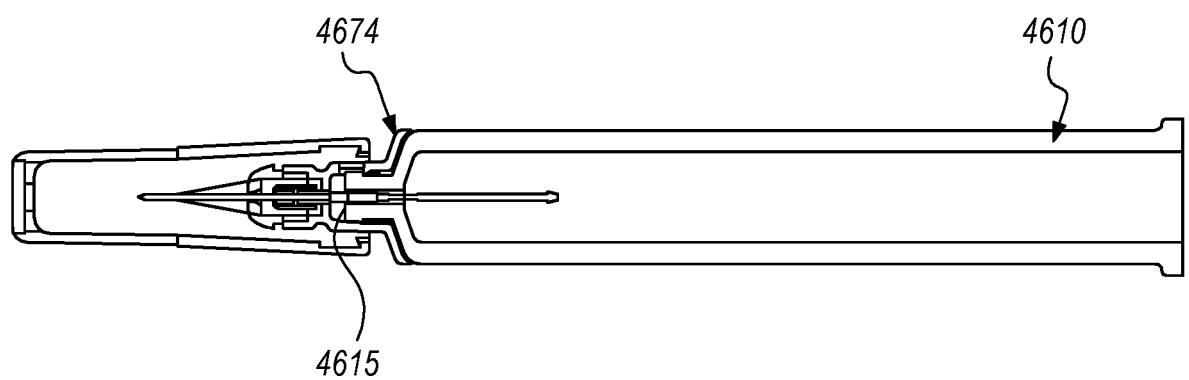
Figure 46C:
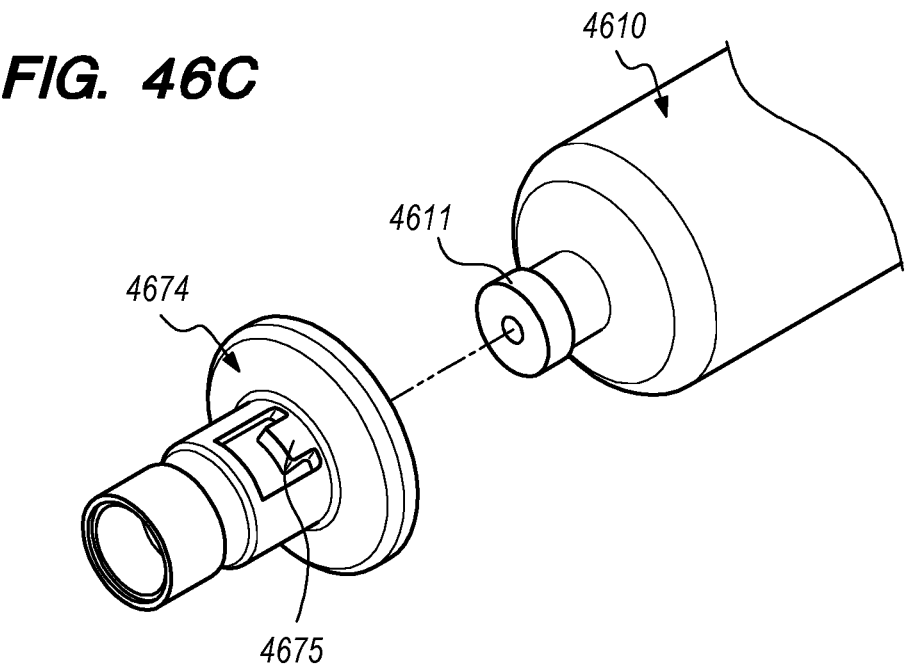
Figure 46D:
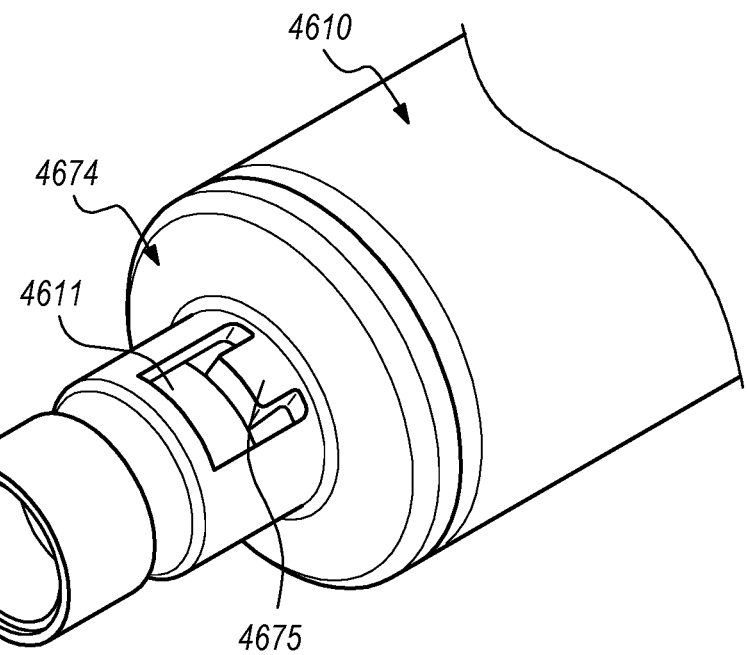
Figure 46E:
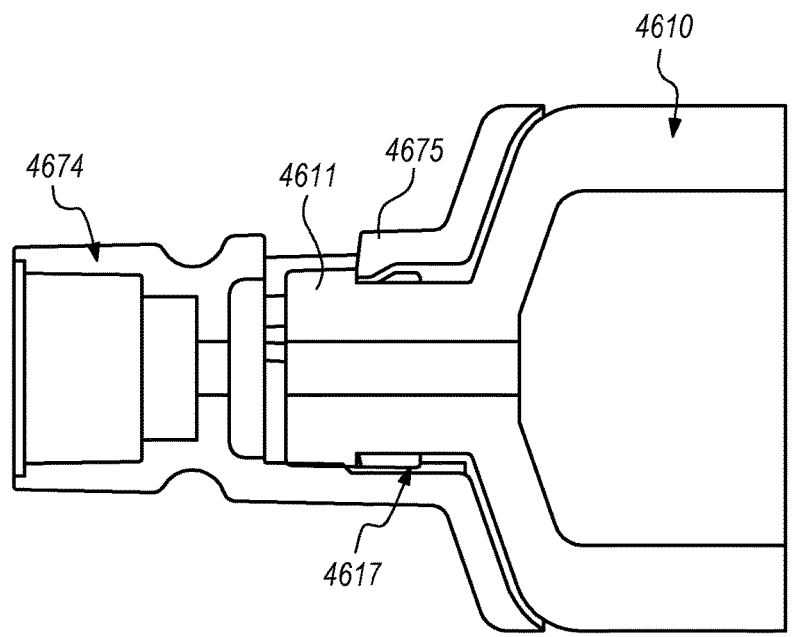

FIGS. 46A to 46E depict an attachment mechanism for coupling a needle hub 4674 to a polymeric syringe body 4610 according to various embodiments. In various embodiments, the polymeric syringe body 4610 may be molded from Cyclic Olefin Copolymer or Cyclic Olefin Polymer. The polymeric syringe body 4610 has a needle retention ledge 4611. As shown in FIGS. 46C to 46E, the needle hub 4674 has a latch 4675 configured to allow the needle retention ledge 4611 to pass in a distal direction then snap into a space 4617 (see FIG. 46E) proximal of the needle retention ledge 4611, thereby coupling the needle hub 4674 to the polymeric syringe body 4610. The injection system also includes a gasket 4615 (see FIG. 46B) inside of the needle hub 4674 distal to the polymeric syringe body 4610.

Figure 47A:
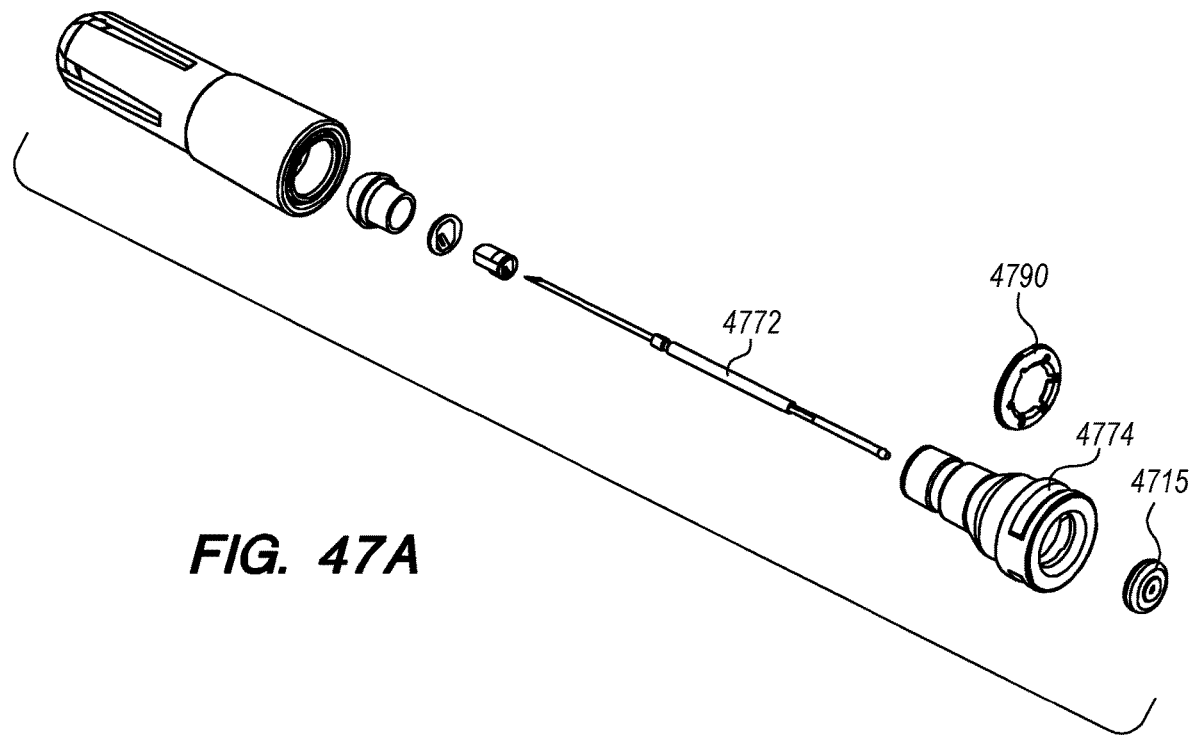
Figure 47B:
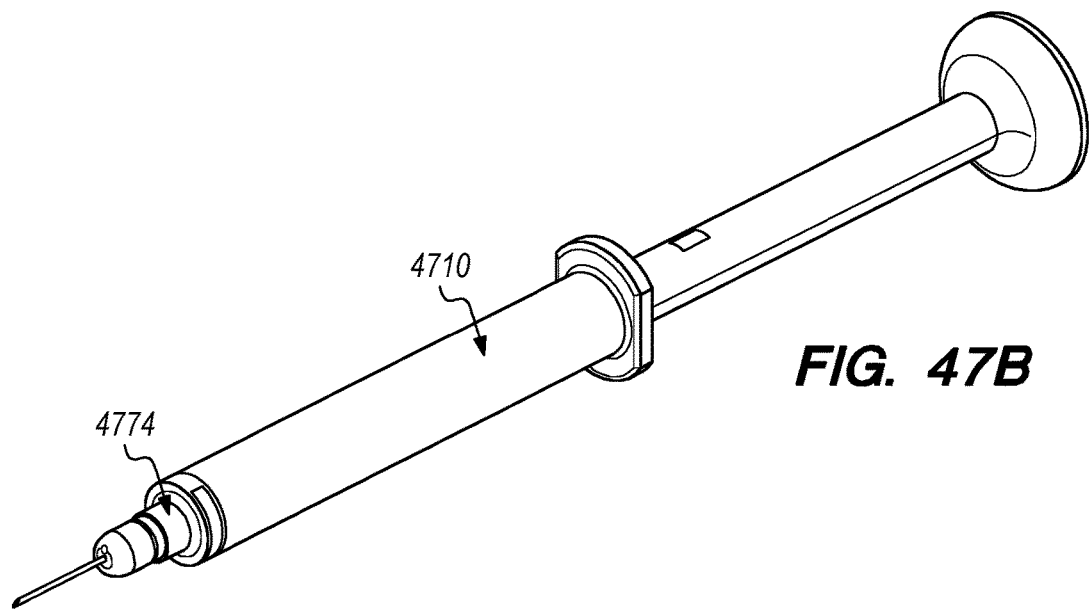
Figure 47C:
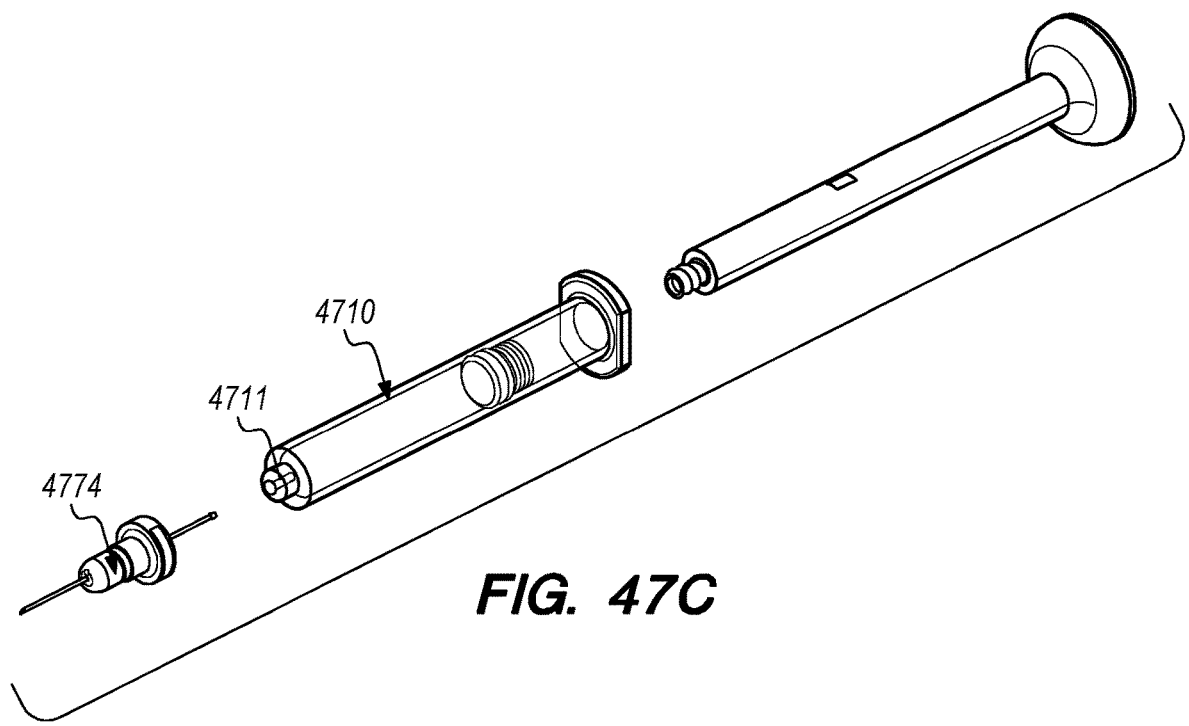
Figure 47D:
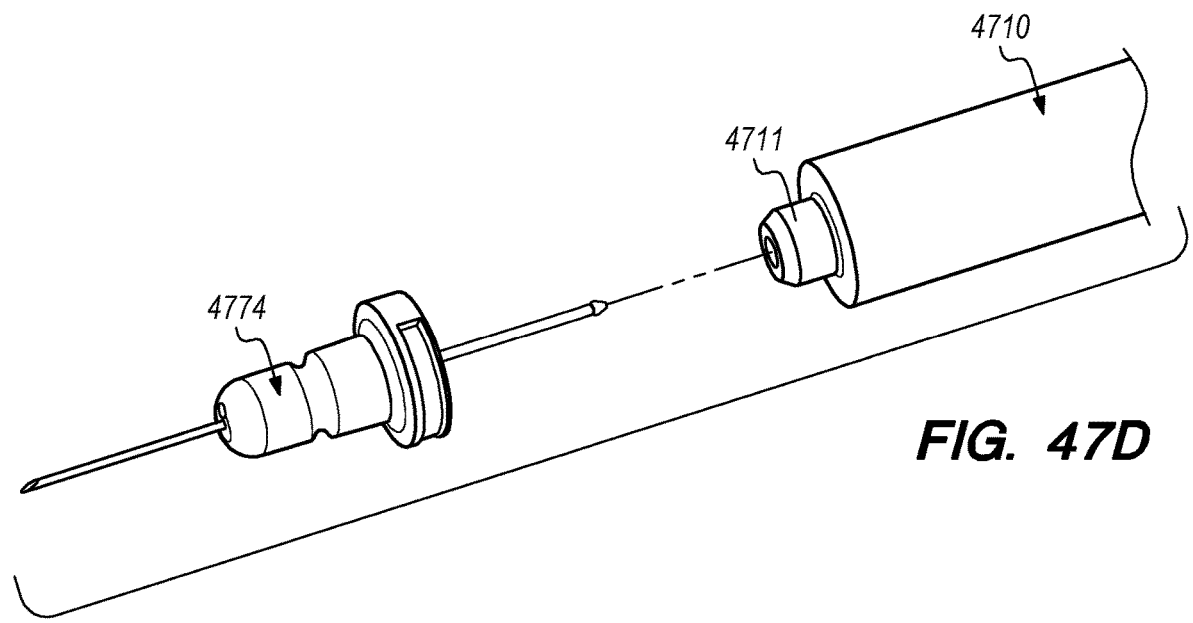
Figure 47E:
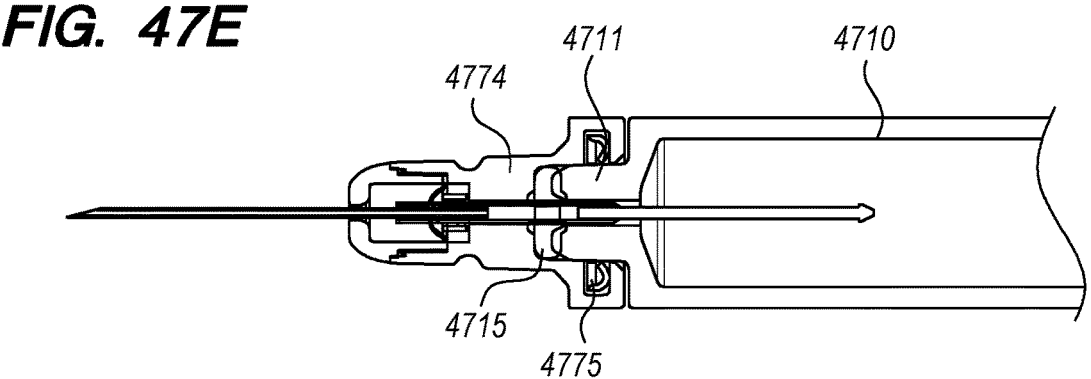
Figure 47F:
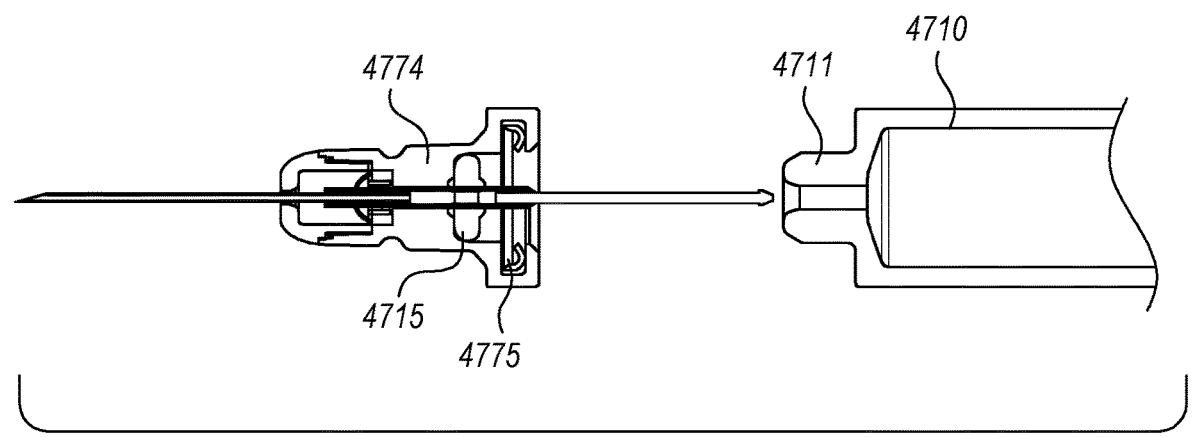
Figure 47G:
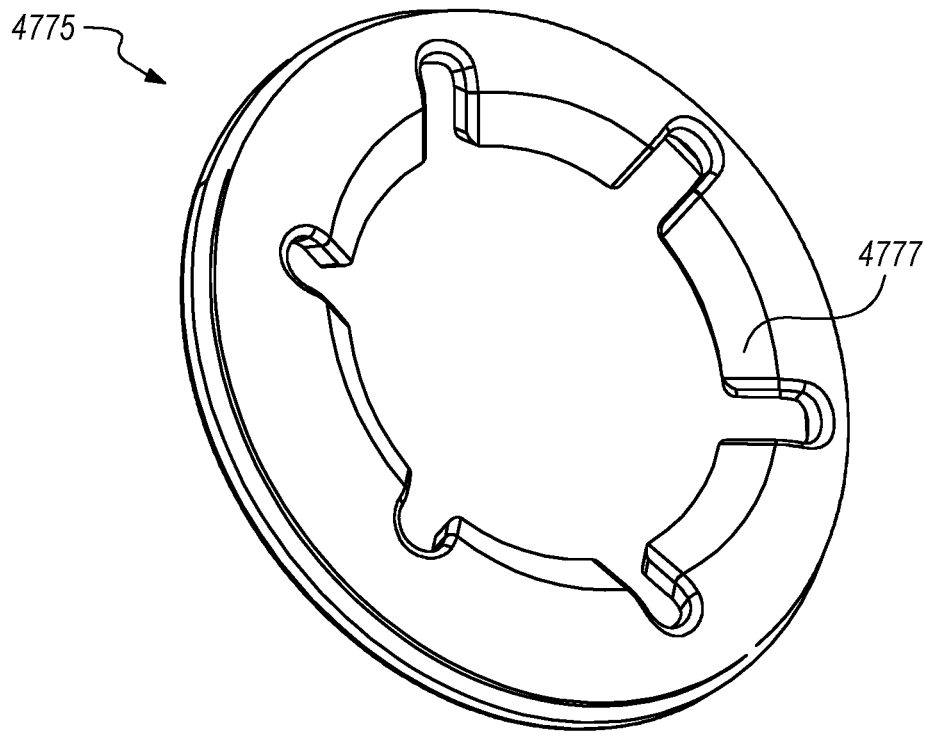
Figure 47H:
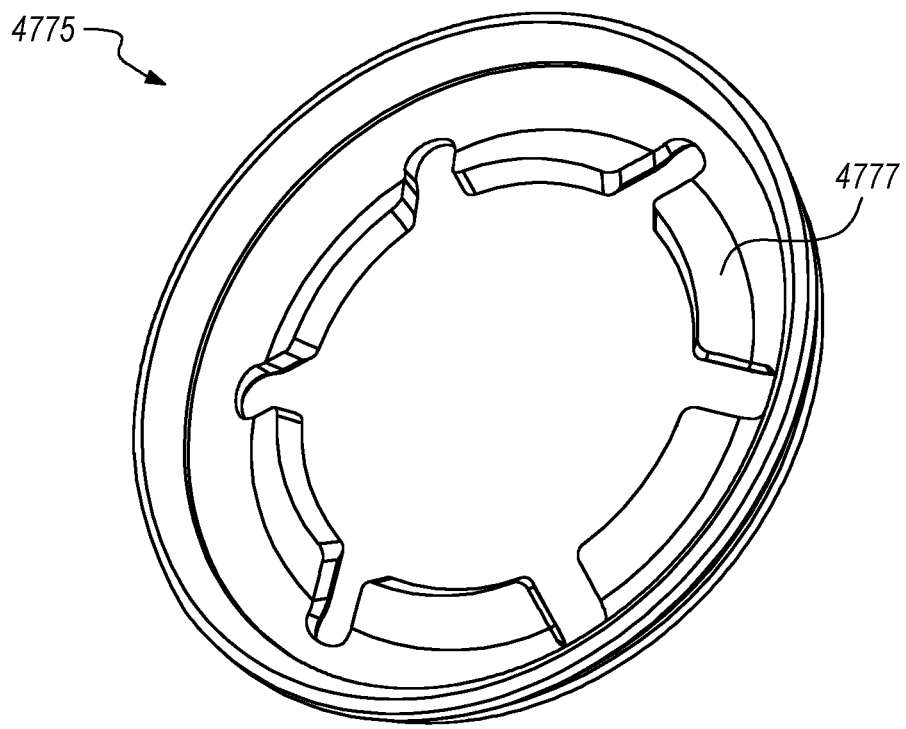

FIGS. 47A to 47H depict an attachment mechanism for coupling a needle hub 4774 to a polymeric syringe body 4710 according to various embodiments. FIG. 47A is an exploded view of a needle hub assembly including a needle 4772, a needle hub 4774, a needle retaining ring 4790, and a gasket 4715. While the embodiment depicted in FIG. 47A includes a needle latch and a needle latch actuator, these components are optional in a needle hub assembly for use with molded polymer injection system bodies, and other needle hub assembly embodiments may omit the needle latch and the needle latch actuator. In various embodiments, the polymeric syringe body 4710 may be molded from Cyclic Olefin Copolymer or Cyclic Olefin Polymer. As shown in FIG. 47D, the polymeric syringe body 4710 has a smooth needle coupling member 4711 at a distal end thereof. The needle hub 4774 has a retaining ring 4774 to couple onto the needle coupling member 4711.

The metal retaining ring 4775 includes teeth 4777 (see FIGS. 47G and 47H) that are biased in such a way to bend more readily in one direction compared to the opposite direction as described in U.S. Provisional Patent Application Ser. No. 62/827,767 62/827,767, which has been previously incorporated by reference herein. As such, the retaining ring 4775 can slip proximally over the needle coupling member 4711 (see FIG. 47E) more easily at the distal end of the molded polymer syringe body 4710, while providing relatively more substantial resistance to removing the retaining ring 4775 distally over the needle coupling member 4711. In fact, the teeth 4777 of the retaining ring 4775 may even gouge/dig into the needle coupling member 4711 when the needle hub 4774 is pulled away from the polymer syringe body 4710.

There is a self-braking action that occurs between the teeth 4777 and the polymer syringe body 4710 that helps resist the removal of the retaining ring 4775 over the needle coupling member 4711. The teeth 4777 tend to bind harder to the needle coupling member 4711 as more removal force is applied. This is due to the non-shallow angle that is formed between the teeth 4777 and the needle coupling member 4711 after assembly, which increases friction between the teeth 4777 and the needle coupling member 4711 with increasing removal force, thereby preventing the teeth 4777 from releasing the needle coupling member 4711. The domed curvature of the teeth 4777 and the surrounding metal of the retaining ring 4775 lend structural strength to the teeth 4777, which thereby squeeze the needle coupling member 4711 with substantial radial force, and help to reinforce the self-braking action and help the teeth 4777 to resist releasing the needle coupling member 4711. Interference between the needle coupling member 4711 and the retaining ring 4775 allows the needle hub 4772 to be mounted onto the polymer syringe body 4710 in the proximal direction while preventing removal of the needle hub 4772 from the polymer syringe body 4710 in the distal direction. The metal retaining ring 4775 has greater hardness and elasticity compared to the polymer syringe body 4710 due to its metallic composition.

While various components depicted in FIGS. 31 to 34 are described as off-the-shelf or safety needle retraction components, the dual chamber injection system conversion kit 3000 and the fluid transfer assembly 3002 can be used with a variety of injection systems and system components.

Exemplary Fluid Transfer Assembly for Dual Chamber Safe Injection Systems

FIGS. 48-63 depict a dual chamber injection system 5100 including a fluid transfer assembly configured to provide precise control of the handling, mixing, and delivery of the components of a multi-component injectable according to some embodiments. Similar to the dual chamber injection systems 100 depicted in FIGS. 6A-7B, 7G-7P, and 8-29D, and as shown in FIG. 51, the dual chamber injection system 5100 includes a syringe body 5110, proximal and distal stopper members 5114, 5112, and a plunger member 5116. The plunger member 5116 is inserted into an interior 5118 of the syringe body 5110 via a proximal opening in the syringe body 5110. The syringe body 5110 also includes a capped distal needle interface 5120 at the distal end thereof. While the dual chamber injection systems 100 depicted in FIGS. 6A-7B and 7G-7P have a staked needle, the syringe body 5110 has a Luer lock type distal needle interface 5120. The distal needle interface 5120 is not limited to Luer lock and may be any other type of needle/tubing interface. The distal needle interface 5120 is capped to minimize contamination and to facilitate retention of an optional vacuum in the interior 5118 of the syringe body 5110. Benefits of an optional vacuum include reduced drug exposure to air, force assist in transferring liquid drug components from the proximal drug chamber 5122 to the distal drug chamber 5124, and eliminating the need to vent the distal drug chamber during drug mixing thereby allowing a capped distal needle interface 5120. A capped distal needle interface 5120 minimizes user exposure in embodiments with toxic drug components.

The proximal and distal stopper members 5114, 5112 together with the syringe body 5110 define a proximal drug chamber 5122. The distal stopper member 5112 and the syringe body 5110 define a distal drug chamber 5124. The plunger member 5116 may be manually manipulated to insert the proximal stopper member 5114 relative to the syringe body 5110. If a non-compressible fluid is disposed in the proximal drug chamber 5122, inserting the proximal stopper member 5114 also inserts the distal stopper member 5112 relative to the syringe body 5110.

While the dual chamber injection systems 100 depicted in FIGS. 6A-7B and 7G-7P have a needle with various openings for fluid transfer and delivery (see FIGS. 7C-7F), the dual chamber injection system 5100 includes a fluid conveying assembly 5130 for fluid transfer and delivery.

As shown in FIG. 53, the fluid conveying assembly 5130 according to some embodiments includes a spine assembly 5000 and a piercing tube 4800. The spine assembly 5000 includes a distal tube 5010 and a solid elongate member 5020 partially disposed within the distal tube 5010 and partially disposed within the piercing tube 4800. The distal tube 5010 is generally a tubular member that is sealed by hermetic welds between the solid elongate member 5020 and the distal tube 5010.

Figure 55:
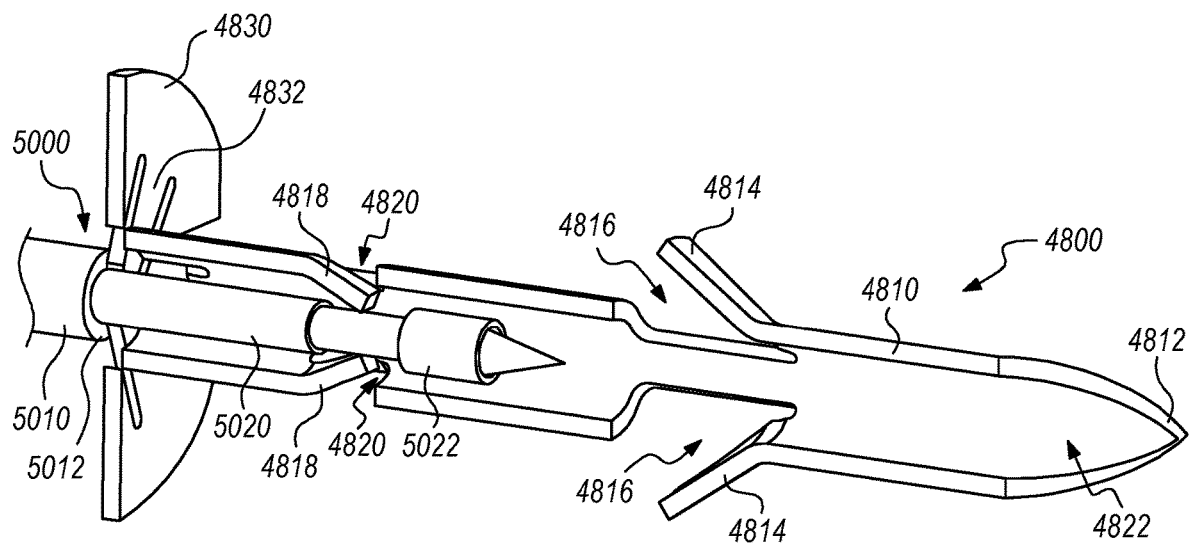

As described above, the solid elongate member 5020 may be coupled to the distal tube 5010 by a weld. As shown in FIG. 55, a proximal end of the distal tube 5010 forms a proximally facing shoulder 5012 at a junction with the solid elongate member 5020. The solid elongate member 5020 may be formed from various wires and bands. Alternatively, the solid elongate member 5020 may be formed from a single piece of material. In any case, the solid elongate member 5020 defines a recessed area and a distally facing shoulder 5022 near a proximal end thereof.

Figure 48:
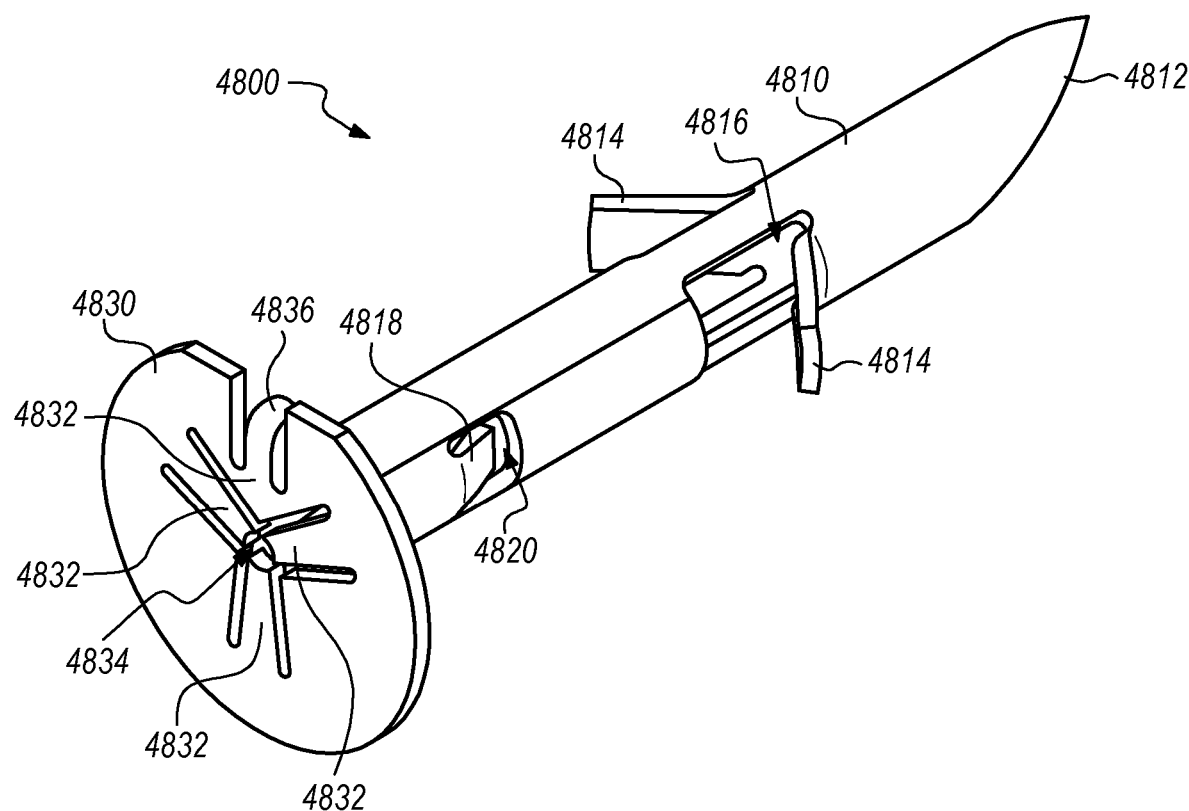

As shown in FIGS. 48 and 55, the piercing tube 4800 includes a tubular member 4810 movably coupled to a disc member 4830. The tubular member 4810 defines a pair of vacuum stops 4814 that extend radially outward and distally from an exterior surface of the tubular member 4810. The vacuum stops 4814 are configured to interfere with a funnel surface 4910 of a funnel insert 4900 (see FIG. 49) to stabilize the relative positions of the piercing tube 4800 and the funnel insert 4900 in a transport configuration and to tune an amount of force needed to move the funnel insert 4900 distally past the piercing tube 4800. The tubular member 4810 also defines a pair of middle openings 4816 into an interior of the tubular member 4810 adjacent respective ones of the pair of vacuum stops 4814. The tubular member 4810 further defines a pair of anti-retraction tabs 4818 that extend radially inward and proximally from an exterior surface of the tubular member 4810. The anti-retraction tabs 4818 are configured to interfere with the distally facing shoulder 5022 on the solid elongate member 5020 to limit distal movement of the solid elongate member 5020 relative to the piercing tube 4800. The tubular member 4810 also defines a pair of distal openings 4820 into an interior of the tubular member 4810 adjacent respective ones of the pair of anti-retraction tabs 4818. The piercing tube 4800 may be formed by bending a piece of sheet metal.

As shown in FIGS. 48 and 55, the disc member 4830 defines a plurality of radially inward telescoping stops 4832. The radially inward telescoping stops 4832 movably connected and disposed adjacent to the disc member 4830 to the tubular member 4810. One of the radially inward telescoping stops 4832 includes a connection member 4836 that connects the disc member 4830 to the tubular member 4810. The radially inward telescoping stops 4832 define an adjustable opening 4834 in an approximate center of the disc member 4830.

Figure 62:
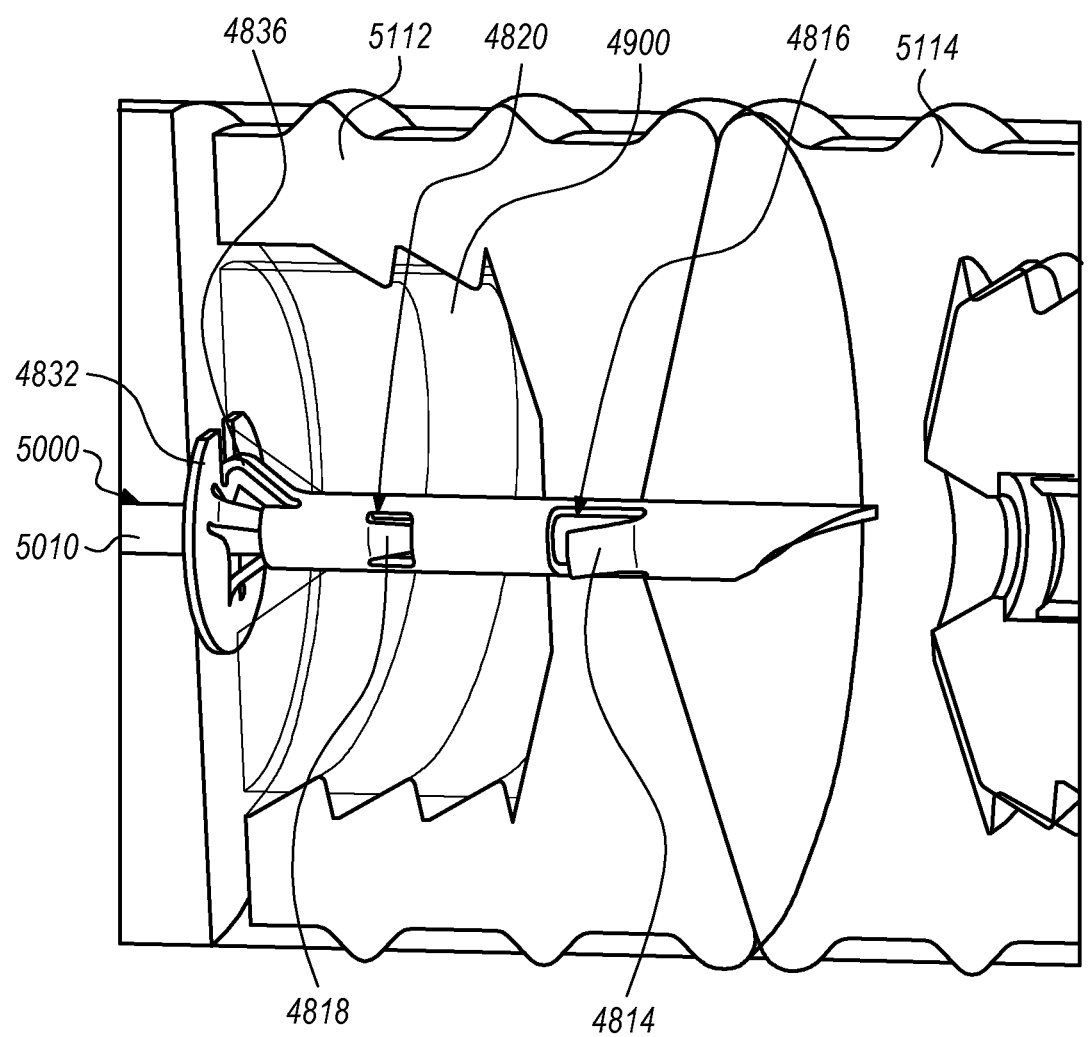

The adjustable opening 4834 is adjustable between a small configuration (shown in FIG. 48) and a large configuration (shown in FIG. 62 and described herein). When the adjustable opening 4834 is in the small configuration, the proximally facing shoulder 5012 on the distal tube 5010 interferes with the radially inward telescoping stops 4832 to prevent proximal movement of the distal exit to 5010 relative to the disc member 4830 of the piercing tube 4800. When the adjustable opening 4834 is in the large configuration, the distal tube 5010 is free to move proximally relative to the piercing tube 4800 as described. When the tubular member 4810 is pushed distally against the disc member 4830 (e.g., by a vacuum in a distal drug chamber 5124 and/or by distally directed force applied to the plunger member 5116, which both drive the distal stopper member 5112 distally over the piercing tube 4800), the radially inward telescoping stops 4832 are prevented from opening. However, when the tubular member 4810 is no longer pushed distally against the disc member 4830, then the radially inward telescoping stops 4832 are free to deform and change the adjustable opening 4834 from the small configuration to the large configuration (see FIG. 62 described herein).

Figure 49:
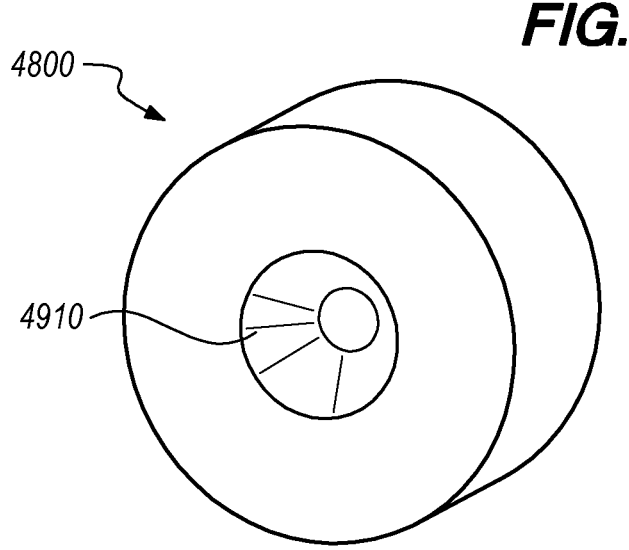
Figure 50:
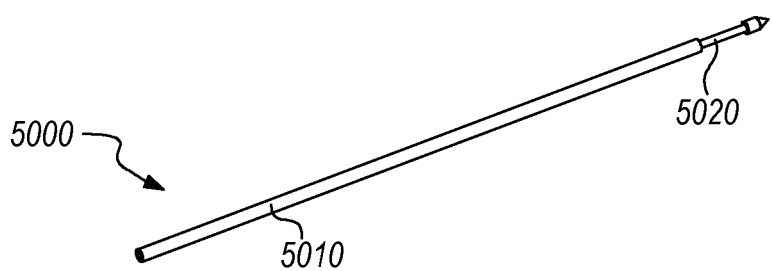

FIGS. 48 to 50 depicted the piercing tube 4800, the funnel insert 4900, and the spine assembly 5000 as separate components. FIGS. 51 to 53 depicted the dual chamber injection system 5100 in a transport configuration in which the vacuum stops 4814 interfere with the funnel surface 4910 of the funnel insert 4900 in the distal stopper member 5112 to increase the amount of distally directed force required to initiate distal movement of the distal stopper member 5112 relative to the syringe body 5110. The increased amount of distally directed force required by the vacuum stops 4814 and funnel surface 4910 facilitate device stability with a vacuum in the distal drug chamber 5124, which is present in some embodiments.

Figure 54:
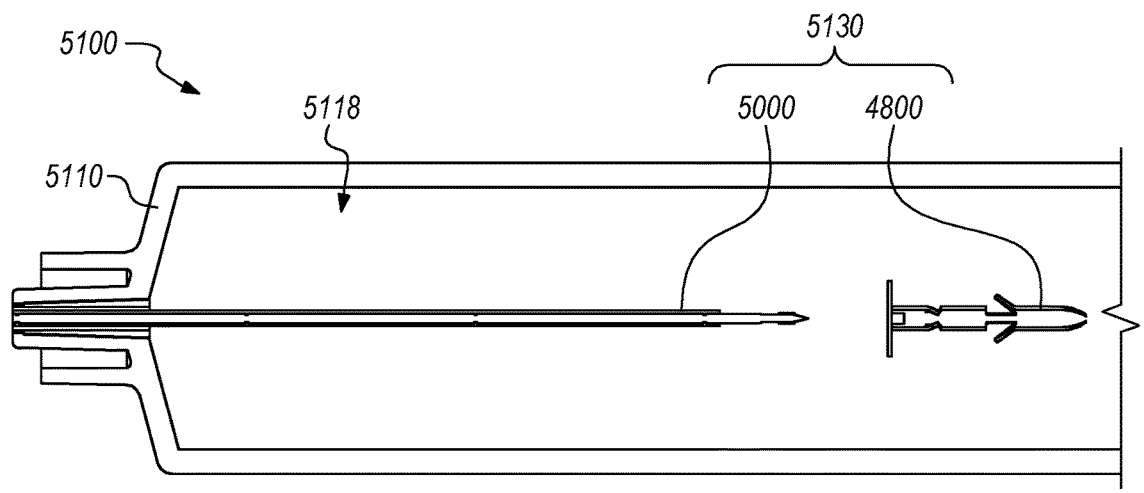

FIG. 54 depicts assembly of the dual chamber injection system 5100. First a spine assembly 5000 is inserted into an interior 5118 of the syringe body 5110. Then a piercing tube 4800 is threaded over a proximal end of the spine assembly 5000 to form the fluid conveying assembly 5130.

FIG. 55 depicts the piercing tube 4800 after it has been snapped over the spine assembly 5000. In this configuration, proximal movement of the spine assembly 5000 relative to the piercing tube 4800 is limited by interference between the proximally facing shoulder 5012 of the distal tube 5010 and the radially inward telescoping stops 4832 of the disc member 4830. Also, distal movement of the spine assembly 5000 and relative to the piercing tube 4800 is limited by interference between the distally facing shoulder 5022 of the solid elongate member 5020 and the anti-retraction tabs 4818 of the tubular member 4810. As such, FIG. 55 depicts the piercing tube 4800 walked onto the spine assembly 5000. FIG. 55 also depicts a sharp piercing tip 4812 of the piercing a proximal opening 4822 defined thereby.

Figure 56:
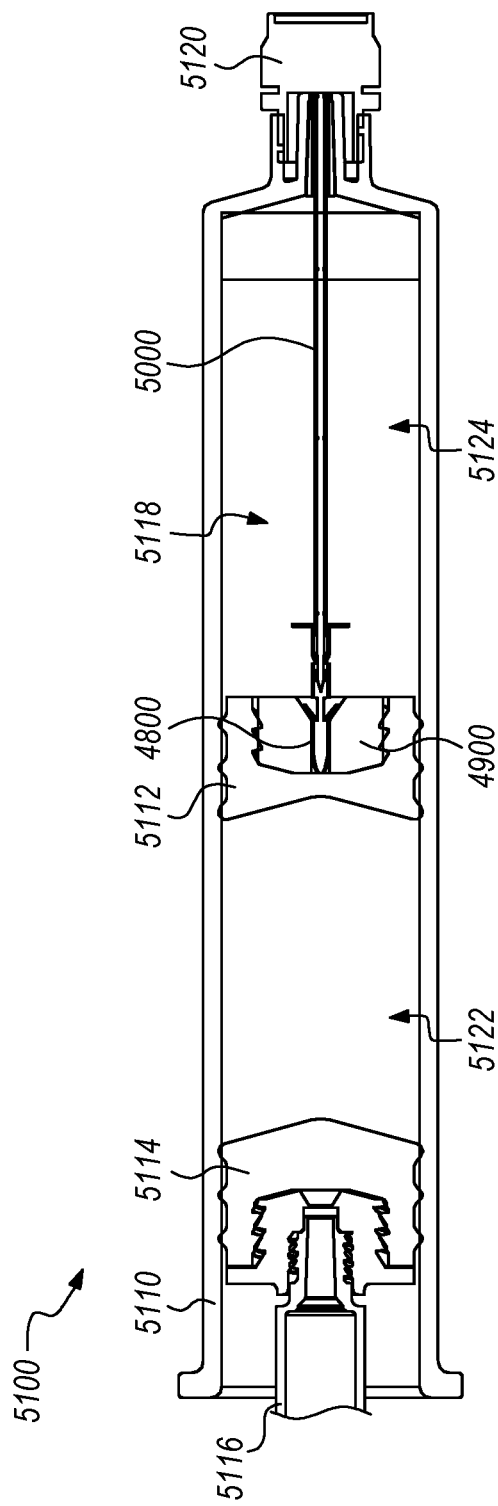

FIG. 56 depicts the next step in assembly of the dual chamber injection system 5100 following FIG. 54. A funnel insert 4900 is inserted into a distal stopper member 5112 (e.g., screwed or pressed into). Then the distal stopper member 5112 with the funnel insert 4900 is inserted through a proximal opening and into the interior 5118 of the syringe body 5110 until the vacuum stops 4814 of the piercing tube 4800 interfere with the funnel surface 4910 of the funnel insert 4900 (see FIGS. 48 and 49) to hold the distal stopper member 5112 in the transport configuration of the dual chamber injection system 5100 as described herein. Next, a proximal stopper member 5114 is inserted through the proximal opening into the interior 5118 of the syringe body 5110. Finally, a plunger member 5116 is coupled to the proximal stopper member 5114 (e.g., screwed into).

In some embodiments, a liquid drug component can be introduced into the proximal drug chamber 5122 before the proximal stopper member 5114 is inserted into the syringe body 5110. In such embodiments, the incompressibility of the liquid drug component maintains the position of the proximal stopper member 5114 relative to the distal stopper member 5112 until an exit flow path is opened into the proximal drug chamber 5122. In some embodiments, a liquid or dry/lyophilized drug component can be introduced into the distal drug chamber 5124 before or after the distal stopper member 5112 is inserted into the syringe body 5110. A liquid drug component in the distal drug chamber 5124 may be lyophilized in place using a vacuum, which can then be maintained in the distal drug chamber using a capped distal needle interface 5120. If a dry/lyophilized drug component is introduced into the distal drug chamber 5124, a vacuum can still be generated in the distal drug chamber 5124 and maintained using a capped distal needle interface 5120.

Figure 57:
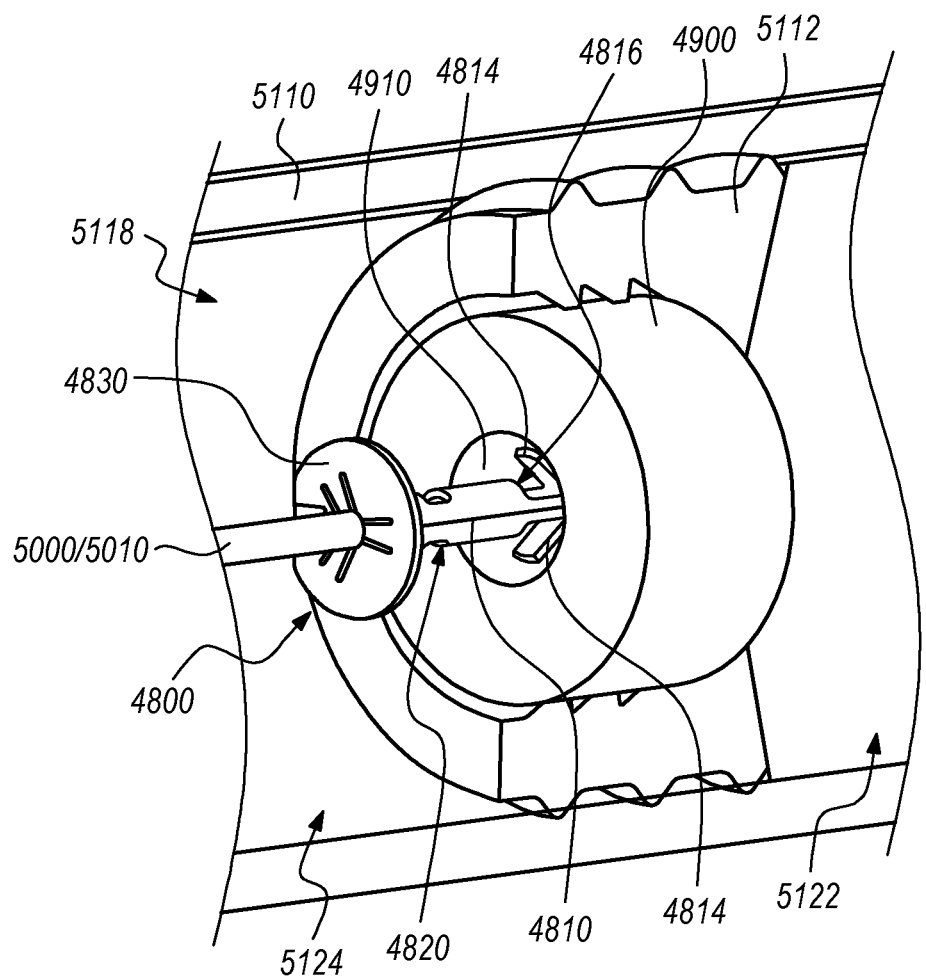

FIG. 57 depicts the distal stopper member 5112, the funnel insert 4900, the piercing tube 4800, and the spine assembly 5000 with the dual chamber injection system 5100 in the transport configuration as described above. In some embodiments with a vacuum in the distal drug chamber 5124, the vacuum can generate approximately 6.5 lbf of distally directed force on the distal stopper member 5112. As such, the vacuum stops 4814 of the piercing tube 4800 and the funnel surface 4910 of the funnel insert 4900 can be configured such that more than 6.5 lbf of distally directed force is required to overcome the interference between these components and to allow the piercing tube 4800 to enter into the funnel insert 4900 and pierce the distal stopper member 5112. For instance, the vacuum stops 4814 of the piercing tube 4800 and the funnel surface 4910 of the funnel insert 4900 can be configured such that 7.5 lbf of distally directed force is required to overcome the interference between these components and to allow the piercing tube 4800 to enter into the funnel insert 4900 and pierce the distal stopper member 5112. The extra 1 lbf of distally directed force can be provided by a user applying that force to the plunger member 5116.

Figure 58:
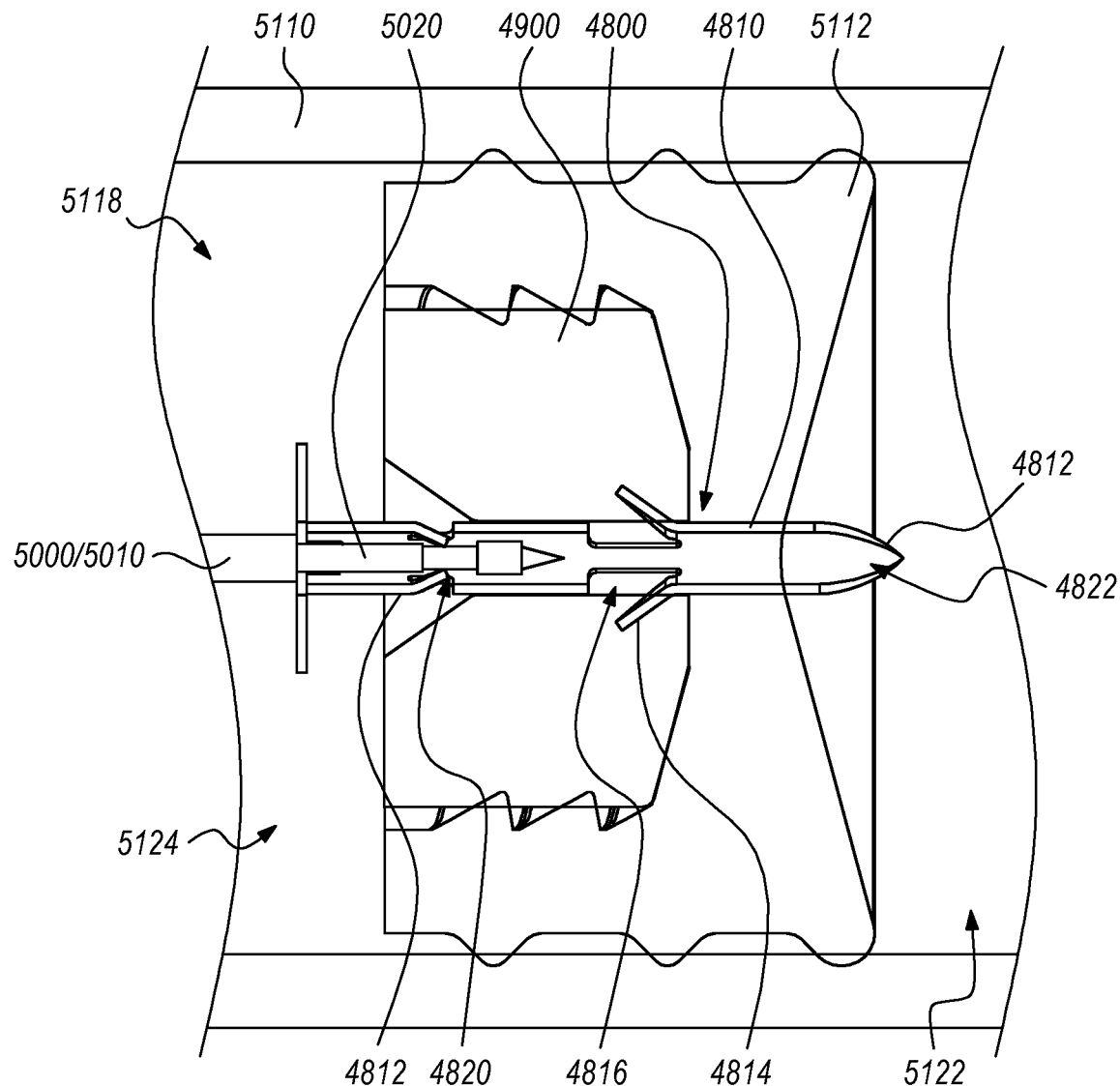
Figure 59:
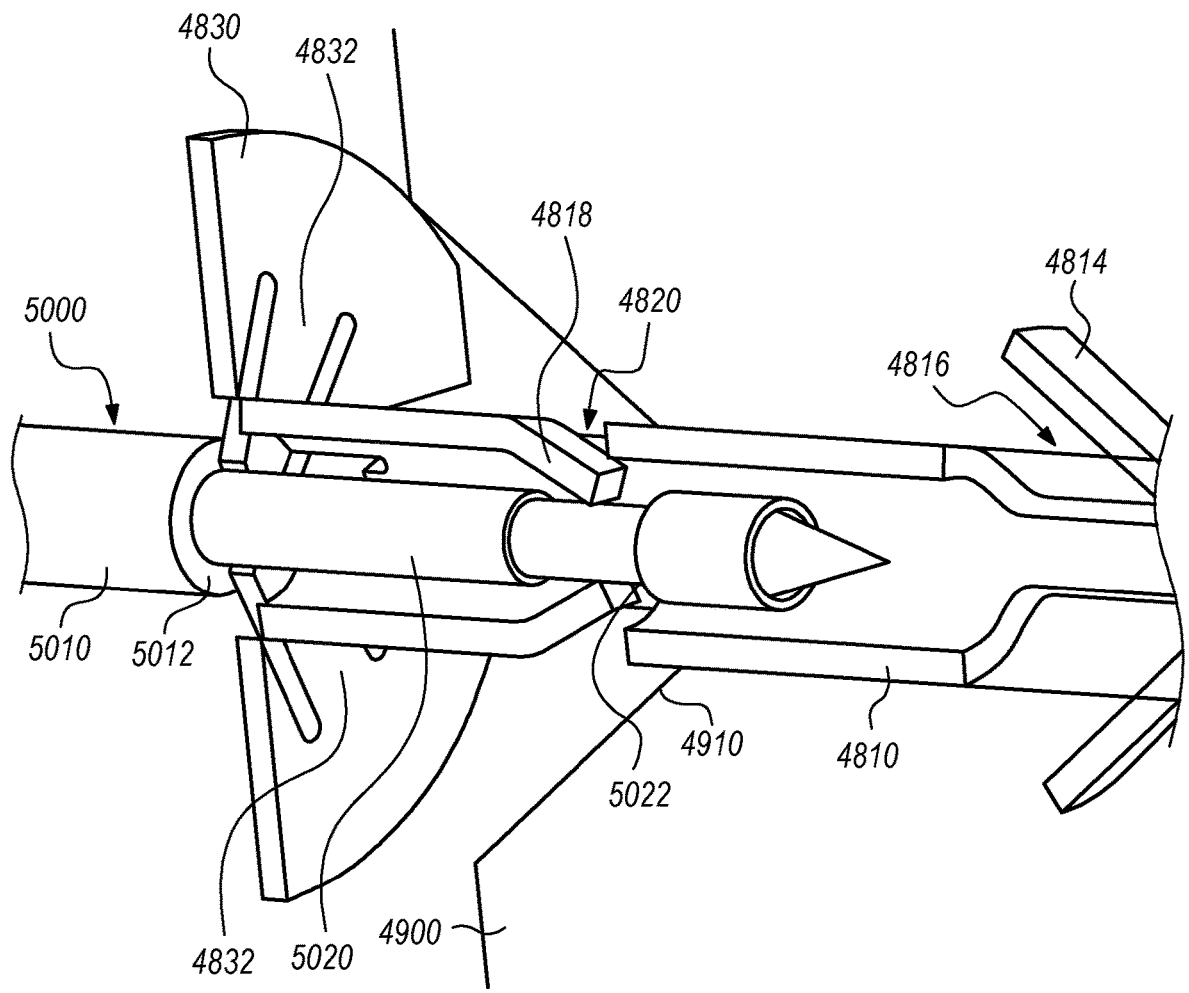

With application of sufficient distally directed force to overcome the interference between the vacuum stops 4814 of the piercing tube 4800 and the funnel surface 4910 of the funnel insert 4900, the sharp piercing tip 4812 of the piercing tube 4800 pierces the distal stopper member 5112 until the proximal opening 4822 of the piercing tube 4800 is in fluid communication with the proximal drug chamber 5122 as shown in FIGS. 58 and 59. An exemplary amount of force to drive the sharp piercing tip 4812 through the distal stopper member 5112 is approximately 4 lbf to approximately 5 lbf. With a vacuum delivering approximately 6.5 lbf of distally directed force, the system may be "self-piercing" after overcoming the interference between the vacuum stops 4814 of the piercing tube 4800 and the funnel surface 4910 of the funnel insert 4900. FIGS. 58 and 59 show the dual chamber injection system 5100 in a transfer configuration in which an exit flow path is open between the proximal and distal drug chambers (5122, 5124). The exit flow path includes the proximal opening 4822 of the piercing tube 4800, and interior of the piercing tube 4800, and the distal openings 4820 of the piercing tube. Because the proximal end of the solid elongate member 5020 the spine assembly 5000 only occupies the very distal end of the exit flow path, there is very little resistance to fluid flow through the exit flow path. In some embodiments, the force needed to drive the fluid flow is less than about 2.2 lbf. In embodiments where a vacuum is present in the distal drug chamber 5124, the distally directed force generated by the vacuum (e.g., 6.5 lbf) may pull a liquid drug component from the proximal drug chamber 5122 through the exit flow path into the distal drug chamber 5124. As the liquid drug component is pulled from the proximal drug chamber 5122, the proximal stopper member 5114 may also be pulled distally relative to the syringe body 5110.

Figure 60:
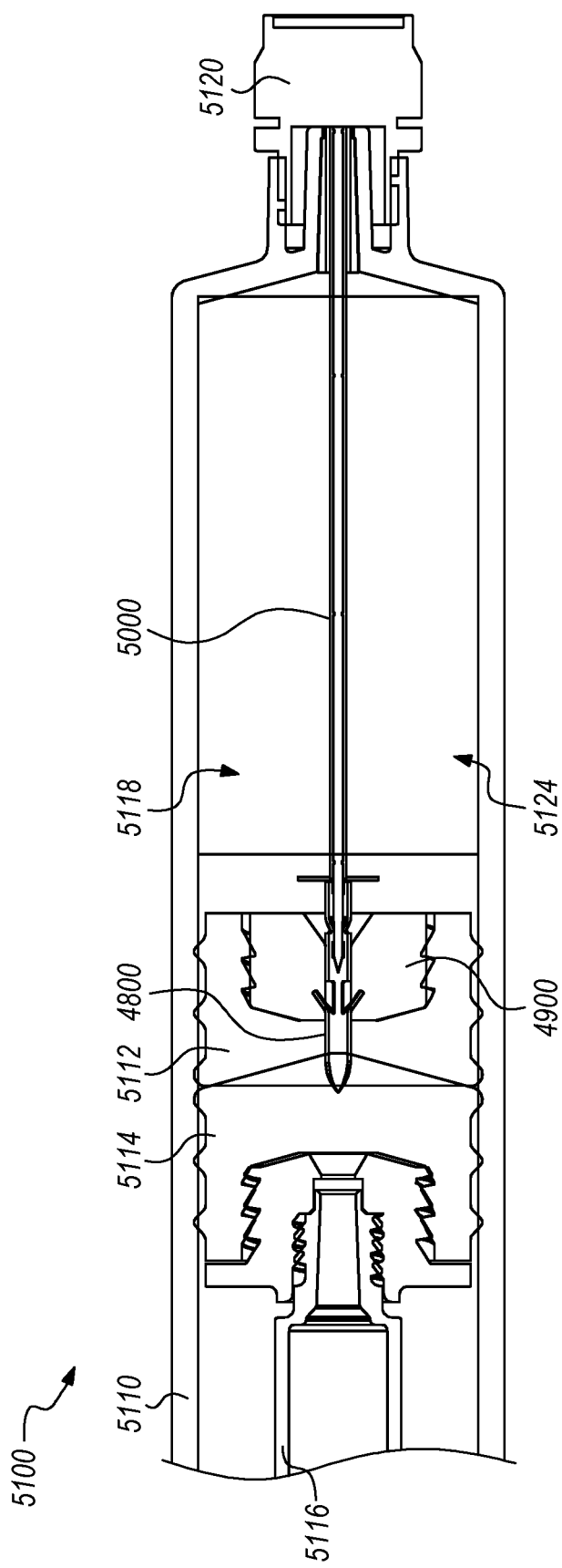

FIG. 60 depicts a next step in the multiple component drug injection method. The proximal drug chamber 5122 depicted in FIG. 56 has substantially or completely collapsed either by action of the vacuum in the distal drug chamber 5124 and/or user applied distally directed force to the plunger member 5116. Any liquid drug component in the proximal drug chamber 5122 as flow through the exit flow path into the distal drug chamber 5124. Lyophilized drug components in the distal drug chamber 5124 will be dissolved by the liquid drug component. The dual chamber injection system 5100 can be agitated to facilitate solubilization of any lyophilized drug components. At this point the dual chamber injection system 5100 is in a mixed configuration. The various components of the dual chamber injection system 5100 can be configured such that the vacuum is fully expended by moving the liquid drug component into the distal drug chamber 5124.

In the mixed configuration shown in FIG. 60, the mixed drug in the distal drug chamber 5124 is ready for injection. The syringe body 5100 includes distal end openings 5030 (see FIG. 52) to allow fluids such as the mixed drug to exit the distal drug chamber 5124. As described above, FIG. 52 depicts an embodiment of a the dual chamber injection system 5100 including a capped distal needle interface 5120, which blocks the outflow path from the distal drug chamber 5024 through the distal end openings 5030 until transfer of a liquid drug component and/or mixing of the mixed drug is completed. In such embodiments, a capped distal needle interface 5120 is uncapped before injection. A needle assembly including a needle (not shown) may be coupled to the uncapped distal needle interface 5120 before injection. In other embodiments, tubing may connect the uncapped distal needle interface 5120 to an IV bag before injection. After the uncapped distal needle interface 5120 is connected to the target of the injection, the injection can begin. Further application of distally directed force to the plunger member 5116 will now moves both the proximal and distal stopper members 5114, 5112 distally relative to the syringe body 5110 and forces the mixed drug from the distal drug chamber 5124 out the uncapped distal needle interface 5120 to perform the injection.

Figure 61:
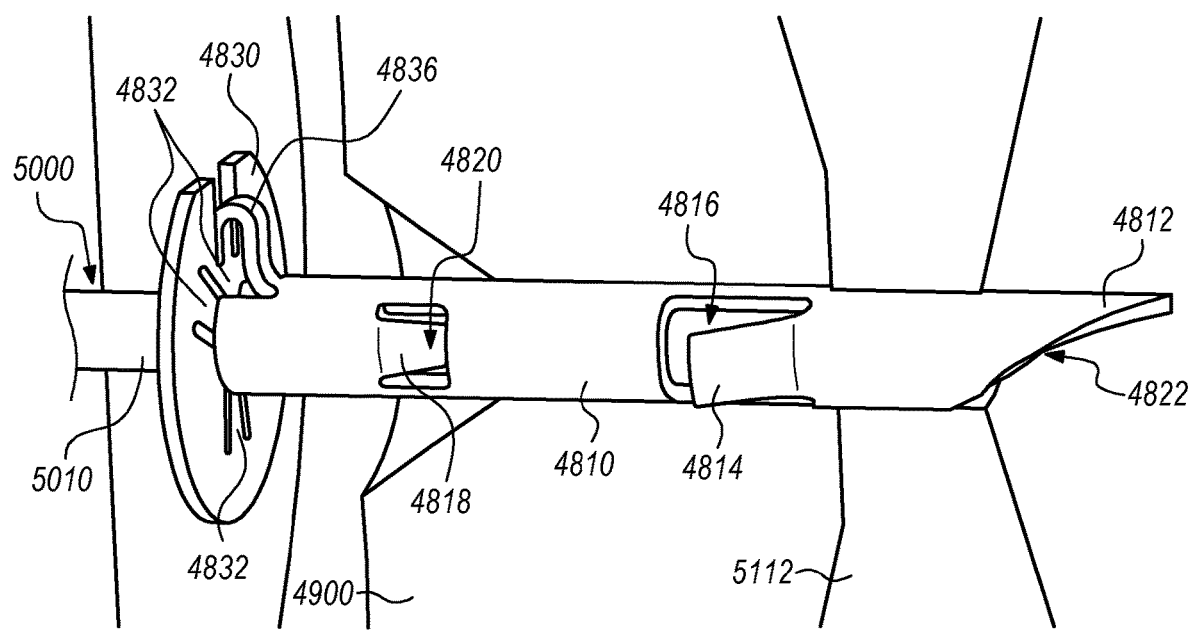

FIGS. 61 and 62 show that after the dual chamber injection system 5100 is in the mix configuration and the proximal and distal stopper members 5114, 5112 are in contact with each other. FIG. 61 shows that is pushing the tubular member 4810 against the disc member 4830 pushes the radially inward telescoping stops 4832 together and holds the adjustable opening 4834 in its small configuration, which latches the spine assembly 5000 to the piercing tube 4800. The relatively thick metal from which the piercing tube 4800 is made (e.g., 0.009") and a narrow sliding clearance (e.g., 0.0025") limits the degree to which the radially inward telescoping stops 4832 can then.

As shown in FIG. 62, further application of distally directed force to the plunger member 5116 closes a gap between the disc member 4830 and the funnel insert 4900 (FIG. 62). Distally directed force is then transferred through the funnel insert 4900 to push the disc member 4830 of the piercing tube 4800 distally away from the tubular member 4810 of the piercing tube 4800, while the tubular member 4810 is held stationary in the distal stopper member 5112 and the funnel insert 4900 (e.g., by barbs (not show)). This moves the disc member 4830 distally away from the tubular member 4810 and bends the radially inward telescoping stops 4832 away from the adjustable opening 4834 (see FIG. 48) to transform it from a small configuration to a large configuration. This unlatches the spine assembly 5000 from the piercing tube 4800 and allows the spine assembly 5000 to pierce the proximal stopper member 5114 through the piercing tube 4800, which remains held mostly in the proximal stopper member 5112 and funnel insert 4900 by the disc member 4830.

Figure 63:
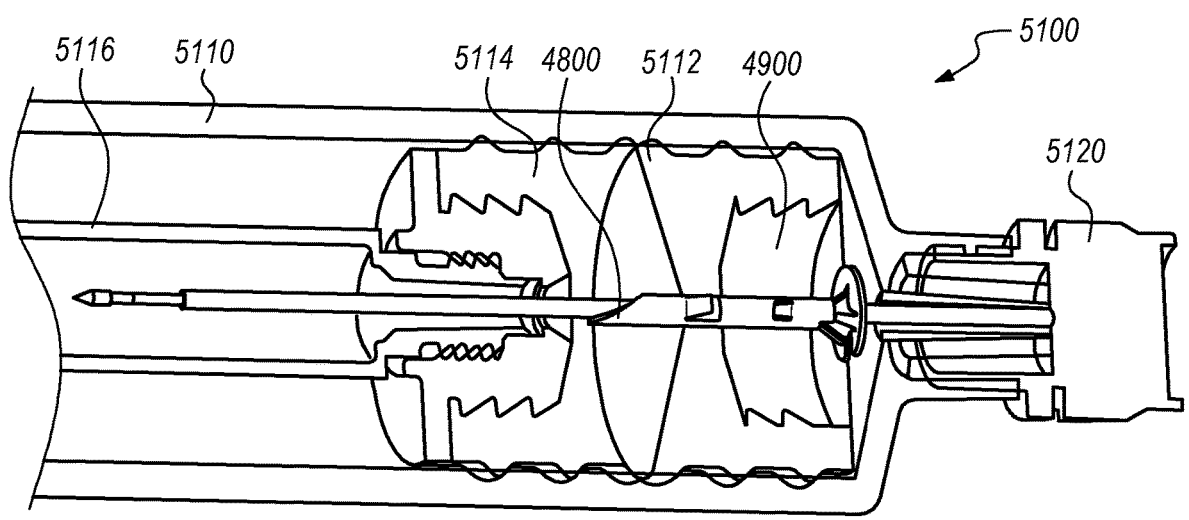

FIG. 63 depicts the dual chamber injection system 5100 after injection of the mixed drug from the distal drug chamber 5124. At this point the dual chamber injection system 5100 is in the completed configuration. The proximal stopper member 5114 is in contact with the distal stopper member 5112 which is in contact with a distal end of the syringe body 5110. A proximal end of the spine assembly 5000 has penetrated both the distal and proximal stopper members 5114, 5112 and entered the plunger member 5116. The piercing tube 4800 does not completely penetrate the proximal stopper member 5112, thereby minimizing the risk of retrograde flow into the plunger member 5116. In some embodiments, after injection of the mixed drug, the spine assembly 5000 and a needle attached thereto (not shown) may be retracted inside of the syringe body 5110 to provide a safe injection system. Details regarding retraction systems are described in U.S. Utility patent application Ser. No. 14/696,342, which was previously incorporated by reference herein.

The dual chamber injection system 5100 and its components depicted in FIGS. 48 to 63 prevent accidental and/or premature dispensing of drugs before transfer of a liquid drug component and/or mixing of the mixed drug is completed. At the same time, the dual chamber injection system 5100 includes a low resistance to injection after the mixed drug is prepared and ready for injection. The dual chamber injection system 5100 accomplishes this by the spine assembly 5000 stay locked to the piercing tube 4800 during transfer of liquid drug from the proximal drug chamber 5122 to the distal drug chamber 5124 and mixing of the drug thereby preventing incomplete mixture and fluid transfer. Once the spine assembly 5000 is unlocked from the piercing tube 4800, the resistance to distal movement of the proximal and distal stopper members 5114, 5114 over the spine assembly 5000 is minimal. While vacuum has been described in distal drug chambers of various embodiments, a vacuum is an optional feature of the injection system. Alternatively, vacuums may be present in both the proximal and distal drug chambers of some embodiments. The dual chamber injection system 5100 is compatible with needle retraction systems, but it may also be used without needle retraction systems. The dual chamber injection system 5100 is compatible with a wide variety of syringe sizes (e.g., 20 cc syringe).

While some of the prefilled dual chamber safety injection systems depicted and described herein include Luer lock connectors, the injection configurations and dual chamber configurations, including the anti-retraction mechanisms, the safe injection needle retraction systems, and the needle hub attachment mechanisms described herein can be used with cartridges an auto injector, and injection systems with syringes with staked needles or Luer slip connectors, and no needles such as those described in U.S. Utility patent application Ser. Nos. 15/801,281 and 15/801,259, which were previously incorporated by reference herein.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:
1. An injection system, comprising:
   a syringe body defining a proximal opening at a proximal end thereof and a distal needle interface at a distal end thereof;
   proximal and distal stopper members disposed in the syringe body, forming a proximal drug chamber between the proximal and distal stopper members and a distal drug chamber between the distal stopper member and the distal end of the syringe body;
   a plunger member configured to be manually manipulated to insert the proximal stopper member relative to the syringe body; and a fluid conveying assembly comprising
   a penetrating member configured to penetrate the distal stopper member to fluidly couple the proximal and distal drug chambers,
   a distal exit tube, wherein a distal end of the penetrating member is disposed in the distal exit tube, and
   a transfer member disposed at least partially around a portion of the penetrating member, wherein the transfer member defines a fluid passage,
wherein the distal exit tube comprises
   a distal end opening at a distal end thereof, and
   a proximal side opening disposed in the distal drug chamber.

2. The system of claim 1, wherein the transfer member comprises a sleeve disposed on the portion of the penetrating member.

3. The system of claim 2, wherein the sleeve defines the fluid passage on a surface of the portion of the penetrating member.

4. The system of claim 1, wherein the transfer member comprises a chamfered corner at a proximal end thereof.

5. The system of claim 1, wherein the portion of the penetrating member has a reduced diameter relative to a geometric feature at a distal end of the penetrating member and the distal exit tube at a proximal end of the portion of the penetrating member.

6. The system of claim 5, wherein a distal end of the geometric feature and a proximal end of the distal exit tube form proximal and distal shoulders at proximal and distal ends of the portion of the penetrating member respectively.

7. The system of claim 6, wherein a diameter of the distal end of the geometric feature is substantially the same as or larger than a diameter of the proximal end of the distal exit tube.

8. The system of claim 1, wherein the penetrating member is configured to pierce the distal stopper member and the transfer member is configured to dilate the distal stopper member and maintain an open fluid passage.

9. The system of claim 1, wherein the transfer member comprises a living hinge.

10. The system of claim 1, wherein the transfer member comprises an elongate side opening.

11. The system of claim 1, wherein the distal stopper member comprises a funnel configured to guide a proximal end of the penetrating member toward a center of the distal stopper member.

12. The system of claim 11, wherein the transfer member comprises a radially extending member configure to physically interfere with the funnel to halt proximal movement of the transfer member relative to the funnel and the distal stopper member when the radially extending member contacts the funnel.

13. The system of claim 1, wherein the penetrating member comprises a geometric feature at a proximal end thereof.

14. The system of claim 13, wherein the geometric feature is configured to penetrate the distal stopper member.

15. The system of claim 1, wherein the distal exit tube comprises a split open distal end.

16. The system of claim 1, further comprising a ring welded to the distal exit tube.

17. The system of claim 16, wherein the ring is configured to prevent a distal end of the distal exit tube from extending more than a predetermined distance toward a distal end of the distal needle interface.

18. The system of claim 1, wherein the system has
a transport configuration wherein the penetrating member is entirely disposed in the distal drug chamber,
a transfer configuration wherein the penetrating member has at least partially pierced the distal stopper member, and wherein the penetrating member and the transfer member are at least each partially disposed in the proximal drug chamber, and
a mixed configuration wherein the proximal and distal stopper members are in contact with each other, thereby transferring a first drug component from the proximal drug chamber to the distal drug chamber to mix the first drug component with a second drug component in the distal drug chamber.

19. The system of claim 18, wherein the fluid passage forms a fluid path between the proximal and distal drug chambers when the system is in the transfer configuration.

20. The system of claim 18, wherein the transfer member does not fully penetrate the proximal stopper member in the mixed configuration or during injection.

21. The system of claim 18, wherein the system is configured to transform from the transport configuration to the transfer configuration with application of a pre-determined amount of force to the distal stopper member.

22. The system of claim 21, wherein the pre-determined amount of force is approximately 3-5 lbf of distally directed force.

23. The system of claim 1, wherein first and second sizes of the proximal and distal drug chambers is modified by movement of the proximal and distal stopper members relative to the syringe body.

24. The system of claim 1, wherein the proximal and distal drug chambers respectively contain first and second components of a drug to be mixed together prior to injecting into a patient.

25. The system of claim 1, wherein the transfer member is formed from metal.

26. The system of claim 1, wherein the transfer member is formed from polymer.

27. An injection system, comprising:
a syringe body defining a proximal opening at a proximal end thereof and a distal needle interface at a distal end thereof;
proximal and distal stopper members disposed in the syringe body, forming a proximal drug chamber between the proximal and distal stopper members and a distal drug chamber between the distal stopper member and the distal end of the syringe body;
a plunger member configured to be manually manipulated to insert the proximal stopper member relative to the syringe body; and
a fluid conveying assembly comprising
   a penetrating member configured to penetrate the distal stopper member to fluidly couple the proximal and distal drug chambers,
   a distal exit tube, wherein a distal end of the penetrating member is disposed in the distal exit tube, and
   a transfer member disposed at least partially around a portion of the penetrating member, wherein the transfer member defines a fluid passage,
wherein the portion of the penetrating member has a reduced diameter relative to a geometric feature at a distal end of the penetrating member and the distal exit tube at a proximal end of the portion of the penetrating member
wherein a distal end of the geometric feature and a proximal end of the distal exit tube form proximal and distal shoulders at proximal and distal ends of the portion of the penetrating member respectively, wherein the transfer member has a closed configuration wherein the transfer member is disposed around the portion of the penetrating member between the proximal and distal shoulders, the transfer member having a first diameter, and an open configuration wherein the transfer member has a second diameter larger than the first diameter such that the penetrating member and the distal exit tube are slidable within the transfer member.

28. The system of claim 27, wherein the transfer member is converted from the closed configuration to the open configuration by an application of between approximately 6 lbf and approximately 10 lbf on the distal exit tube provided by hydraulic pressure on the distal stopper member from the plunger member.

29. The system of claim 27, wherein the transfer member comprises a distally directed funnel at a distal end thereof, wherein a proximal end of the distal exit tube is disposed in the distally directed funnel when the transfer member is in the closed configuration, and wherein the proximal end of the distal exit tube is configured to wedge open the transfer member with distal movement of the distal exit tube relative to the transfer member to transform the transfer member from the closed configuration to the open configuration.

30. The system of claim 27, wherein the first diameter is less than or equal to a diameter of the distal end of the geometric feature.

31. The system of claim 27, wherein the second diameter is greater than a diameter of the proximal end of the distal exit tube.

32. The system of claim 27, wherein the transfer member is configured to transform from the closed configuration to the open configuration with application of a pre-determined amount of force to the distal exit tube.

33. The system of claim 32, wherein the pre-determined amount of force is approximately 6 lbf to approximately 10 lbf of distally directed force.

34. An injection system, comprising:

a syringe body defining a proximal opening at a proximal end thereof and a distal needle interface at a distal end thereof;

proximal and distal stopper members disposed in the syringe body, forming a proximal drug chamber between the proximal and distal stopper members and a distal drug chamber between the distal stopper member and the distal end of the syringe body;

a plunger member configured to be manually manipulated to insert the proximal stopper member relative to the syringe body; and a fluid conveying assembly comprising a penetrating member configured to penetrate the distal stopper member to fluidly couple the proximal and distal drug chambers, a distal exit tube, wherein a distal end of the penetrating member is disposed in the distal exit tube, and a transfer member disposed at least partially around a portion of the penetrating member, wherein the transfer member defines a fluid passage, wherein the distal exit tube comprises a proximal side opening and a proximal end opening, and wherein the penetrating member has a length greater than a distance between the proximal side opening and the proximal end opening.

35. An injection system, comprising:

a syringe body defining a proximal opening at a proximal end thereof and a distal needle interface at a distal end thereof;

proximal and distal stopper members disposed in the syringe body, forming a proximal drug chamber between the proximal and distal stopper members and a distal drug chamber between the distal stopper member and the distal end of the syringe body;

a plunger member configured to be manually manipulated to insert the proximal stopper member relative to the syringe body; and a fluid conveying assembly comprising a penetrating member configured to penetrate the distal stopper member to fluidly couple the proximal and distal drug chambers, a distal exit tube, wherein a distal end of the penetrating member is disposed in the distal exit tube, and a transfer member disposed at least partially around a portion of the penetrating member, wherein the transfer member defines a fluid passage, wherein the system has a transport configuration wherein the penetrating member is entirely disposed in the distal drug chamber, a transfer configuration wherein the penetrating member has at least partially pierced the distal stopper member, and wherein the penetrating member and the transfer member are at least each partially disposed in the proximal drug chamber, and a mixed configuration wherein the proximal and distal stopper members are in contact with each other, thereby transferring a first drug component from the proximal drug chamber to the distal drug chamber to mix the first drug component with a second drug component in the distal drug chamber, and wherein after the system has reached the mixed configuration, the distal exit tube wedges open the transfer member and slides proximally within the transfer member with further distal movement of the distal stopper member.

36. An injection system, comprising:

a syringe body defining a proximal opening at a proximal end thereof and a distal needle interface at a distal end thereof;

proximal and distal stopper members disposed in the syringe body, forming a proximal drug chamber between the proximal and distal stopper members and a distal drug chamber between the distal stopper member and the distal end of the syringe body;

a plunger member configured to be manually manipulated to insert the proximal stopper member relative to the syringe body; and a fluid conveying assembly comprising a penetrating member configured to penetrate the distal stopper member to fluidly couple the proximal and distal drug chambers, a distal exit tube, wherein a distal end of the penetrating member is disposed in the distal exit tube, and a transfer member disposed at least partially around a portion of the penetrating member, wherein the transfer member defines a fluid passage, wherein the transfer member comprises a latch having a latched state and an unlatched state, wherein the latch prevents axial movement of the penetrating member and distal exit tube relative to the transfer member in the latched state, and wherein the latch allows axial movement of the penetrating member and distal exit tube relative to the transfer member in the unlatched state.

37. The system of claim 36, wherein the latch comprises a plastic hinge.

38. The system of claim 37, wherein the plastic hinge opens to transform the latch from the latched to the unlatched state.

39. The system of claim 37, wherein the plastic hinge opens in response to application of a predetermined amount of force to the latch.

40. The system of claim 39, wherein the predetermined amount of force is approximately 6 lbf to approximately 10 lbf of distally directed force.

41. The system of claim 36, wherein the latch comprises a frangible link to hold the transfer member in the latched state until a predetermined amount of force is applied to the latch.

42. The system of claim 41, wherein the predetermined amount of force is approximately 6 lbf to approximately 10 lbf of distally directed force.

\* \* \* \* \*